(12) United States Patent
Feinstein et al.

(10) Patent No.: US 6,833,237 B1
(45) Date of Patent: Dec. 21, 2004

(54) GENES INVOLVED IN STROKE RESPONSE AND/OR REGULATED BY FK506, PROTEINS ENCODED THEREBY, AND METHODS OF USE

(75) Inventors: Elena Feinstein, Rehovot (IL); Igor Mett, Rehovot (IL); Sylvia G. Kachalsky, Rehovot (IL); Svetlana Gorodin, Rishon-le-Zion (IL)

(73) Assignees: Quark Biotech, Inc., Cleveland, OH (US); Fujitsawa Pharmaceutical Co., Ltd., Osaka (JP)

( * ) Notice: Subject to any disclaimer, the term of this patent is extended or adjusted under 35 U.S.C. 154(b) by 41 days.

(21) Appl. No.: 10/021,338

(22) Filed: Dec. 12, 2001

Related U.S. Application Data

(60) Provisional application No. 60/254,542, filed on Dec. 12, 2000.

(51) Int. Cl.[7] ............ C12Q 1/00; G01N 33/53; C12N 15/63
(52) U.S. Cl. ................ 435/4; 435/6; 435/7.1; 435/7.2; 514/44; 536/23.5
(58) Field of Search .............. 435/4, 6, 7.1, 7.2; 514/44; 536/23.5

(56) References Cited

PUBLICATIONS

Horn and Limburg. Calcium Antagonists for Ischemic Stroke: A Systematic Review. Stroke. 2001; 32(2): 570–6.

Hugon et al. The presence of calbindin in rat cortical neurons protects in vitro from oxidative stress. Brain Res. Jan. 29, 1996; 707(2): 288–92.

Lipton. Ischemic Cell Death in Brain Neurons. Physiological Reviews. Oct. 1999; 79(4): 1434–1567.

Lockyer et al. CAPRI regulates $Ca^{+2}$–dependent inactivation of the Ras–MAPK pathway. Current Biology. 2001; 11:981–986.

Mingawa et al. District Phosphoinositide Dinding Specificity of the GAP1 Family Proteins: Characterization of the Pleckstrin Homology Domains of MSARAL and KIAA0538. Biochem. Biophys. Res. Comm. 2001; 288:87–90.

Signore et al. Immunohistochemical Localization of the $InsP_4$ Receptor GTPase–Activating Protein GAP1$^{IP4BP}$ in the Rat Brain. J. Neurosci. Res. Feb. 1, 1999; 55:321–328.

*Primary Examiner*—Gary Kunz
*Assistant Examiner*—Stephen Gucker
(74) *Attorney, Agent, or Firm*—John P. White; Cooper & Dunham LLP

(57) ABSTRACT

Genes and the proteins encoded thereby that are involved in stroke response and/or are regulated by FK506 are disclosed. These genes were discovered using in vivo or in vitro stroke models by determining which genes were differentially upregulated or downregulated upon treatment of the model with FK506. They were also found by a functional assay of genes specifically selected for conferring to cells resistance to hypoxia, dopamine or glutamate treatment. The disclosure includes such genes and proteins as well as analogs, salts and functional derivatives of such proteins, and DNA encoding such analogs, and methods of use. Methods for treating the effects of stroke, hypoxia and/or ischemia by regulating such genes or proteins are disclosed. Methods for screening for compounds capable of regulating the genes and proteins of the invention are also disclosed.

5 Claims, 7 Drawing Sheets

1st round

4th round

SEQUENCE LISTING

<160> NUMBER OF SEQ ID NOS: 131

<210> SEQ ID NO 1
<211> LENGTH: 269
<212> TYPE: DNA
<213> ORGANISM: Homo sapiens

<400> SEQUENCE: 1

```
ccaacttgcc cgttgtccac gggtcccacc ccttcttgcc gctcctcctc tgcaggtccc    60
gccctctccc cctgcctcac tcccaatgtc tcctttggct aagcccctc cacaggcccc   120
acctgctctg gccacacctc ctctgcaggc ccttccctct ccgcctgcct cattccctgg   180
gcaggcccct ttctcaccct ctgcctcact cccaatgtct cctttggcca cgcctcctcc   240
acaggcccca cctgttctgt agttagtta                                     269
```

<210> SEQ ID NO 2
<211> LENGTH: 280
<212> TYPE: DNA
<213> ORGANISM: Homo sapiens

<400> SEQUENCE: 2

```
ccaagtccac ccgatcacaa ggctcagctc ttaagtgctc tgcgatactg cttttctaac    60
aatgcctggt gcctccctga gtgaattccc aataggagtc tttccacttt agtccaacat   120
gaggcaagta gttgcaggtg ccaggtaaca taatgagctc caccttggta atcactctga   180
gtagacaatg ctcaaaaaaa cagagcacca cataatgtat caaccctaac agtcacccctt   240
ctgacatctc tattggaaag aggggataag tagttagtta                        280
```

<210> SEQ ID NO 3
<211> LENGTH: 261
<212> TYPE: DNA
<213> ORGANISM: Homo sapiens

<400> SEQUENCE: 3

```
cctttaaatt tttacactat cacactttat ttattcaatc accaagcccc accttatcta    60
ttcccctgct cacacacaaa tccactattc taatcctgct tacacacccc ttccacaggg   120
ttttatctca cttatgataa aatccaaaac tcacagcata gccactctcc ccaaagcata   180
ctatgcttta accacactgg tctttcctaa aagtttctcc tattccccaa tctttcttcc   240
ttactctaag gtagttagtt a                                             261
```

<210> SEQ ID NO 4
<211> LENGTH: 261
<212> TYPE: DNA
<213> ORGANISM: Homo sapiens

<400> SEQUENCE: 4

```
taactaacta gggaacctgg gggccaaggg gccccagcag tcagcaccaa tgcaatagtc    60
cttgaagatc acggccaaag ctatacttgc tctggacagg taactccccc tttcatgggc   120
```

```
agggtggta aaaggagcaa gcagaagcaa aaaggaattt tcctctaaaa acagaattgc      180
tgaaaggcac ttaatagagg gatagggcc agacacggtg gctcacacct ataatcccag      240
tactttaata ggaagaggct g                                               261

<210> SEQ ID NO 5
<211> LENGTH: 110
<212> TYPE: DNA
<213> ORGANISM: Homo sapiens

<400> SEQUENCE: 5
taactaacta tgccaaaggg aaatgttaag cttgggaact gagtcacgca atagcctttt     60
gtccctaagc agatggctgt aagacagaag gtcacctatc tcccgagtgg                110

<210> SEQ ID NO 6
<211> LENGTH: 256
<212> TYPE: DNA
<213> ORGANISM: Homo sapiens

<400> SEQUENCE: 6
taactaacta gataagtgat ctgtggccac atttgcagta cgtgatcctg acccactggc     60
cactgctaat tggataataa gcagctacca catccagtat gagccagtca gatcctctct    120
cttgggaaac tagcattcac agccagtgcc tctacagaga aggaagcata agcatttaga    180
aagatagttc tcctgactct aggggccac tggtaataac aatctcagtt tctgaggctt     240
tccagtttct ggatcc                                                     256

<210> SEQ ID NO 7
<211> LENGTH: 403
<212> TYPE: DNA
<213> ORGANISM: Rattus sp.
<220> FEATURE:
<221> NAME/KEY: misc_feature
<222> LOCATION: (255)..(255)
<223> OTHER INFORMATION: n

<400> SEQUENCE: 7
cctcagtagg agggagcgcg tgtgtgtgtg tgtgcgcgtg tgtgagtgtg tgtaacaacc     60
cagaaagctg gtaagagctg cagagaggca gtgtttatta gattcacact tagacactga    120
ttgtgggttc tggtttagct cttttataat tgtaaagtta tattttttgct gctttgtaat    180 aggataattc ttaagcatca tcttaaaata gaggtatttt gattcttttt tgtggagctg    240
tgactaaagt gcagngtctc acataggcta agcaagtgct gtgcactgag ttgaaccccca    300 gcagaagtag gtgctgcaag tgtaaaacaa ggctaaaggg cctaatgcac acagcctgtg    360
caggccgcga gtgcaccgac tataagcccc atgctattaa agc                       403

<210> SEQ ID NO 8
<211> LENGTH: 401
<212> TYPE: DNA
<213> ORGANISM: Rattus sp.

<400> SEQUENCE: 8
cctcagtagg agggagcgcg tgtgtgtgtg tgtgcgcgtg tgtgagtgtg tgtaacaacc     60
cagaaagctg ggaagagctg cagagaggca gtgtttatta gattcacact tagacactga    120
ttgtgggttc tggcttagct cttttataat tgtacagcta tattttttgct gctttgtaat    180 aggataattc ttaagcatca tcttaacata gaggtatttt gcttcttttt tgtggcgctt    240
gacattaagt gcagcctctc acataggcta agcaagtgct gcgcacttga gtgaactgca    300
```

-continued

```
gcagaagtag tcgctgcacg tgtaaaacaa ggctacagat tctaatgcac acagcctgtg    360
cagaccgcgt gtccaccgtc tataaggcat ggctataacg g                        401
```

<210> SEQ ID NO 9
<211> LENGTH: 402
<212> TYPE: DNA
<213> ORGANISM: Rattus sp.
<220> FEATURE:
<221> NAME/KEY: misc_feature
<222> LOCATION: (237)..(237)
<223> OTHER INFORMATION: n

<400> SEQUENCE: 9

```
ctttaatagc catggcctta tagacggtgg ccacgcggcc tgcacaggct gtgtgcatta    60 ggcccttag ccttgtttta cacttgcagc acctacttct gctgggttc aactcagtgc     120 acagcacttg cttagcctat gtgagaccct gcacttaatg cccagcacca caaaaagaa    180 acaaaatacc tctattttaa gatgatgctt aagaattatc ctattacaaa gcagcanaaa   240
tataacttta caattataaa agagctaaac caggacccac aatcagtgtc taagtgtgaa   300
tctaataaac actgcctctc tgcagctctt accagctttc tgggttggta cacacactca   360
cacacgcgca cacacacaca cacgcgctcc ctcctactga gg                      402
```

<210> SEQ ID NO 10
<211> LENGTH: 410
<212> TYPE: DNA
<213> ORGANISM: Rattus sp.

<400> SEQUENCE: 10

```
tggagctaat tgcgcgcggc cgcggtacga cgaacctgcc cctgatgacc ctcaccccttt   60 ttgcataggt cactggatcc cactgtcctt cctcggtgct tacacacttt acagacccttt  120 taggcgagcc cttgcataga gcgttatctc agtgctccat tccagtcctg actccctgtg   180
gccattgaga ctttggattt aagaactcac attgctaggg agagggcttt gctgggaaa    240 ggtgactcct ctgtaaccta gcctcttgtg ctcctccatg acagaaatgc tgggtggagt   300
tttacatttg ccaatggcca gcttgtgaat atcttcatat acactttcta ttcatgttac    360
tgtagtttct gttttgaaat aaaacttctg aatgtaaaaa aaaaaaaaa                410
```

<210> SEQ ID NO 11
<211> LENGTH: 242
<212> TYPE: DNA
<213> ORGANISM: Rattus sp.

<400> SEQUENCE: 11

```
cttggtcaca gtgctttcct tacacccctta tgatgaaagt cactgtaaga agggctgctg    60
gcagtccagg cacaccctgt gtgcagagtc ggccatgctt tgggagggtg tcaggaaaga   120
gtcatttact ttgactgcct gtgggctgac ttcagaactt caggtcttaa ggtttgctgg    180
cttctgaaaa cactttctaa agagcccatg aaatataaat ataactaact tagaaagccc   240
tg                                                                    242
```

<210> SEQ ID NO 12
<211> LENGTH: 69
<212> TYPE: DNA
<213> ORGANISM: Rattus sp.

<400> SEQUENCE: 12

```
ttttttttttt tttttttttt tttttaaaaa ttcaaggatg gggttaaagg gggaattccc      60
gggggggggg                                                              69

<210> SEQ ID NO 13
<211> LENGTH: 165
<212> TYPE: DNA
<213> ORGANISM: Rattus sp.

<400> SEQUENCE: 13
ggtacggcgt acctgcctcc cagtcttctc ttttctatag catggcttta agcctgcctc      60
cttgacatgc tgtatatatt ctattgtatt tgtttcattg tcccacactt aactcaggtg     120
tgctaaaaat aaaagtaaat tttaacagtc aaaaaaaaaa aaaaa                     165

<210> SEQ ID NO 14
<211> LENGTH: 172
<212> TYPE: DNA
<213> ORGANISM: Rattus sp.

<400> SEQUENCE: 14
tttttttttt ttttttggac ggtaaaaatt aactttaatt ttaagcacac ctgagttaag      60 ggggaacaa tgaaacaaat ccaatagaat ttttacagca tgtaaggag gcaggtttaa      120 aagccatgct ataaaaaga gaaaactgga aggcaggtac gccgtaccgg gc             172

<210> SEQ ID NO 15
<211> LENGTH: 157
<212> TYPE: DNA
<213> ORGANISM: Rattus sp.

<400> SEQUENCE: 15
ctgcctccca gtcttctctt ttctatagca tggctttaaa gcctgcctcc ttgacatgct      60
gtatatattc tattgtattt gtttcattgt cccacactta actcaggtgt gctaaaaata     120
aaagtaaatt ttaacagtca aaaaaaaaaa aaaaagg                             157

<210> SEQ ID NO 16
<211> LENGTH: 209
<212> TYPE: DNA
<213> ORGANISM: Rattus sp.

<400> SEQUENCE: 16
ccatacagtg cgcacttcga gtataacaac gcgagtgcaa tgctttacca tgatgcatga      60
agaaaactga ggagacagat cagctactat cgtagccatt acagctgaag agattcaaaa     120
ttggaaggca ctaactgatt gcgttaagac gcattctatc aaggttatca tagatgaaag     180
atcatagaaa ctggaaggca taaactgag                                      209

<210> SEQ ID NO 17
<211> LENGTH: 323
<212> TYPE: DNA
<213> ORGANISM: Rattus sp.
<220> FEATURE:
<221> NAME/KEY: misc_feature
<222> LOCATION: (280)..(320)
<223> OTHER INFORMATION: n

<400> SEQUENCE: 17
ccatacagtg cgcactgcga gactcacaac gcgagtgcaa cgcattacca tgatgcatga      60
agaaaactga ggagacagat cagctactat cgaagccatt acagctggag agatacttac     120
tgggaagccg ctaactgatt gcgttacgtc gaaatgtatc aaggttatca tagatgagag     180
```

```
atcatagaaa ctgctaggca tacactgagc attaagctta tcgacaccgt ggagctcgag      240
gtgagtccac gcaccagctg tgggaccgtg tagggactgn tacctacgag catggcgaga      300
tcataggcat agnntngtan tca                                              323
```

```
<210> SEQ ID NO 18
<211> LENGTH: 159
<212> TYPE: DNA
<213> ORGANISM: Rattus sp.
<220> FEATURE:
<221> NAME/KEY: misc_feature
<222> LOCATION: (60)..(60)
<223> OTHER INFORMATION: n

<400> SEQUENCE: 18
```

```
ctgcctccca gtcttctctt ttctatagca tggctttaaa gcctgcctcc ttgacatgcn       60
tgatatattc tattgtattt gtttcattgt cccacactta actcaggtgt gctaaaaata      120
aaagtaaatt ttaacagtca aaaaaaaaaa aaaaaagg                              159
```

```
<210> SEQ ID NO 19
<211> LENGTH: 162
<212> TYPE: DNA
<213> ORGANISM: Rattus sp.

<400> SEQUENCE: 19
```

```
cgacgaacct gcctcccagt cttctctttt ctatagcatg gctttaaagc ctgcctcctt       60
gacatgctgt atatattcta ttgtatttgt ttcattgtcc cacacttaac tcaggtgtgc      120
taaaaataaa agtaaatttt aacagtcaaa aaaaaaaaaa aa                         162
```

```
<210> SEQ ID NO 20
<211> LENGTH: 142
<212> TYPE: DNA
<213> ORGANISM: Rattus sp.
<220> FEATURE:
<221> NAME/KEY: misc_feature
<222> LOCATION: (50)..(50)
<223> OTHER INFORMATION: n

<400> SEQUENCE: 20
```

```
cttctctttt ctatagcatg gctttaaagc ctgcctcctt gacatgctgn atatattcta       60
ttgtatttgt ttcattgtcc cacacttaac tcaggtgtgc taaaaataaa agtaaatttt      120
aacagtcaaa aaaaaaaaaa aa                                               142
```

```
<210> SEQ ID NO 21
<211> LENGTH: 162
<212> TYPE: DNA
<213> ORGANISM: Rattus sp.
<220> FEATURE:
<221> NAME/KEY: misc_feature
<222> LOCATION: (68)..(68)
<223> OTHER INFORMATION: n

<400> SEQUENCE: 21
```

```
cgacgaccct gcctcccagt cttctctttt ctatagcatg gctttaaagc ctgcctcctt       60
gacatgcntg atatattcta ttggatttgt ttcattgtcc cacacttaac tcaggtgtgc      120
taaaaataaa agtaaatttt aacagtcaaa aaaaaaaaaa ag                         162
```

```
<210> SEQ ID NO 22
<211> LENGTH: 159
<212> TYPE: DNA
```

```
<213> ORGANISM: Rattus sp.

<400> SEQUENCE: 22
cgacgaacct gcctcccagt cttctctttt ctatagcatg gctttaaagc ctgcctcctt    60
gacatgctgt atatattcta ttgtatttgt ttcattgtcc cacacttaac tcaggtgtgc   120
taaaaataaa agtaaatttt aacagtcaaa aaaaaaaa                            159

<210> SEQ ID NO 23
<211> LENGTH: 163
<212> TYPE: DNA
<213> ORGANISM: Rattus sp.

<400> SEQUENCE: 23
ggtacgacga acctgcctcc cagtcttctc ttttctatag catggcttta aagcctgcct    60
ccttgacatg ctgtatatat tctattgtat ttgtttcatt gtcccacact taactcaggt   120
gtgctaaaaa taaagtaaa ttttaacagt caaaaaaaaa aaa                       163

<210> SEQ ID NO 24
<211> LENGTH: 106
<212> TYPE: DNA
<213> ORGANISM: Rattus sp.

<400> SEQUENCE: 24
gatctgagac ccactttgca gacatgtgca cagatgtgtt ccatttccct attttgctg     60 tagagaaaca agtaaatttt cttagagaat gaaaaaaaaa aaaaaa                   106

<210> SEQ ID NO 25
<211> LENGTH: 176
<212> TYPE: DNA
<213> ORGANISM: Rattus sp.

<400> SEQUENCE: 25
ctaattgcgc gcggccgcgg tacgacgacc ctgcgatctg agacccactt tgcagacatg    60
tgcacagatg tgttccattt ccctattttt gctgtagaga acaagtaaa ttttcttaga   120 gaatgaaaaa aaaaaaaaat agggcgcgcc tttaaaacgg ttccgatttt tgggcc       176

<210> SEQ ID NO 26
<211> LENGTH: 163
<212> TYPE: DNA
<213> ORGANISM: Rattus sp.
<220> FEATURE:
<221> NAME/KEY: misc_feature
<222> LOCATION: (70)..(70)
<223> OTHER INFORMATION: n

<400> SEQUENCE: 26
acgacgaccc tgcctcccag tcttctcttt tctatagcat ggctttaaag cctgcctcct    60
tgacatgctn gatatattct attggatttg tttcattgtc ccacacttaa ctcaggtgtg   120
ctaaaaataa aagtaaattt taacggtcaa aaaaaaaaa aaa                      163

<210> SEQ ID NO 27
<211> LENGTH: 109
<212> TYPE: DNA
<213> ORGANISM: Rattus sp.

<400> SEQUENCE: 27
gatctgagac ccactttgca gacatgtgca cagatgtgtt ccatttccct atttctgctg    60
tagagaaaca agtaaatttt cttagagaat gaaaaaaaaa aaaaaaaaa                109
```

<210> SEQ ID NO 28
<211> LENGTH: 121
<212> TYPE: DNA
<213> ORGANISM: Rattus sp.

<400> SEQUENCE: 28

| ggcgacgtac | ctgcgatctg | agacccactt | tgcagacatg | tgcacagatg | tgttccattt | 60 |
| ccctatttct | gctgtagaga | aacaagtaaa | ttttcttaga | gaatgaaaaa | aaaaaaaaaa | 120 |
| a | | | | | | 121 |

<210> SEQ ID NO 29
<211> LENGTH: 127
<212> TYPE: DNA
<213> ORGANISM: Rattus sp.

<400> SEQUENCE: 29

| tttttttttt | tttttttttaa | ttctttaaaa | aaatttactg | gtttcttac | agcaaaaata | 60 |
| gggaaatgga | acacatttgg | gcacatgttt | gcaaaggggg | tctaaaatcg | caggtacgtg | 120 |
| gtaccgg | | | | | | 127 |

<210> SEQ ID NO 30
<211> LENGTH: 225
<212> TYPE: DNA
<213> ORGANISM: Rattus sp.

<400> SEQUENCE: 30

| ggacgacgta | cctgcatgat | tggttccacc | taataagcaa | ggaaagaata | cttgaccttc | 60 |
| aaactcatcc | agtgttggag | atctccataa | taccttccat | cctttggacc | atgccttgga | 120 |
| tggagacaga | cactactgga | gaaggggct | gcttacccca | gagaatac | tacctaaatg | 180 |
| ctgctacatc | agagactatc | catgacgagc | atctcatata | aggat | | 225 |

<210> SEQ ID NO 31
<211> LENGTH: 451
<212> TYPE: DNA
<213> ORGANISM: Rattus sp.

<400> SEQUENCE: 31

| atgattggtt | ccacctaata | agcaaggaaa | gaatacttga | ccttcaaact | catccagtgt | 60 |
| tggagatctc | cataatacct | tccatccttt | ggcccatgcc | ttggatggag | acagacacta | 120 |
| ctggagaaag | gggctgcttt | ccccagagag | aatactacct | aaatgctggt | tcatcagaga | 180 |
| atatccatga | agagcatctc | agataaggat | tgaaaagggg | gtgctgggta | gagtatagta | 240 |
| gaggaggact | tgttaagttc | actgatgctg | ggaagaaact | tcctgtaatg | cctacagcat | 300 |
| tccatgggcc | atagagtacc | aatatggtat | gcctctttac | agagtcaatc | tcagccccca | 360 |
| gaaagtgtat | tctactgtgc | tcaggcccaa | aggcagtgtg | gtggtcaaag | ggcaactggc | 420 |
| ctcctgaacc | cagtagagcc | ttgcaaagtg | c | | | 451 |

<210> SEQ ID NO 32
<211> LENGTH: 505
<212> TYPE: DNA
<213> ORGANISM: Rattus sp.

<400> SEQUENCE: 32

| ggtacgacga | ccctgcatga | ttggttccac | ctaataagca | aggaaagaat | acttgacctt | 60 |

```
caaactcatc cagtgttgga gatctccata ataccttcca tcctttggcc catgccttgg      120
atggagacag acactactgg agaaagggc tgctttcccc agagagaata ctacctaaat      180
gctggttcat cagagaatat ccatgaagag catctcagat aaggattgaa aaggggtgc      240 tgggtagagt atagtagagg aggacttgtt aagttcactg atgctgggaa gaaacttcct      300
gtaatgccta cagcattcca tgggccatag agtaccaata tggtatgcct ctttacagag      360
tcaatctcag cccccagaaa gtgtattcta ctgtgctcag gcccaaaggc agtgtggtgg      420
tcaaagggca actggcctcc tgaacccaga agagccttgc aaagtgctgg cagtcaggga      480
ggtgccatac atgattcttg tcttt                                           505

<210> SEQ ID NO 33
<211> LENGTH: 402
<212> TYPE: DNA
<213> ORGANISM: Rattus sp.

<400> SEQUENCE: 33
ctttaatagc catggcctta tagacggtgg ccacgcggcc tgcacaggct gtgtgcatta      60 ggcccttag ccttgttta cacttgcagc acctacttct gctggggttc aactcagtgc      120
acagcacttg cttagcctat gtgagaccct gcacttaatg cccagcacca caaaaaagaa      180 acaaatacc tctattttaa gatgatgctt aagaattatc ctaattcaaa gcagcaaaaa      240
tataacttta caattataaa agagctaaac cagaaccac aatcagtgtc taagtgtgaa      300
tctaataaac actgcctctc tgcagctctt accagctttc tggttgtta cacacactca      360 cacacgcgca cacacacaca cacgcgctcc ctcctactga gg                        402

<210> SEQ ID NO 34
<211> LENGTH: 294
<212> TYPE: DNA
<213> ORGANISM: Rattus sp.

<400> SEQUENCE: 34
tttttttttt tttttttttt tttgggcttt tcggcggttt ttttttttgga aggaaaccca      60 tgggggggg tttgggggggg gggccccct aaaaaataac ctggggttca aaggggcccc       120
aaaccttact ggaaaggccg ggggacaaaa ccatggtttc aaccggacca cttgttacca      180
aggtgggggc cccaagaggg cttcagggg ggggggggc cctttaaaga aagcgggaac       240
tggggggggc aaaccctggg cccaccttg accccttga aaaaaaaaa aaaa              294

<210> SEQ ID NO 35
<211> LENGTH: 286
<212> TYPE: DNA
<213> ORGANISM: Rattus sp.

<400> SEQUENCE: 35
ctcccagtct tctcttttct atagcatggc tttaaagcct gcctccttga catgctgtat      60
atattctatt gtatttgttt cattgtccca cacttaactc aggtgtgcta aaataaaag      120 taaatttaa cagtcaaaaa aaaaaaaaaa aaaaaaaaaa aaaaaaaaaa aaaagggaa      180 aaaaaaaa aaagggcccc ccctttaaaa gggtcccaaa ttttgggccc ccttttgaa       240 aaactttttt ttaaaaccc ccggggggat taaattttttt tggggg                   286

<210> SEQ ID NO 36
<211> LENGTH: 203
<212> TYPE: DNA
<213> ORGANISM: Rattus sp.
```

<400> SEQUENCE: 36

| | | | | | |
|---|---|---|---|---|---|
| cattagtgga | gaggtgtgca | gtgggactgt | gagtgcaact | actttagtgc | agatgtgtgc | 60 |
| agtgggcctg | tgagtgcaga | atcattagtg | cagatgtgtg | tagtgggcct | gtgagtgcag | 120 |
| gcacattagt | gcagaggtgt | gaagtgggcc | tgtcagtgca | ggcacattag | tggagaggtg | 180 |
| tgaagtgggc | ctgtgagtgc | agg | | | | 203 |

<210> SEQ ID NO 37
<211> LENGTH: 147
<212> TYPE: DNA
<213> ORGANISM: Rattus sp.

<400> SEQUENCE: 37

| | | | | | |
|---|---|---|---|---|---|
| caagcttttt | tttttttttt | tttttttttt | ggttttttggc | ggttttatttt | ttggcaggaa | 60 |
| accctggggg | gggggtttgg | tggggggggc | cccctaaaaa | ataccccgga | ggtcaagggg | 120 |
| gttcaaaact | ttttttaaaa | ggctggg | | | | 147 |

<210> SEQ ID NO 38
<211> LENGTH: 360
<212> TYPE: DNA
<213> ORGANISM: Rattus sp.

<400> SEQUENCE: 38

| | | | | | |
|---|---|---|---|---|---|
| cctttttctc | cccccatgga | agcgaagact | ctgaacacag | agtggtctgt | attgtggggt | 60 |
| tggggttgc | ctccctatcg | ctgggtagcc | tgaagcgtga | gtccagacta | gacgtgtgag | 120 |
| gggaatgatc | tatgccgtgc | tcgaatagct | gggaggtccc | tttgtccctg | agaccagaac | 180 |
| gggaaatggt | tatccgcact | gggaagctgc | ctctcaagta | gaaactgcca | gataactttc | 240 |
| tgggctggga | attctgtcaa | cttaactgaa | gcctggcagc | atccgcccca | aagcaattta | 300 |
| aattagggag | agtcctgggc | tgtcccaggt | gcccttaggt | aaacttgaca | gactgctgag | 360 |

<210> SEQ ID NO 39
<211> LENGTH: 151
<212> TYPE: DNA
<213> ORGANISM: Rattus sp.

<400> SEQUENCE: 39

| | | | | | |
|---|---|---|---|---|---|
| ctcccagtct | tctcttttct | atagcatggc | tttaaagcct | gcctccttga | catgctgtat | 60 |
| atattctatt | gtatttgttt | cattgtccca | cacttaactc | aggtgtgcta | aaaataaaag | 120 |
| taaattttaa | cagtcaaaaa | aaaaaaaaaa | a | | | 151 |

<210> SEQ ID NO 40
<211> LENGTH: 163
<212> TYPE: DNA
<213> ORGANISM: Rattus sp.

<400> SEQUENCE: 40

| | | | | | |
|---|---|---|---|---|---|
| cgacgaccct | gcctcccagt | cttctctttt | ctatagcatg | gctttaaagc | ctgcctcctt | 60 |
| gacatgctgt | atatattcta | ttgtatttgt | tcattgtcc | cacacttaac | tcaggtgtgc | 120 |
| taaaaataaa | agtaaatttt | aacagtcaaa | aaaaaaaaaa | aaa | | 163 |

<210> SEQ ID NO 41
<211> LENGTH: 77
<212> TYPE: DNA
<213> ORGANISM: Rattus sp.

```
<400> SEQUENCE: 41
gatgtgttcc acttccctat ttctgctgta gagaaacaag taaattttct tagagaatga      60
aaaaaaaaaa aaaaagg                                                     77

<210> SEQ ID NO 42
<211> LENGTH: 204
<212> TYPE: DNA
<213> ORGANISM: Rattus sp.

<400> SEQUENCE: 42
cctcagtagg agggagcgcg tgtgtgtgtg tgtgcgcgtg tgtgagtgtg tgtaacaacc      60
cagaaagctg gtaagagctg cagagaggca gtgtttatta gattcacact tagacactga     120
ttgtgggttc tggtttagct cttttataag tgtaaagcta tattttgct gctttggaat      180 aggataattc ttaagcatca tctt                                            204

<210> SEQ ID NO 43
<211> LENGTH: 498
<212> TYPE: DNA
<213> ORGANISM: Rattus sp.

<400> SEQUENCE: 43
ccatttgagg gaagatacag tgttagatga agcagaaacc aatttttattg ttagtgttta     60 atcttggtgc agatttataa gttttagagt agcccagaga ctaaaagtga atacttagca    120
aatggatagc cagtgttcta tataggaatc attgcttttc agagggctta aagtttaagt    180
agaaaatata tactcaagaa ggcgataaaa gctgatgaga aagtgagtta gcagaaccca    240
aagccgtgct gggccgcggt gactcattag cagaggagga gggagggca gtatattcct     300 gggatactct ctccagaccc agcctggctt ctgacatcat ccacctgtgc cctcaaaacc    360
gtcttagtct gttctgcaac tcttaagtga catacctaac tcagctcatg gctaaggaaa    420
aaaaattaaa gttgtcctgg tgattaaact ctggacctcc cacatctaag tcccgagttg    480
acaaactgca tccccagc                                                  498

<210> SEQ ID NO 44
<211> LENGTH: 400
<212> TYPE: DNA
<213> ORGANISM: Rattus sp.

<400> SEQUENCE: 44
ctttaatagc catggcctta tagacggtgg ccacgcgacc tgcacaggct gtgtgcatta     60 ggcccttttag ccttgtttta cacttgcagc acctacttct gctggagctc aactcagtgc   120
acagcacttg cttagcctat gagagaccct gcacttaatg cccagcacca caaaaaagaa    180
acaaaatacc tctatttttaa gatgatgctt aagaattatc ctattacaaa gcagcaaaaa   240
tataacttta caattataaa agagctaaac cagaacccac aatcagtgtc taagtgtgaa    300
tctaataaac actgcctctc tgcagctctt accagctttc tggattgtta cacacactca   360
cacacgcgca cacacacaca cgcgctcccct cctactgagg                          400

<210> SEQ ID NO 45
<211> LENGTH: 209
<212> TYPE: DNA
<213> ORGANISM: Rattus sp.

<400> SEQUENCE: 45
cctcagtagg agggagcgcg tgtgtgtgtg tgtgcgcgtg tgtgagtgtg tgtaacaacc      60
```

```
cagaaagctg gtaagagctg cagagaggca gtgtttatta gattcacact tagacactga    120
ttgtgggttc tggtttagct cttttataat tgtaaagtta tattttttgct gctttgtaat    180
```

```
cagaaagctg gtaagagctg cagagaggca gtgtttatta gattcacact tagacactga    120
ttgtgggttc tggtttagct cttttataat tgtaaagtta tattttttgct gctttgtaat    180 aggataattc ttaagcatca tcttaaaat                                       209
```

<210> SEQ ID NO 46
<211> LENGTH: 403
<212> TYPE: DNA
<213> ORGANISM: Rattus sp.
<220> FEATURE:
<221> NAME/KEY: misc_feature
<222> LOCATION: (339)..(344)
<223> OTHER INFORMATION: n

<400> SEQUENCE: 46

```
ctttaatagt catggcctta tagacggtgg ccacgcggcc tgcacaggct gtgtgcatta    60
ggccctttag ccttgttttta cacttgcagc acctacttct gctggggttc aactcagtgc    120
acagcacttg cttagcctat gtgagaccct gcacttaatg cccagcacca caaaaaagaa    180
acaaaatacc tctattttaa gatgatgctt aagaattat cctattacaa agcagcaaaa    240
atataacttt acaattataa aagagctaaa ccagaaccca caatcagtgt ctaagtgtga    300
atctaataaa cactgcctct ctgcagctct taccagctnt ctgngttgtt acacacactc    360
acacacgcgc acacacacac acacgcgctc cctcctactg agg                     403
```

<210> SEQ ID NO 47
<211> LENGTH: 404
<212> TYPE: DNA
<213> ORGANISM: Rattus sp.
<220> FEATURE:
<221> NAME/KEY: misc_feature
<222> LOCATION: (386)..(386)
<223> OTHER INFORMATION: n

<400> SEQUENCE: 47

```
cctcagtagg agggagcgcg tgtgtgtgtg tgtgcgcgtg tgtgagtgtg tgtaacaacc    60
cagaaagctg gtaagagctg cagagaggca gtgtttatta gattcacact tagacactga    120
ttgtgggttc tggtttagct cttttataat tgtaaagtta tattttttgct gctttgtaat    180 aggataattc ttaagcatca tcttaaaata gagggtattt tgtttctttt ttgtggtgct    240
gggcattaag tgcagggtct cacataggct aagcaagtgc tgtgcactga gttgaacccc    300
agcagaagta ggtgctgcaa gtgtaaaaca aggctaaagg gctaatgcac actagctgtg    360
caggccgcgt ggtcatcgtc tataangcca tggctaataa agtt                    404
```

<210> SEQ ID NO 48
<211> LENGTH: 403
<212> TYPE: DNA
<213> ORGANISM: Rattus sp.

<400> SEQUENCE: 48

```
ctttaatagc catggcctta tagacggtgg ccacgcggcc tgcacaggct gtgtgcatta    60
ggccctttag ccttgttttta cacttgcagc acctacttct gctggggttc aactcagtgc    120
acagcacttg cttagcctat gtgagaccct gcacttaatg cccagcacca caaaaaagaa    180
acaaaatacc tctattttaa gatgatgctt aagattaat cctattacaa agcagcaaaa    240
atataacttt acaattataa aagagctaaa ccagaaccca caatcagtgt ctaagtgtga    300
atctaataaa cactgcctct ctgcagctct taccagcttt ctgggttgtt acacacactc    360
```

| acacacgcgc acacacacac acacgcgctc cctcctactg agg | 403 |

<210> SEQ ID NO 49
<211> LENGTH: 433
<212> TYPE: DNA
<213> ORGANISM: Rattus sp.

<400> SEQUENCE: 49

| ctggcacctc attgccaaga ctgtccattc caatatttag ttcgccaagc ttttgaatag | 60 |
| acctattaag gaattgctca gtaagattct gctgctgatc aggaccgtcc tcttggttca | 120 |
| cacctccttc aagtaacatc tgctggtata tctgccgctg ttgctccttc tgttcgagat | 180 |
| gctgctgata gcgcaatctt tgcctataat attcttgaaa ttgttcagta gaatctcgaa | 240 |
| gctcgttttt ttcttgttgt ttagctggaa ctgggttctg tgctccattt gcaggctctt | 300 |
| tctctaaccc cgaaccctgg cacatgggtt caatgctcac aggctgctgg gtctcaacag | 360 |
| gggtatcact tcgctcagga gattcttcat agatactatg cactctgta ttctcaagca | 420 |
| gaagacttct gct | 433 |

<210> SEQ ID NO 50
<211> LENGTH: 262
<212> TYPE: DNA
<213> ORGANISM: Rattus sp.

<400> SEQUENCE: 50

| cgaggaccag cacagcagtg aggaggagga agaagaggaa gaggaggagg agagtgaaga | 60 |
| cggggaggag gaggaggaca tcaccagtgc cgagtcagag agcagtgagg aggaggaagg | 120 |
| cggccccggg gacggccaga acaccacccg gcagcagcag ctagaatggg actactccac | 180 |
| actcagctac taaacacgcg ctcgcccagc acctgctctc cagactctcc cagccatctt | 240 |
| ccagccccac gggtccacga tg | 262 |

<210> SEQ ID NO 51
<211> LENGTH: 262
<212> TYPE: DNA
<213> ORGANISM: Rattus sp.

<400> SEQUENCE: 51

| cgaggaccag cacagcagtg aggaggagga agaagaggaa gaggaggagg agagtgaaga | 60 |
| cggggaggag gaggaggaca tcaccagtgc cgagtcagag agcagtgagg aggaggaagg | 120 |
| cggccccggg gacggccaga acaccacccg gcagcagcag ctagaatggg actactccac | 180 |
| actcagctac taaacacgcg ctcgcccagc acctgctctc cagactctcc cagccatctt | 240 |
| ccagccccac gggtccacga tg | 262 |

<210> SEQ ID NO 52
<211> LENGTH: 388
<212> TYPE: DNA
<213> ORGANISM: Rattus sp.

<400> SEQUENCE: 52

| cttcttgatg atgcgtaaca tgttctggta ggagttccaa gtgttgtgag ccaccaggag | 60 |
| atcatggctg ccgggcagca gcttgatgag ggcagagaca gaaccggagc ccacggaagg | 120 |
| cttggtgttg gtcttattca gggctggctc taggtcttcc agatctccag agatctgcag | 180 |
| caggaggaac cccaagggtt tgatgttgaa cctcccagtt gggaaggtta aacggccttc | 240 |
| atagctgtcc tccaggcctt tcagctgcaa gagggtcagc cgcacctggt gccagtatgg | 300 |

```
cgagtccggg ctaagctcca tttccctctg catccactcc aggttggcct ccaggaagct    360
cttgagcttc tcacagtagc cgacttcg                                       388
```

<210> SEQ ID NO 53
<211> LENGTH: 164
<212> TYPE: DNA
<213> ORGANISM: Rattus sp.

<400> SEQUENCE: 53

```
cgacgaccct gcctcccagt cttctctttt ctatagcatg gctttaaagc ctgcctcctt    60
gacatgctgt atatattcta ttgtatttgt ttcattgtcc cacacttaac tcaggtgtgc    120
taaaaataaa agtaaatttt aacagtcaaa aaaaaaaaa aaag                      164
```

<210> SEQ ID NO 54
<211> LENGTH: 150
<212> TYPE: DNA
<213> ORGANISM: Rattus sp.

<400> SEQUENCE: 54

```
gcggccgccc gggcaggtcg ctccgcgtgt ttggtggggt tacttttccc acttcgcgac    60
gtttgccctg ggcagctcag aagtgttacg tgttgcaccc tccccaaggc tgtcaacagc    120
agaaagcaac ccctggcgct agcccgtatt                                     150
```

<210> SEQ ID NO 55
<211> LENGTH: 99
<212> TYPE: DNA
<213> ORGANISM: Rattus sp.

<400> SEQUENCE: 55

```
catgaaaata acggagcctc gaaagctata acagaccttt tgtacataga gaaatggcat    60
atttattaaa taagttggat ttgtaaaaaa aaaaaaaaa                           99
```

<210> SEQ ID NO 56
<211> LENGTH: 357
<212> TYPE: DNA
<213> ORGANISM: Rattus sp.

<400> SEQUENCE: 56

```
ggaggcggag gatgagtgcc aacaccctcg actgcctgct ctaggcgatg aggttataga    60
aagggaagag tttcaggata tggctgtgtg tgtaggggc atgaaggcag gttataaaca    120
aatatatccc agctgcctaa ggagttggtt gctgtcctca ctcttaacaa tccagtggga    180
tctagtgatc aacatcagtt tggagactct aatcttcatg ctcatgtatt catcctgaca    240
ttttaacttg ctattctgtg tgaccgaata cttgttatac ctagaatacg acctaagtgc    300
cttctgattt ctcatgattt cttttcaaac agggtctaag tcatctactt gcatttt      357
```

<210> SEQ ID NO 57
<211> LENGTH: 409
<212> TYPE: DNA
<213> ORGANISM: Rattus sp.

<400> SEQUENCE: 57

```
ggaggcggag gatgagtgcc aacaccctcg actgcctgct ctaggcgatg aggttataga    60
aagggaagag tttcaggata tggctgtgtg tgtaggggc atgaaggcag gttataaaca    120
aatatatccc agctgcctaa ggagttggtt gctgtcctca ctcttaacaa tccagtggga    180
```

| | |
|---|---:|
| tctagtgatc aacatcagtt tggagactct aatcttcatg ctcatgtatt catcctgaca | 240 |
| ttttaacttg ctattctgtg tgaccgaata cttgttatac ctagaatacg acctaagtgc | 300 |
| cttctgattt ctcatgattt cttttcaaac agggtctaag tcatctactt gcattttgcc | 360 |
| agaagctctc cggaaaacaa agcatacaaa atctacttgc tatttctct | 409 |

<210> SEQ ID NO 58
<211> LENGTH: 454
<212> TYPE: DNA
<213> ORGANISM: Rattus sp.

<400> SEQUENCE: 58

| | |
|---|---:|
| caaggctaca ggcctaggcc tagggataca acagcgaagg aaccactctg gtctcagccc | 60 |
| aagcagcaca gctggagcgc agctctcttc tcgctttcat ctttacggag acttgggtgg | 120 |
| aagggcgggc cctttgacat ctttgtcgtc ggccttggac tcagagatgg ccagcttatt | 180 |
| ctgcagggag cacagcagct ggaggtagct ctggttcctc tgcagcttct cctgctcctg | 240 |
| tcctgcttgc tgcttcaagg tttcaagttc ctggtgagaa ccatcaagct tctccagagc | 300 |
| tctcttccgg cgtctcttga cctcagcaga aatctttgtc agattctgca aacgcttctg | 360 |
| ctgcagcacc cactgcttct gagctaactg cagtttctcc tcaaggactc gcttcttagc | 420 |
| ctcaagttgc tcaaaagcct tctgaagctc ggcg | 454 |

<210> SEQ ID NO 59
<211> LENGTH: 122
<212> TYPE: DNA
<213> ORGANISM: Rattus sp.

<400> SEQUENCE: 59

| | |
|---|---:|
| tttttttttt tttttttttt tttcccttg ggaggttttt ttcaaaaacc ccggaaaaat | 60 |
| tggccctggt tccggggggt ttttgaaaaa ataaaaacgg gaactaaccg ggggggggga | 120 |
| aa | 122 |

<210> SEQ ID NO 60
<211> LENGTH: 122
<212> TYPE: DNA
<213> ORGANISM: Rattus sp.

<400> SEQUENCE: 60

| | |
|---|---:|
| tttttttttt tttttttttt tttccctttg ggaggttatt ttcaaaaagc ccggaaaaat | 60 |
| tggccctggt ttcggggggt ttttgaaaaa ccaaaaacgg gaaccaaccg ggggggggga | 120 |
| aa | 122 |

<210> SEQ ID NO 61
<211> LENGTH: 671
<212> TYPE: DNA
<213> ORGANISM: Rattus sp.
<220> FEATURE:
<221> NAME/KEY: misc_feature
<222> LOCATION: (511)..(666)
<223> OTHER INFORMATION: n

<400> SEQUENCE: 61

| | |
|---|---:|
| ggagagaatg gaggaggcgg tcatgtcaat tctgcacaac ttagagatga agaacactga | 60 |
| gatccatgag aacaaccgta aggtgaagaa ggagattacc ttctctagaa acctgctcag | 120 |
| ccagctcctg atgagaaaca catgtaggaa gaagttgctc ccactgaagc aggagagcaa | 180 |
| ggagggacat cttgagtgtg caatgaacca gaaatatttg gttgacttca acaagaaaga | 240 |

```
taaagaccag caacctccag acccagcatc atcaggtctc agaaagtgca agagagctgg    300
aattggacac acagcagtaa gagagcttcc tgaagaataa gttgctttct cacgagtccc    360
tgatgacaaa catcctgaac gaaaacatca cttgagagac aacttggggg accgcctttc    420
attatgtgtg ctagaggaga aacagcaata catctgtgct tctaaatgtt cgttaagaat    480
atgctgttta gaaatatttt tgttatgatt ntaaatgagg tntcttttg tggttcatat    540 ttatatggtc ttggtactat ntttactttc anatatttt aaatatttnt attcattcat    600
tntaaatcct gttggtggaa aatgattcaa tatgaataaa tatgtgttta ttcttgaaaa    660
aaaaanaaaa a                                                        671

<210> SEQ ID NO 62
<211> LENGTH: 652
<212> TYPE: DNA
<213> ORGANISM: Rattus sp.

<400> SEQUENCE: 62
gaggaggcgg tcatgtcaat tctgcacaac ttagagatgg agaacactga ggtccatgag     60
aacaaccata atctgaagaa ggagatacct tctctagaaa cctgctcagc cagctcctga    120
tggagaacac atgtaggaag aagttggtcc cactgaagca ggagagcaag gaggtacatc    180
ttgattgtgc actgaaccag aaatatttgg ttgacttcaa caagaaagat aaagaccatc    240
aacggccaga accagcatta tcaggtctca gaaagtgcaa agagagctgga attggacaca    300 cagcagtaag agagcttcct gaagaataag ttgctttctc aggagtccct gatgaccaac    360
atcctgaatg aaaacagcac ttgagagaca acttggggga ccgcctttca ttatgtgtgc    420
tagaggagaa acagcaatac gtctgtgctt ctaaatgttc gttaagaata tgcttttaga    480 aatattttg ttatgattta tttgaagttt cttttggt ggttcatatt tatatgttct    540
tgttactatt tttactttc aatattttta atattttat tcatttaatc ctgttttgtt    600 ggaaaatgt atttgttatg aataaaaatt gaattctaaa aaaaaaaaaa aa            652

<210> SEQ ID NO 63
<211> LENGTH: 662
<212> TYPE: DNA
<213> ORGANISM: Rattus sp.
<220> FEATURE:
<221> NAME/KEY: misc_feature
<222> LOCATION: (561)..(614)
<223> OTHER INFORMATION: n

<400> SEQUENCE: 63
ggagagaatg gaggaggcgg tcatgtcaat tctgcacaac ttagagatgg agaacactga     60
ggtccatgag aacaaccata atctgaagaa ggagattacc ttctctagaa acctgctcag    120
ccagctcctg atggagaaca catgtaggaa gaagttggtc ccactgaagc aggagagcaa    180
ggaggtacat cttgattgtg cactgaacca gaaatatttg gttgacttca acaagaaaga    240
taaagaccat caacggccag aaccagcatt atcaggtctc agaaagtgca agagagctgg    300
aattggacac acagcagtaa gagagcttcc tgaagaataa gttgctttct caggagtccc    360
tgatgaccaa catcctgaat gaaaacagca cttgagagac aacttggggg accgcctttc    420
attatgtgtg ctagaggaga aacagcaata cgtctgtgct tctaaatgtt cgttaagaat    480
atgcttttag aaatatttt gttatgattt atttgaagtt ttcttttgg tggttcatat    540 ttatatgttc ttggtactat ntttactttc aaatatttta aatatttat tcatntaatc    600
```

```
ctgntttggt gganaaatgt attttgtatg aataaaaaat ggattctaaa aaaaaaaaaa       660
aa                                                                     662

<210> SEQ ID NO 64
<211> LENGTH: 650
<212> TYPE: DNA
<213> ORGANISM: Rattus sp.
<220> FEATURE:
<221> NAME/KEY: misc_feature
<222> LOCATION: (217)..(643)
<223> OTHER INFORMATION: n

<400> SEQUENCE: 64 tgttttttt ttttttttt tcttgctata gagacttgac tctttgctca acaccatgcc         60
ccacgtttgg gagaggaaga tggcaaagac tgaaagcacg atgccggggg tatattgcaa      120
caccatcaaa acagagccca tagctgcctg ccccccggta tagttagaga caggccgtgt      180
gttacctcta caattaaaac gtacttgtag acttggnggt aagggaccct ccacctattt      240
caaattctgc cagaagacag aaggatgttc actcaccaat caagaaccct tggcttccta     300
ctcctgactt tgtcgctgga ngctggcta cagtaccaaa cctatgtaga actatcatct      360
tcagtcgagc ctcggtgtaa ttggcagaga ttctgagtca actaccatgc agagatctcc     420
gaccctgtct agagacattt actagaagct gtcttacagc cctgtctttg aggcgagaca     480
cataccaaat gtatgttccc ccaagaggag acacactcta tcttcagata tctgtgaacc     540
cannnnnnaa aaaaaaaacc agcccgcccc ggggggcgca ccttgaatga cacaggggac     600
atggntggct gccccgtata gaaagcccca gcttnaacac agnaaatgtg                650

<210> SEQ ID NO 65
<211> LENGTH: 484
<212> TYPE: DNA
<213> ORGANISM: Rattus sp.

<400> SEQUENCE: 65
cagaagcagt tagaagtcat caatgctatt gtggacccca gcatgaaccc cgacctactg      60
atgggaaaca gggctcctgc agggtccgtt cagccaggac ttgggaaagc ccggccagca    120
gctcagagct cagcttctcc tgcctcggtg acaccttgc tgccagccat gcctctcagg     180
agcttcccac aacgggcaaa ctgcgggccc cccggcctcc cggagcctgc cttccttcct    240
gatgctgaga ggtttctgat ctaagctgtg aggcgggcaa ggccagcctt cttgtgcgcg    300
tgtgtcctgt gcatcaccca tcccatggcc cacctgcctg gctcaggcag ttctgtgaaa    360
accccacatg tgccataacc catggacggg tgcctcccat tcccaggcct ctcctcagcc    420
agcacccgaa ccacttcatc cagctcatgg ctaccccatc cccacagacc tcctagccca    480
gccc                                                                 484

<210> SEQ ID NO 66
<211> LENGTH: 132
<212> TYPE: DNA
<213> ORGANISM: Rattus sp.

<400> SEQUENCE: 66
tttttttttt ttttttttt ccaaaaaaac agtaaaattt aatttctaaa gagggttaaa      60
attttccttt ccccccaaaa aattagggag attccagtgt taaaaatgtc ctcaaaattt    120
ttatgaccct aa                                                        132
```

<210> SEQ ID NO 67
<211> LENGTH: 172
<212> TYPE: DNA
<213> ORGANISM: Rattus sp.

<400> SEQUENCE: 67
gagaccaaga agcctggcat gaacttgcag aactttatat caatgagcat gactatgcca      60
aagcagcctt atgcttagag gagctgatga tgacaaatcc acataaccac ttgtactgtc     120
aacaggacgc agaggtcaaa tacacccaag gtggacttga aaacctggtg ct             172

<210> SEQ ID NO 68
<211> LENGTH: 382
<212> TYPE: DNA
<213> ORGANISM: Rattus sp.

<400> SEQUENCE: 68
aggttgattc ctagcagcca catggagcca aattgtctgt aactctagtt ccagggtctc      60
caacatctac ccttgaccat ggctggcact gtgtgtatgt ggtgcacaaa cacacgaagg     120
cagaacacct aaaaggggta tatgtgctat catttaagtg tctcttaaat gaaaagcctt     180
caaccaggat ttcatcatta gaaatagaat tgatgtccac cctgtgtcat gggaactgag     240
aggaagggca gtataaatct gagaggttcc tttgtgtggt ggaccccgaa gaagaaagcc     300
ccatggctga acagctgttg tctcctccta ccccacagct ttccctaata aagggattgt     360
tattttgaaa aaaaaaaaa aa                                               382

<210> SEQ ID NO 69
<211> LENGTH: 53
<212> TYPE: DNA
<213> ORGANISM: Rattus sp.

<400> SEQUENCE: 69
cttctctaac atgtcggtgg gcgtcacatc agtgttgacc tactcttccg tct             53

<210> SEQ ID NO 70
<211> LENGTH: 226
<212> TYPE: DNA
<213> ORGANISM: Rattus sp.

<400> SEQUENCE: 70
caggaggccc caagagctgc aggctagtgg gtccaggcta aggacttggg aagtggggtt      60
cagctcaggc ttggctgcag atgttagatg cagagacttc tgacctgtct aacaattaga     120
cctgttactg ccagtgtagg gacagatggt ttctttgact tcaagaagcc cattagtgga     180
aagacatctg acttggtatg ttactaagac agcaataacc ctgtag                    226

<210> SEQ ID NO 71
<211> LENGTH: 434
<212> TYPE: DNA
<213> ORGANISM: Rattus sp.

<400> SEQUENCE: 71
tggagctaat tgcgcgcggc cgcggtacga cgaacctgcg cctattagaa tgagtggaat      60
gcctccatcc ctcaatcgtc tgaagtgatc tgttagctaa gagcatggct cccaggggcc     120
cgtcctcagc cacttgtact cctgggctag ccttgtcata agatgccacc tggacactga     180
tggagtattg gagcagcagg cctggctcct gacctaaact gacagctcag actctgcagg     240
agtctgctgg aaatccaaca tcttactcaa caactgccgg ccagatgggc gtgggcgagg     300

| | |
|---|---|
| gtgggccaag acagggtgcc ttatactttg ttctagcaca ttccaaggta tttcagggcg | 360 |
| tcagcacctg gaatcccata tgtcaaagcc agtattaaag caagtttatg cattcctcga | 420 |
| aaaaaaaaaa aaaa | 434 |

<210> SEQ ID NO 72
<211> LENGTH: 569
<212> TYPE: DNA
<213> ORGANISM: Rattus sp.

<400> SEQUENCE: 72

| | |
|---|---|
| agctaattgc gcgcggccgc ggtacgacga acctgcacct ctgtcttctg cccccctccc | 60 |
| ttggacacat tcacacctac ctctaggaga gattggggat accttttagct ctctgaccga | 120 |
| ggaccaagcc tctgactcag acctgtatat ggcaccaagt tacaacccct tccaaaaggc | 180 |
| tcttcccagg ggagcacttg gcattttctg gcagacccca ttatcccttt cccaatgccc | 240 |
| tctctctgac tttgagcatc aggccagact gcctgagatc tggtgcctgc acagtgcct | 300 |
| ggccagggt gaggctttgg ttaccttctg ttgtatttgt gtggatagat gggcagctaa | 360 |
| caattgtaac aggtcctagg gtcagatgtg atggtctca tacagtggct tctaatggag | 420 |
| aatgtatctg aacccatatc aaatcacctc actgtatttt tctcttccct aacctgttaa | 480 |
| ctagccattg ttgtaggggg cttttgcaca gtgcctcact gtctcacatg ctaagtaaag | 540 |
| gaactcctgc tttcaaaaaa aaaaaaaaa | 569 |

<210> SEQ ID NO 73
<211> LENGTH: 552
<212> TYPE: DNA
<213> ORGANISM: Rattus sp.

<400> SEQUENCE: 73

| | |
|---|---|
| acctctgtct tctgccccc tcccttggac acattcacac ctacctctag gagagattgg | 60 |
| ggataccttt agctctctga ccgaggacca agcctctgac tcagacctgt atatggcacc | 120 |
| aagttacaac cctttccaaa aggctcttcc caggggagca cttggcattt tctggcagac | 180 |
| cccattatcc ctttcccaat gccctctctc tgactttgag catcaggcca gactgcctga | 240 |
| gatctggtgc ctgccacagt gcctggccag gggtgaggct ttggttacct tctgttgtat | 300 |
| ttgtgtggat agatgggcag ctaacaattg taacaggtcc tagggtcaga tgtggatggt | 360 |
| ctcatacagt ggcttctaat ggagaatgta tctgaaccca tatcaaatca cctcactgta | 420 |
| tttttctctt ccctaacctg ttaactagcc attgttgtag ggggcttttg cacagtgcct | 480 |
| cactgtctca catgctaagt aaaggaactc ctgctttcaa aaaaaaaaa aaagggccc | 540 |
| cccttttaaac gg | 552 |

<210> SEQ ID NO 74
<211> LENGTH: 188
<212> TYPE: DNA
<213> ORGANISM: Rattus sp.

<400> SEQUENCE: 74

| | |
|---|---|
| tttttttttt tttttttttt tttttttcat gggaaaaaaa aagggtttta aaaatggct | 60 |
| tgaaacccgg ggggggggg ccaaaacccct ccttttttaa taaaccttta ccgaagaagg | 120 |
| gttttcaaaa ggggggggg ggggggggcc cccctcccgc cctttttaggt ttggggggg | 180 |
| gggggaaa | 188 |

<210> SEQ ID NO 75
<211> LENGTH: 182
<212> TYPE: DNA
<213> ORGANISM: Rattus sp.

<400> SEQUENCE: 75

| | |
|---|---|
| tttttttttt tttttttttt tttttcgaaa aaaaaaaagg ggtaaaaaaa ggggttgaaa | 60 |
| cccaggggggg gggggccaaa accctccttt tttaataaac ctttaccgaa gaagggtcct | 120 |
| ccaaaggggg gggggggggg gggccccca cccgcccttt cagggttggg gggggggggg | 180 |
| aa | 182 |

<210> SEQ ID NO 76
<211> LENGTH: 293
<212> TYPE: DNA
<213> ORGANISM: Rattus sp.

<400> SEQUENCE: 76

| | |
|---|---|
| cgaatacaga ccgtgaaagc ggggcctcac gatccttctg accttttggg ttttaagcag | 60 |
| gaggtgtcag aaaagttacc acagggataa ctggcttgtg gcggccaagc gttcatagcg | 120 |
| acgtcgcttt ttgatccttc gatgtcggct cttcctatca ttgtgaagca gaattcacca | 180 |
| agcgttggat tgttcaccca ctaataggga acgtgagctg ggattagacc gtcgtgagac | 240 |
| aggttagttt taccctactg atgatgtgtt gttgccatgg taatcctagt cag | 293 |

<210> SEQ ID NO 77
<211> LENGTH: 295
<212> TYPE: DNA
<213> ORGANISM: Rattus sp.

<400> SEQUENCE: 77

| | |
|---|---|
| cgaatacaga ccgtgaaagc ggggcctcac gatccttctg accttttggg ttttaaggcc | 60 |
| aggaggtgtc agaaaagtta ccacagggat aactggcttg tggcggccaa gcgttcatag | 120 |
| cgacgtcgct ttttgatcct tcgatgtcgg ctcttcctat cattgtgaag cagaattcac | 180 |
| caagcgttgg attgttcacc cactaatagg gaacgtgagc tgggattaga ccgtcgtgag | 240 |
| acaggttagt tttaccctac tgatgatgtg ttgttgccat ggtaatcctg ctcag | 295 |

<210> SEQ ID NO 78
<211> LENGTH: 199
<212> TYPE: DNA
<213> ORGANISM: Rattus sp.

<400> SEQUENCE: 78

| | |
|---|---|
| ctgcagatat cgggactacc gggacccgcc gcattctttg gctccctatg gctacacact | 60 |
| gcagttctgg catgtcctcg cagctcggct ggctttcatc attgtgtttg agcacctcgt | 120 |
| gttttgtata aagcacctca tttcctatct gataccagac ctcccgaaag atctaaggga | 180 |
| ccggatgagg agagagaag | 199 |

<210> SEQ ID NO 79
<211> LENGTH: 404
<212> TYPE: DNA
<213> ORGANISM: Rattus sp.
<220> FEATURE:
<221> NAME/KEY: misc_feature
<222> LOCATION: (344)..(403)
<223> OTHER INFORMATION: n

<400> SEQUENCE: 79

```
ctttaatagc catggcctta tagacggtgg ccacgcggcc tgcacaggct gtgtgcatta      60
ggccctttag ccttgtttta cacttgcagc acctacttct gctggggttc aactcagtgc     120
acagcacttg cttagcctat gtgagaccct gcacttaatg cccagcacca cataaaagaa     180
acaaaatacc tctattttaa gatgatgctt aagaattatc ctattacaaa gcagcagcag     240
atataacttt acaattataa aagagctaaa ccagaaccca caatcagtgt ctaagtgcga     300
atctaataaa cactgcctct ctgcagctct taccagcttt ctgnngtggt acacacactc     360
acacacgcgc acacacacac acgcgctc cctcctactg tgng                       404

<210> SEQ ID NO 80
<211> LENGTH: 402
<212> TYPE: DNA
<213> ORGANISM: Rattus sp.

<400> SEQUENCE: 80
ctttaatagc catggcctta tagacggtgg ccacgcggcc tgcacaggct gtgtgcatta      60
ggccctttag ccttgtttta cacttgcagc acctacttct gctggggttc aactcagtgc     120
acagcacttg cttagcctat gtgagaccct gcacttaatg cccagcacca caaaaaagaa     180
acaaaatacc tctattttaa gatgatgctt aagaattatc ctattacaaa gcagcaaaaa     240
tataacttta caattataaa agagctaaac cagaacccac aatcagtgtc taagtgtgaa     300
tctaataaac actgcctctc tgcagctctt accagctttc tgggttggta cacacactca     360
cacacgcgca cacacacaca cacgcgctcc cttctactga gg                        402

<210> SEQ ID NO 81
<211> LENGTH: 403
<212> TYPE: DNA
<213> ORGANISM: Rattus sp.

<400> SEQUENCE: 81
ctttaatagc catggcctta tagacggtgg ccacgcggcc tgcacaggct gtgtgcatta      60
ggccctttag ccttgtttta cacttgcagc acctacttct gctggggttc aactcagtgc     120
acagcacttg cttagcctat gtgagaccct gcacttaatg cccagcacca caaaaaagaa     180
acaaaatacc tctattttaa gatgatgctt aagaattatc ctattacaaa gcagcaaaaa     240
taataacttt acaattataa aagagctaaa ccagaaccca caatcagtgt ctaagtgtga     300
atctaataaa cactgcctct ctgcagctct taccagcttt ctgggttggt acacacactc     360
acacacgcgc acacacacac acgcgctc cctcctactg agg                        403

<210> SEQ ID NO 82
<211> LENGTH: 349
<212> TYPE: DNA
<213> ORGANISM: Rattus sp.

<400> SEQUENCE: 82
atgcaggatc atgtgtgtgt acaacgaatg cctttcctt catgcagcac ttggacgggg      60
gtttggttgg cgttttgcat tatcacacaa ttggagctcc ttactgtgtg agccagcctt     120
ctcgacgccc ggtgattttt ttttaaaaga tgtcatgtct gactcaatac aataatgtca     180
tcttaaattt tggccccctta tttgaatact atagctacaa tcaaaataat ttgttaaatt     240
gcttatatta agagtaaaca tggatatgac attggttgtc cacctgcaaa ctttagaaca     300
atttactgta gcttgatgct tagccaattt taagtgagga attcaacat                349
```

<210> SEQ ID NO 83
<211> LENGTH: 118
<212> TYPE: DNA
<213> ORGANISM: Rattus sp.

<400> SEQUENCE: 83
ttcctcctcc tcactgctct ctgactcggc actgaggatg tcctcctcct cctcccggc       60 ttcactctcc tcctactctt cctcttcttc ctcctcctca ctgctgtgct gaccctcg       118

<210> SEQ ID NO 84
<211> LENGTH: 155
<212> TYPE: DNA
<213> ORGANISM: Rattus sp.

<400> SEQUENCE: 84
ttggagctaa ttgcgcgcgg ccgcggtacg acgaccctgg cacagagccc atggcgccag       60
gacagcaggc tagccttggg accttttttgt ggagtagttt gcagtgaggt aacggtgcaa       120
taaagtacag caagcgtgaa aaaaaaaaaa aaagg                                  155

<210> SEQ ID NO 85
<211> LENGTH: 533
<212> TYPE: DNA
<213> ORGANISM: Rattus sp.
<220> FEATURE:
<221> NAME/KEY: misc_feature
<222> LOCATION: (466)..(466)
<223> OTHER INFORMATION: n

<400> SEQUENCE: 85
gagctaattg cgcgcggccg cggtacgacg aacctgcagc tctgtcttct acattacatt       60
tatggctcct taaactgatt gcctaaccaa ccaagggcaa ttcccatcca tccatcacat       120
gggttgtggg aaggatgcag ccatggtgtg cagcttcctt catgaaggat tatctggcca       180
tggtacctga ctgcttcaca acttgctgtc actctgggtg agataatgtg tctttaaaaa       240
cagtccctgt ggcaggtcac tgggatataa tgtacaacat tcttagccat catttctttt       300
cttttttttt cttttttttg gtttgccctg agagactccc agtggtttct actgagggct       360
aaagggacga gctgttccct cattgagcaa gaccgttcgc tgttcatgat gtgttttatg       420
atggcttctt tgggagttgc ttcttcaaca gtctcaactg tgctgnggga tctcctgatg       480 ctgactttttg accttcgttt tattaaaact aattagtgaa aaaaaaaaaa aaa              533

<210> SEQ ID NO 86
<211> LENGTH: 123
<212> TYPE: DNA
<213> ORGANISM: Rattus sp.

<400> SEQUENCE: 86
ggtacgacga ccctgcgatc tgagacccac tttgcagaca tgtgcacaga tgtgttccat       60 ttccctatttt ctgctgtaga gaaacaagta aattttctta gagaatgaaa aaaaaaaaa       120 aaa                                                                    123

<210> SEQ ID NO 87
<211> LENGTH: 347
<212> TYPE: DNA
<213> ORGANISM: Rattus sp.

<400> SEQUENCE: 87
aatctttgga cgagagcgtg ccatcatgct gttggaaggc cagaaagtgg tcccccggag       60

| | |
|---|---|
| gacactggcc acgggctacc agtattcctt cccagagtta ggagctgcct taaaggatgt | 120 |
| tgtaacctaa gtagagaagg gagccccaag gcaggaggtg gggcctgttc ctgcattctg | 180 |
| agaagtgagt caggtgattg ctgtgcttga ctgagatcag aagccatctg gctcttagac | 240 |
| tctctctctc tccctttct tcccatgttc tgttgatcca cctctctcca agaaactcca | 300 |
| gtctcaagga tctaatctca ttctaacctt aacctcctca acttctt | 347 |

<210> SEQ ID NO 88
<211> LENGTH: 438
<212> TYPE: DNA
<213> ORGANISM: Rattus sp.

<400> SEQUENCE: 88

| | |
|---|---|
| aatctttgga cgagagcgtg ccatcatgct gttggaaggc cagaaagtgg tcccccggag | 60 |
| gacactggcc acgggctacc agtattcctt cccagagtta ggagctgcct taaaggatgt | 120 |
| tgtaacctaa gtagagaagg gagccccaag gcaggaggtg gggcctgttc ctgcattctg | 180 |
| agaagtgagt caggtgattg ctgtgcttga ctgagatcag aagccatctg gctcttagac | 240 |
| tctctctctc tccctttct tcccatgttc tgttgatcca cctctctcca agaaactcca | 300 |
| gtctcaagga tctaatctca ttctaacctt aacctcctca acttcttgtg gcttctgtgt | 360 |
| cacattgttg ccctggttct cctacatgct atgtagacaa agttctacag ttgtggcaat | 420 |
| aaaggtagac tgtgtctg | 438 |

<210> SEQ ID NO 89
<211> LENGTH: 90
<212> TYPE: DNA
<213> ORGANISM: Rattus sp.

<400> SEQUENCE: 89

| | |
|---|---|
| tggagctaat tgcgcgcggc cgcggtacga cgaacctgcg acgtgagacc gttttaataa | 60 |
| aagtgccacc ttacaaaaaa aaaaaaaaaa | 90 |

<210> SEQ ID NO 90
<211> LENGTH: 121
<212> TYPE: DNA
<213> ORGANISM: Rattus sp.

<400> SEQUENCE: 90

| | |
|---|---|
| ctcgtagagg cacagcgaat atgcgaaatt gcactctcgc aaacaagact ccgtcaacat | 60 |
| acctaagaca tagagacgcc cggggagct aggtcaaaag gcatggaacc agcggtcgcc | 120 |
| g | 121 |

<210> SEQ ID NO 91
<211> LENGTH: 469
<212> TYPE: DNA
<213> ORGANISM: Rattus sp.
<220> FEATURE:
<221> NAME/KEY: misc_feature
<222> LOCATION: (459)..(460)
<223> OTHER INFORMATION: n

<400> SEQUENCE: 91

| | |
|---|---|
| ggtcgacggt agccgcggca gccgaacacg cacagagctg cgctttcccc aaagcgaagg | 60 |
| gtaggaaatg gaaagggcct tgcggccggg aatggctgag ctaggctcct gcagctacca | 120 |
| actccaggca gtttaaagca cctttcttgc acgccccgac ctcgtgagtg gagtctagct | 180 |
| ggagaaacaa aggctcttct ttgtagaaag aactctccca caaagagaga aaaattctct | 240 |

```
caagagaagc tgtgacttgc ccttgggtca cacgtggcaa actctcccgt gaacccgaga      300
cccagagcca aggcctttat ctccgtaaca gttatccctg taaagaattc tcttgtgagt      360
cctttacagt tactctggca tctcatatgt atgcgtatat gcatcagatg aactggtttc      420 catcccttg atgttctata aatagactct atcacggann aaaaaaaaa                   469

<210> SEQ ID NO 92
<211> LENGTH: 415
<212> TYPE: DNA
<213> ORGANISM: Rattus sp.

<400> SEQUENCE: 92
agggtaggaa atggaaaggg ccttgcggcc gggaatggct gagctaggct cctgcagctc       60
ccaactccag gcagtttaaa gcacctttct tgcacgcccc gacctcgtga gtggagtcta      120
gctgaagaaa caaggctct tctttgtaga aagaactctc ccacaaagag agaaaaattc      180
tctcaagaga agctgtgact tgcccttggg tcacacgtgg caaactctcc cgtgaacccg      240
agacccagag ccaaggcctt tattcccgga taacagttat ccctgtaaag aattctcttg      300
tgagtccttt acagttactc tggcatctca tatgtatgcg tatatgcatc agatgaactg      360
ttttccatcc ctttgatgtt ctataaatag actctatcac ggaaaaaaaa aaaaa          415

<210> SEQ ID NO 93
<211> LENGTH: 347
<212> TYPE: DNA
<213> ORGANISM: Rattus sp.

<400> SEQUENCE: 93
ggagctaatt gcgcgcggcc gcggtacgac gaacctgcgc atggatacga agtggggtgg       60
gagaagctca cccactgtga cttttaagaa ctcctgtgtg atgggaggaa ggtacaggtt      120
cctcaccatc cccagccctt cctctggatg aggatgtgaa ggacagaggc atctccaaaa      180
tgggctactt ttggtataga ccttaggagt gtggggctgg tgtaagctct tggttccttt      240
aaaaggagaa ttttattttg ttttgttcag tttagacatt cctggatgca gtttgattgg      300
ttaaattaaa agttgatttt tttttccagt aaaaaaaaaa aaaaaaa                    347

<210> SEQ ID NO 94
<211> LENGTH: 253
<212> TYPE: DNA
<213> ORGANISM: Homo sapiens
<220> FEATURE:
<221> NAME/KEY: misc_feature
<222> LOCATION: (156)..(238)
<223> OTHER INFORMATION: n

<400> SEQUENCE: 94
ttaaaactgc ttaccagtgg ctgtctgcgc tgcggaaggt gagcatcaac aacacgggac       60
tgttgggctc ctaccaccct ggcgtcttcc gtggggacaa gtggagctgc tgccaccaaa      120
aagagaagac aggtcagggc tgcgataaga cccggncacg ggtgaccctg caggagtgga      180
atgaccctnt tgaccgtgac cttgaggccc anctcatcta ccggcacctg ctgggcgngg      240
aggccatgct gtg                                                         253

<210> SEQ ID NO 95
<211> LENGTH: 159
<212> TYPE: DNA
<213> ORGANISM: Homo sapiens
<220> FEATURE:
<221> NAME/KEY: misc_feature
```

<222> LOCATION: (2)..(2)
<223> OTHER INFORMATION: n

<400> SEQUENCE: 95

```
cnccccaggc taaagagcag gtgggtgggc ttggactggg cgtgctccat ggcagagatc      60
ctgcggtcac tcaacagtgc cccactgtgg cgtgatgtca ttgccacctt cacagaccac     120
tgcatcaagc agctgccatt cccttatcgt cgtcgtcct                            159
```

<210> SEQ ID NO 96
<211> LENGTH: 220
<212> TYPE: DNA
<213> ORGANISM: Homo sapiens

<400> SEQUENCE: 96

```
gataagagaa tccttcatct ttgacctggc ttttttttcgc cctttgggag ataaaggtcc     60
ctctccaccc tctactaaca ctctgcaccc aaggccttat cctttggggt caccagctcc    120
ttggccattt ctatgtgatt tcccccaccc atctgagttc cagtttcctc tgggctccaa    180
tctccagtcc ctggcggatc tggtcagtcc caccctagg                           220
```

<210> SEQ ID NO 97
<211> LENGTH: 212
<212> TYPE: DNA
<213> ORGANISM: Homo sapiens

<400> SEQUENCE: 97

```
gataagcaca cggaccttga gctgctccac gtgccccagc acctgagccc gctcttcttc     60
cagggctagc acctctccct ggagcttggt gctaggtgca tcttcgtgct cctgctgggt    120
gctctcagtg ccgctgcact cctccttgag attttcctca tctgagcgct ccatactctc    180
ccataggcgt tgggtggcaa ctagttagtt ag                                   212
```

<210> SEQ ID NO 98
<211> LENGTH: 100
<212> TYPE: DNA
<213> ORGANISM: Homo sapiens

<400> SEQUENCE: 98

```
cattgtccct gtaatcgatg gacgaatagc ggaaagtcgt gcacgaacac caagtgtctc     60
atagttgggc ttatcgtcgt cgtccttgta atccatggtg                          100
```

<210> SEQ ID NO 99
<211> LENGTH: 239
<212> TYPE: DNA
<213> ORGANISM: Homo sapiens

<400> SEQUENCE: 99

```
gataagtgag tgaccagttg tgtggcattt ctgcctgcca gacggatgac atatacaacc     60
gaaactgcct tattgaattg gtcaactgtc agatggttct tcgtggagca gagacagaag    120
gctgtgtcat tgtgtcagct gccaaagccc aactgctgca gtgccagcac catccagcct    180
ggtatggtga tacattgaag caaaagacat cctggacttg cctcttggta gttagttag    239
```

<210> SEQ ID NO 100
<211> LENGTH: 45
<212> TYPE: DNA
<213> ORGANISM: Homo sapiens

<400> SEQUENCE: 100

```
ctgcctgcat cctggcccca ggtcttcttg ggggctttgt ctgga            45
```

<210> SEQ ID NO 101
<211> LENGTH: 172
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n

<400> SEQUENCE: 101

```
cnaaacacaa acaaatgaag tgacttggga gttaccccaa tatcttgcca cacaggtaca    60
gggattacag cattaccaac ccagttctgt gccaggtgct gaaactagtt ttgtggtaaa   120
tacagacata tattctaagg agaaaacgat ttctgcttat cgtcgtcgtc ct           172
```

<210> SEQ ID NO 102
<211> LENGTH: 156
<212> TYPE: DNA
<213> ORGANISM: Homo sapiens

<400> SEQUENCE: 102

```
cccggtggcc agggaacccca cttccaagcg cagggacgcc ggcctccagc tggtttgtgc    60
taaggctccg tcctgactgc cctgtgccct ggaaaagcag caatagcatc cgccccttag   120
agccctctta tcgtcgtcgt ccttgtaatc catggt                              156
```

<210> SEQ ID NO 103
<211> LENGTH: 118
<212> TYPE: DNA
<213> ORGANISM: Homo sapiens

<400> SEQUENCE: 103

```
aagcttggag agatgcgcct gaaggaggcg ggcacggtgg ggagaggagg tgggcaggag    60
gaacggccct ttgtggcccg gtttggattt gacgtggtga cgtgctgtgg atacctcc     118
```

<210> SEQ ID NO 104
<211> LENGTH: 174
<212> TYPE: DNA
<213> ORGANISM: Homo sapiens
<220> FEATURE:
<221> NAME/KEY: misc_feature
<222> LOCATION: (42)..(42)
<223> OTHER INFORMATION: n

<400> SEQUENCE: 104

```
ttccttagca gctaagcatt tgaatcagac ttctcatagc antgttatgg gctgtctgat    60
atattcagga tttgttgagc agataagctg tgtgtgatct tactcattct cagccatgcc   120
gcagacatac ccatttccct ttagtaattt tttaatacag agaatgctat taac          174
```

<210> SEQ ID NO 105
<211> LENGTH: 139
<212> TYPE: DNA
<213> ORGANISM: Homo sapiens
<220> FEATURE:
<221> NAME/KEY: misc_feature
<222> LOCATION: (120)..(120)
<223> OTHER INFORMATION: n

<400> SEQUENCE: 105

```
aagcacaagc gtggtagtag atcaggtact gtatcaaaga ggcagagggc tgtaagtatg    60
agtgggctgg gctgcaagac ttctatacca tcctagatca ctagaccgca cccagcatan   120
```

<210> SEQ ID NO 106
<211> LENGTH: 149
<212> TYPE: DNA
<213> ORGANISM: Homo sapiens

<400> SEQUENCE: 106

```
cccttagacc ttccctcaac agaggacact gagcccaacg gagttctggg atgggagggg      60
tgggagcatg ggaagggagg catcccaccc ccaagaagaa ctgaataaag attgctgagc     120
ttatcgtcgt cgtccttgta atccatggt                                       149
```

<210> SEQ ID NO 107
<211> LENGTH: 159
<212> TYPE: DNA
<213> ORGANISM: Homo sapiens
<220> FEATURE:
<221> NAME/KEY: misc_feature
<222> LOCATION: (120)..(149)
<223> OTHER INFORMATION: n

<400> SEQUENCE: 107

```
cctgtggatt tgacctcaga gataagtggg acagagcttg gtagaagcac cagtgtgggc      60
aaaggtcctg agtctgaaca gaacatggca tgtgaggaat gaagcagcct ggccctaggn     120
gaagctgana aaaccctgca ggtccttgna atccatggt                             159
```

<210> SEQ ID NO 108
<211> LENGTH: 128
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n

<400> SEQUENCE: 108

```
tccccacggg gtcccgcang gtaccacccc actccgctcc tcaaacgggg ccgacataat      60
ccagtccctc ccggccgcgg ccgcaccacc ccactccgct tatcgtcgtc gtccttgtaa     120
tccatggt                                                              128
```

<210> SEQ ID NO 109
<211> LENGTH: 234
<212> TYPE: DNA
<213> ORGANISM: Homo sapiens
<220> FEATURE:
<221> NAME/KEY: misc_feature
<222> LOCATION: (20)..(221)
<223> OTHER INFORMATION: n

<400> SEQUENCE: 109

```
tccctctttc agaaccctgn cagacaccac ctcctttgta accttaaagc aggttcacag      60
actatctcct ggttcttagg gatttcttct gtcgaaaaga gttctnaaaa ataacagnaa     120
cctgagatac catctgttaa atncttaagc aatttcgcat gccttatgag accntgctga     180
ttaaaaacat ctagtcttgt tttcttttt ttgagacgaa ntctcgctct gtca            234
```

<210> SEQ ID NO 110
<211> LENGTH: 114
<212> TYPE: DNA
<213> ORGANISM: Homo sapiens

```
<400> SEQUENCE: 110
ttcctgagga gcgacatgtg gttgaacgcc tggacgggac acaagcggac caaggaaaga      60
gtggcatggt ccaccctctc aagggcctag ctatcatgat acgaggcgaa tggg           114

<210> SEQ ID NO 111
<211> LENGTH: 227
<212> TYPE: DNA
<213> ORGANISM: Homo sapiens
<220> FEATURE:
<221> NAME/KEY: misc_feature
<222> LOCATION: (30)..(175)
<223> OTHER INFORMATION: n

<400> SEQUENCE: 111
ttaatccgtt tgaaactcat caggatttgn caggggagtc ggatgagctt ggcatttccc      60
aggatgagca gctatccaag tttagtttaa gggaaaccac aggctccgag agtgatgggg     120
gtgactcaag cagcaccaag tctgaaggtg ccaacgggac agtggcaact gcagnaatcc     180
agcccaagaa agttaagctt atcgtcgtcg tccttgtaat ccatggt                   227

<210> SEQ ID NO 112
<211> LENGTH: 199
<212> TYPE: DNA
<213> ORGANISM: Homo sapiens
<220> FEATURE:
<221> NAME/KEY: misc_feature
<222> LOCATION: (34)..(34)
<223> OTHER INFORMATION: n

<400> SEQUENCE: 112
tgtaataccg ttggttacag gacacgcggg gcangggagc gtgaggctta ggagcaatta      60
ggagacaaag gttctgcttt ccaccaaacc ttcttcggtc tgggccctcc cttagcaacc     120
ctggggcttt agactctctc tccaccaatc cctgatgacc ccggtggtgc ctcacaatgg     180
gcattccaag tagcgcccg                                                   199

<210> SEQ ID NO 113
<211> LENGTH: 252
<212> TYPE: DNA
<213> ORGANISM: Homo sapiens

<400> SEQUENCE: 113
gataagtttc attttggaa gggctgcatt aacaaatatt tgatttctta gttcacagtc       60
aaggacctgt tgagaaatct gagctcgact tgtaggctta attagttagt taggatccta     120
actaactagg gacctggaca gcatcttccg ccgtatcagg acgctgaaag ggaaactggc     180
caggcagcac ccagaggcct tcagccatat cccagaggca tccttcctgg aggaagagga     240
tgcttatcgt cc                                                          252

<210> SEQ ID NO 114
<211> LENGTH: 161
<212> TYPE: DNA
<213> ORGANISM: Homo sapiens

<400> SEQUENCE: 114
gataagccag ggggcagaag gtagagccca tggggctgct ctggctgtag gtttaggccc      60
agcacccctc ccgaggcagc ataagcagga gagaagaagg ctagtccttg gcaccacaag     120
gccccgaggg cagccacagc ctcggcctgg tagttagtta g                         161
```

```
<210> SEQ ID NO 115
<211> LENGTH: 161
<212> TYPE: DNA
<213> ORGANISM: Homo sapiens
<220> FEATURE:
<221> NAME/KEY: misc_feature
<222> LOCATION: (18)..(151)
<223> OTHER INFORMATION: n

<400> SEQUENCE: 115 cttttttcc  ttaacacncc  ggccgnggct  gtggctgccc  tcggggcctt  gtggtgccaa      60
ggactagcct  tcttctctcc  tgcttatgct  gcctcgggag  gggtgctggg  cctaaaccta     120
cagccagagc  agccccatgg  gctctacctt  ntgccccctg  g                         161

<210> SEQ ID NO 116
<211> LENGTH: 184
<212> TYPE: DNA
<213> ORGANISM: Homo sapiens
<220> FEATURE:
<221> NAME/KEY: misc_feature
<222> LOCATION: (14)..(14)
<223> OTHER INFORMATION: n

<400> SEQUENCE: 116
tttatacctt  aagncttccc  tgtccctct  acccagatca  tttgggaaat  ataaatgtgc      60
agtcctaagc  gctgcccgca  gggtcgcgat  gtctgccagg  tactgctggc  tggctctaga    120
caccagcagc  agtgataaga  aacaaagcag  aggagacgtt  gaggcagcag  agacagcaga    180
tccg                                                                     184

<210> SEQ ID NO 117
<211> LENGTH: 261
<212> TYPE: DNA
<213> ORGANISM: Homo sapiens
<220> FEATURE:
<221> NAME/KEY: misc_feature
<222> LOCATION: (207)..(207)
<223> OTHER INFORMATION: n

<400> SEQUENCE: 117
gataagcttt  tcagtaacat  tttatacatc  tacttgtcaa  tgtatttgag  acattcacag     60
ccaaaagcct  gggactcttt  gtgaaggtcc  tcctcacctc  tatctttctt  tctctctctc    120
tcaaactttc  cttaaagttc  tcattgcctt  tgcactgctt  ctgtgaacag  tctttgtctc    180
ctccccacct  ttggtgggaa  gtgcggngca  gtcctggtca  agacactcat  gccctggcaa    240
tgtggctgcc  tagttagtta  g                                                261

<210> SEQ ID NO 118
<211> LENGTH: 124
<212> TYPE: DNA
<213> ORGANISM: Homo sapiens

<400> SEQUENCE: 118
tgagatgcac  acaaaggaaa  ggtgtgagag  tgcttggaag  catccagctg  agcccactgg     60
atgaaaatca  gacgataggg  cctcctgttg  taatcttatc  gtcgtcgtcc  ttgtaatcca    120
tggt                                                                     124

<210> SEQ ID NO 119
<211> LENGTH: 238
<212> TYPE: DNA
<213> ORGANISM: Homo sapiens
```

```
<400> SEQUENCE: 119
cctttggaca gaacgactcg atgctatggg gcgccgcggc ccagctgact cggatcttct      60
cgtcccggtc ggcagtgagg atgaagcggt catcaggact cacagccaca tctaacagca    120
tagacaggtg ccccagctct agacggccac acccgtgtgg ctccagcacc gaaaaggagt    180
agacgtctcc agacttgtcg gccaccaaga ccttctcctc cgaggctatg aaagtcag     238

<210> SEQ ID NO 120
<211> LENGTH: 137
<212> TYPE: DNA
<213> ORGANISM: Homo sapiens
<220> FEATURE:
<221> NAME/KEY: misc_feature
<222> LOCATION: (2)..(67)
<223> OTHER INFORMATION: n

<400> SEQUENCE: 120
cnagatacac agatagganc acatgtncct ggnccgttac acaacaccaa atctggcttc      60
accctgngaa ttaggggaaa ggagagccac atggagtgca aggtggtgaa aacggtggag    120
ggccaggact gctgaac                                                   137

<210> SEQ ID NO 121
<211> LENGTH: 91
<212> TYPE: DNA
<213> ORGANISM: Homo sapiens

<400> SEQUENCE: 121
ataagcgtgg gttcatacat gcattgggtg ctaggcccca gcctgccggg tggcaccctt      60
tacagttcct ttgaacaggg tagttagtta g                                    91

<210> SEQ ID NO 122
<211> LENGTH: 171
<212> TYPE: DNA
<213> ORGANISM: Homo sapiens
<220> FEATURE:
<221> NAME/KEY: misc_feature
<222> LOCATION: (11)..(140)
<223> OTHER INFORMATION: n

<400> SEQUENCE: 122
cccgaaagcg ngtaaggcct ccagaccacc aacactcagc tcaagtcaaa cgtccctctg      60
tgtccaaaga ggggaggaaa acatccatca aatctcatnn gtctgggtct ccaggccctg    120
gtggnagcaa cacattttn atccacacca gtcattgggg gcagtgataa g              171

<210> SEQ ID NO 123
<211> LENGTH: 165
<212> TYPE: DNA
<213> ORGANISM: Homo sapiens

<400> SEQUENCE: 123
gccgatgcaa caaccacatt gactccaagg acaatctaaa attgaactca aggcagcacc      60
taacaagtct ctcgtgcttg caccctcctt ctaggcccat ctaaaagcct ctctgcctca    120
ggcgttctcc cagaagatct gcccactctc ttccccacac cagcc                    165

<210> SEQ ID NO 124
<211> LENGTH: 174
<212> TYPE: DNA
<213> ORGANISM: Homo sapiens

<400> SEQUENCE: 124
```

-continued

```
ctctacattg tggccctcaa taatagaata aatttgtgaa aaagctgcat gttttaattt       60
aggaaatgag tagaagttca caagcaaccc agaataggtg ccagcagttt gctccagtgg      120
gccacaccac agcagcagct caggctctgc agaatcactg tgtccagtgc ttcc           174
```

<210> SEQ ID NO 125
<211> LENGTH: 158
<212> TYPE: DNA
<213> ORGANISM: Homo sapiens

<400> SEQUENCE: 125

```
acctgcttct gaagctccaa cctcctccct caccatattg tagccatagt agcctttctc       60
atccaaatta tgccaacttt ctatctcctc atgagatatt tgcacctgcc gttcccagta      120
acctcagggc tcagtgcatg agttgaagct gcctttct                              158
```

<210> SEQ ID NO 126
<211> LENGTH: 124
<212> TYPE: DNA
<213> ORGANISM: Homo sapiens
<220> FEATURE:
<221> NAME/KEY: misc_feature
<222> LOCATION: (80)..(80)
<223> OTHER INFORMATION: n

<400> SEQUENCE: 126

```
ccatctaagg gcccgtcaca gctttgtctg ttgccccaga atttcgacgc cttggtttgg       60
ctgctaaact tatggagttn ctagaggaga tttcagaaag aaagggtgga tttttttgtgg    120 atct                                                                  124
```

<210> SEQ ID NO 127
<211> LENGTH: 180
<212> TYPE: DNA
<213> ORGANISM: Homo sapiens

<400> SEQUENCE: 127

```
gataagagtt gcagtcaggc ttcatacgct attgtcctgc ccgtaagttc ccgttttgtg       60
tgtggttaga gcagccagcg ggtacagaat ggattttgga agagggagtc accactggac      120
ctccaaggaa gccacgtgca gacatctaca caggatgaat gcgggtgttg gtagttagtt     180
```

<210> SEQ ID NO 128
<211> LENGTH: 209
<212> TYPE: DNA
<213> ORGANISM: Homo sapiens
<220> FEATURE:
<221> NAME/KEY: misc_feature
<222> LOCATION: (19)..(202)
<223> OTHER INFORMATION: n

<400> SEQUENCE: 128

```
tgtgaagaac ctgtatccnc ttagaaagtg tcttttgtcc tggggtgaga gggtgactgc       60
atgtgccctc tngcagtctg ctgctgtgtc cagagtccga ctccagctgg ctgtaactg       120 ggcttggccc ccgccttagg ccccgccagc aggcgaagca gggagatgtc agactgctac     180
acggagctgg agaaggcagt cnttgtcct                                       209
```

<210> SEQ ID NO 129
<211> LENGTH: 137
<212> TYPE: DNA
<213> ORGANISM: Homo sapiens
<220> FEATURE:

```
<221> NAME/KEY: misc_feature
<222> LOCATION: (13)..(45)
<223> OTHER INFORMATION: n

<400> SEQUENCE: 129
tttataccat ttnccccctng gtgaacagtc ctacaagcag cctgnagatt cttctcccta      60
catctcctgt aaggacgaag gagtggtgta acctgagctc cggccctgtg gagaccctca     120
tgaggcctga ggctaag                                                    137

<210> SEQ ID NO 130
<211> LENGTH: 84
<212> TYPE: DNA
<213> ORGANISM: Homo sapiens
<220> FEATURE:
<221> NAME/KEY: misc_feature
<222> LOCATION: (46)..(47)
<223> OTHER INFORMATION: n

<400> SEQUENCE: 130
cccctcttcc tcaacggcaa caaaaactcc ccaagtcagc actctnntta ttttatacgc      60
cacaaccctc ttgtaatcca tggt                                             84

<210> SEQ ID NO 131
<211> LENGTH: 120
<212> TYPE: DNA
<213> ORGANISM: Homo sapiens

<400> SEQUENCE: 131
agttgaatat ttatccaact cagaagaccc taaaaaagca cttgttcgat tctttgaggc      60
tgttggtgta acttacggga acgtccagac actttctgat aaatctgcca tggtcacaaa    120
```

GENES INVOLVED IN STROKE RESPONSE AND/OR REGULATED BY FK506, PROTEINS ENCODED THEREBY, AND METHODS OF USE

This application claims the benefit of Provisional application Ser. No. 60/254,542 filed Dec. 12, 2000.

FIELD OF THE INVENTION

The present invention relates to genes and the proteins encoded thereby which are involved in neurotoxicity and/or are regulated by FK506. Polynucleotides were discovered using in vivo or in vitro models by determining which genes were differentially upregulated or downregulated when subjected to various stresses, such as hypoxia, and/or upon treatment of the model with FK506. Polynucleotides were also found by a functional selection (assay) of cDNA fragments specifically selected for their ability to confer cell resistance to various stresses which can result in neurotoxicity, such as hypoxia, glutamate or dopamine treatment. The invention includes such polynucleotides, corresponding genes, and proteins encoded thereby, as well as naturally-occurring variants of such polynucleotides, analogs, salts and functional derivatives of such proteins, DNA encoding such analogs, antibodies, antisense molecules and methods of use. Such methods of use include methods for protecting cells from neurotoxicity and ameliorating the effects of stroke, hypoxia and/or ischemia by regulating such genes or proteins.

BACKGROUND OF THE INVENTION

Brain injury such as trauma and stroke are among the leading causes of mortality and disability in the modern world.

Traumatic brain injury (TBI) is one of the most serious reasons for hospital admission and disability in modern society. Clinical experience suggests that TBI may be classified into primary damage occurring immediately after injury, and secondary damage, which occurs during several days post injury. Current therapy of TBI is either surgical or else mainly symptomatic. Stroke is the third leading cause of death and disability in developed countries, affecting more than half a million Americans each year. Stroke is an acute neurologic injury occurring as a result of an insult to the brain, thus interrupting its blood supply. Stroke induces neuronal cell death, which leads to the clinical outcomes of patients' death or disability ranging from total paralysis to milder dysfunction. Cerebral ischemia is the most common type of stroke, which may lead to irreversible neuronal damage at the core of the ischemic focus, whereas neuronal dysfunction in the penumbra may be reversible. Cells in the penumbra have an estimated time window for survival of up to 6 hours. The ability to intervene as soon as the patient is identified is essential for recovery. It is well established that ischemic tissue damage is multifactorial and involves at least excitotoxicity, reactive oxygen species, and inflammation—all leading to neuronal cell death.

Treatment strategies for stroke are aimed to induce rapid reperfusion and rescue of neurons in the penumbral area. Neuroprotective drugs are constantly being developed in an effort to rescue neurons in the penumbra from dying. However, potential cerebroprotective agents need to counteract all the above-mentioned destructive mechanisms. Therefore, current therapy in stroke focuses primarily on prevention, minimizing subsequent worsening of the infarction, and decreasing edema.

FK506 (tacrolimus) is a known immunosuppressive agent produced by *Streptomyces tsukubaesis*, a species discovered by the Fujisawa Pharmaceuticals' scientists in a soil sample from Tsukuba, Japan. See Kino et al, 1987, and U.S. Pat. No. 5,338,684. FK506 possesses neuroprotective activity by delaying or preventing hypoxia-induced death of neuronal cells. In addition, it can cause regrowth of damaged nerve cells. The specific molecular mechanism underlying the neuroprotective activity of FK506 is largely unknown although there are indications for suppression of activities of calcineurin and nitric oxide synthase as well as prevention of stroke induced generation of ceramide and Fas signaling. An additional model has been proposed involving steroid receptor complexes in context of FK506 neurotrophic actions. As a first step to novel drug discovery, these mechanisms should be delineated and key genes involved in these processes should be identified.

SUMMARY OF THE INVENTION

The polynucleotides of the present invention have been discovered by merging two technologies:

(1) microarray-based differential gene expression, evaluated in both in viva and in vitro models, and (2) direct functional selection of genes with pro- or anti-apoptotic activities, performed in cell systems subjected to neurotoxic stress, such as hypoxia, glutamate or dopamine.

Differential profiling of gene expression was performed both in an in vivo model of permanent ischemia in rats either treated or untreated with FK506, performed by electrocoagulation of middle cerebral artery (MCA), and in an in vitro model of primary rat cerebellar neuron cultures exposed to hypoxia, with or without FK506 treatment. Polynucleotides were identified which were either upregulated or downregulated by either ischemia/hypoxia or the FK506 treatment or influenced by the combination of both treatments. Two proprietary cDNA microarrays, the "Apoptosis" and "Stroke" chips, were used in this study.

In addition, a direct functional selection of genes exhibiting pro-or anti-apoptotic activities induced by hypoxia, glutamate or dopamine was done on BE2C, an established human neuroblastoma cell line, upon introduction of expression cDNA library cloned into retroviral vector.

Accordingly, the present invention is directed to either novel polynucleotides whose expression (or function) in cells, in particular neural cells is modulated when cells are subjected to neurotoxic stress or whose activity is important for transduction of neurotoxic signals.

A total of 131 fragments, SEQ ID Nos: 1–131, were characterized as polynucleotides located in genes whose expression in neural cells is modulated when cells are subjected to neurotoxic stress or whose activity is important for neurotoxic signal transduction. Of these, 14 fragments which are incorporated in cDNA clones (all being KIAA clones) have been identified in our selection procedures as particularly preferred. This includes all of the polynucleotides of SEQ ID NOs:49, 50, 51, 65, 67, 85, 87 and 94–100, as well as the naturally-occurring full-length RNAs and corresponding full-length cDNAs and genes and natural antisense polynucleotides which include any one of these sequences, and corresponding polypeptides and proteins encoded by them.

Currently most preferred according to the present invention are the polynucleotides identified as SEQ ID NO: 94, which is a fragment of KIAA 0538 and SEQ ID NO: 65 which is a fragment of KIAA 0284. The former of these has been further identified as encoding a Ca2+-dependent Ras-GTPase Activator Protein. Elevated expression of Ras-GAP results in increased Ras inactivation and may contribute to cell death, in particular neuronal cell death.

The invention is further directed to naturally-occurring polynucleotides having at least 70% identity with any of the polynucleotides which include any one of SEQ ID Nos: 1–131, preferably SEQ ID Nos: 49, 50, 51, 65, 67, 85, 87 and 94–100, or which are capable of hybridizing under moderately stringent conditions to any of such polynucleotides, and whose expression or activity in naturally-occurring neural cells is modulated when the cells are subjected to neurotoxic stress.

The present invention is also directed to the polynucleotide comprising the sequence of any one of SEQ ID Nos: 1–48, 52–64, 66, 68–84, 86, 88–93, 101–131, which are novel polynucleotides and genes. The expression or activity of these polynucleotides in naturally-occurring neural cells is modulated when the cells are subjected to neurotoxic stress.

The present invention is also directed to fragments having at least 20 nucleotides of any of the polynucleotides of the present invention and to polynucleotide sequences complementary to any of such polynucleotides or fragment and to polypeptides encoded by any of the polynucleotides of the present invention.

In a more preferred embodiment, the isolated polynucleotide is a strand of a full-length cDNA.

According to one currently more preferred embodiment, the invention particularly encompasses methods for screening drugs which upregulate or downregulate a gene which is transcribed to an RNA containing a sequence of any of SEQ ID Nos: 1–131, preferably SEQ ID NOs: 49, 50, 51, 65, 67, 85, 87 and 94–100.

According to another more preferred embodiment, the present invention provides methods for screening a compound which induces or inhibits apoptosis after exposure of neural cells or other cells such as glia, lymphocytes, macrophages to a neurotoxic insult.

According to yet another more preferred embodiment, the present invention provides methods of screening for a compound capable of exerting a neuroprotective effect that ameliorates or diminishes the damage induced by a neurotoxic insult.

The present invention is further directed to isolated proteins or polypeptides encoded by any such full-length cDNA, as well as variants which have an amino acid sequence having at least 70% identity to such an isolated protein and retain the biological activity thereof, or biologically active fragments of such protein or variant, as well as to salts or functional derivatives of any such protein, variant or biologically active fragment. The expression or activity of these polypeptides in naturally-occurring neural cells is modulated when the cells are subjected to neurotoxic stress. The present invention is preferably directed to the polypeptides encoded by polynucleotides comprising the sequence of any one of SEQ ID Nos: 1–48, 52–64, 66, 68–84, 86, 88–93, 101–131.

The present invention is also directed to antibodies specific to any of the proteins, variants or fragments of the present invention and to any molecule comprising the antigen-binding portion of any such antibody, in particular to the antibodies. The present invention is particularly directed to antibodies specific to the polypeptides encoded by polynucleotides comprising the sequence of any one of SEQ ID Nos: 1–48, 52–64, 66, 68–84, 86, 88–93, 101–131, which are novel polypeptides. The present invention is also directed to a molecule which comprises the antigen-binding portion of an antibody specific for a protein, variant or fragment.

The present invention also comprehends antisense DNA/RNA of a length sufficient to prevent transcription and/or translation of any gene identified in accordance with the present invention, preferably comprising a sequence which is complementary to a portion of a gene of which a sequence of SEQ ID NO:94 is a part or complementary to a portion of a gene of the KIAA0538 gene family. The present invention also comprehends ribozymes which specifically bind and cleave mRNA sequences identified in accordance with the present invention.

The present invention further comprehends methods of treating the effects of stroke, hypoxia and/or ischemia, and neurotoxicity as well as for diagnosing cells which have been subjected to hypoxia and/or ischemia, using the polynucleotides, polypeptides/proteins, antibodies, or ribozymes of the present invention.

The present invention further comprehends methods of treating the effects of neurotoxicity, stroke, hypoxia, or ischemia, comprising regulating in the cells to be treated the level of expression of any of the polynucleotides of the present invention, preferably polynucleotides comprising SEQ ID Nos: 49, 50, 51, 65, 67, 85, 87, 94–100, most preferably polynucleotides comprising SEQ ID No: 94 (corresponding to KIAA0538).

The present invention further comprehends methods of treating the effects of neurotoxicity, stroke, hypoxia, or ischemia, comprising bringing into the vicinity of the cells to be treated any of the polypeptides of the invention, preferably a polypeptide encoded by a cDNA comprising a polynucleotide having a sequence SEQ ID NO:65 (corresponding to KIAA0284), a variant which has an amino acid sequence having at least 70% identity to said polypeptide and retains the biological activity thereof, or a fragment of said polypeptide or variant which retains the biological activity thereof, or a functional derivative or salt of said protein, variant or fragment.

The present invention further comprehends methods of treating the effects of neurotoxicity, stroke, hypoxia, and/or ischemia, comprising bringing into the vicinity of the cells to be treated an agent for inhibiting the polypeptide a protein encoded by a cDNA selected from SEQ ID No:94 or KIAA0538, a variant which has an amino acid sequence having at least 70% identity to said protein and retains the biological activity thereof, or a fragment of said protein or variant which retains the biological activity thereof, or a functional derivative or salt of said protein, variant or fragment.

The present invention further comprehends methods for the treatment of a subject in need of treatment for the effects of neurotoxicity, stroke, hypoxia, or ischemia, comprising regulating in said subject the level of expression of any of the polynucleotides of the invention , so as to thereby treat the subject, preferably preferably polynucleotides comprising SEQ ID Nos: 49, 50, 51, 65, 67, 85, 87, 94–100, most preferably polynucleotides comprising SEQ ID No: 94 (corresponding to KIAA0538).

The present invention further comprehends methods for the treatment of a subject in need of treatment for the effects of neurotoxicity, stroke, hypoxia, or ischemia, comprising administering to said subject a polypeptide encoded by a cDNA selected from SEQ ID NO:65 or KIAA0284, a variant which has an amino acid sequence having at least 70% identity to said protein and retains the biological activity thereof, or a fragment of said protein or variant which retains the biological activity thereof, or a functional derivative or salt of said protein, variant or fragment.

The present invention further comprehends, as a preferred embodiment, the treatment of a subject in need of treatment for the effects of neurotoxicity, stroke, hypoxia, or ischemia, comprising administering to said subject a compound for inhibiting a polypeptide comprising a protein encoded by a cDNA selected from SEQ ID No:94 or KIAA0538, a variant which has an amino acid sequence having at least 70% identity to said protein and retains the biological activity thereof, or a fragment of said protein or variant which retains the biological activity thereof, or a functional derivative or salt of said protein, variant or fragment.

The present invention further comprehends methods for diagnosing cells which have been subjected to a neurotoxic insult, hypoxia and/or ischemia, comprising assaying for RNA comprising a sequence of any one of SEQ 1–131, preferably RNA comprising a sequence of any one of SEQ ID NOs:49, 50, 51, 65, 67, 85, 87, 94–100, most preferably RNA comprising a sequence of any one of SEQ ID NOs: 65, or 94, or for the expression product of a gene in which one of said sequences is a part, the change in amount of said RNA or expression product as compared to a control indicating the likelihood that such cells have been subjected to hypoxia or ischemia.

The present invention further comprehends methods of screening for a neuroprotective compound comprising testing the ability of the compound to upregulate or downregulate a gene which is transcribed to an RNA containing a sequence of any of SEQ ID NOs: 1–131, preferably any of SEQ ID NOs: 49, 50, 51, 65, 67, 85, 87 and 94–100, most preferably downregulate the transcription of SEQ ID No:94 or KIAA0538 or upregulate the transcription of SEQ ID No65 or KIAA 0284.

The present invention further comprehends methods of identifying a neuroprotective compound or screening for a neuroprotective compound comprising testing the ability of the compound to inhibit or enhance the activity of a polypeptide which is encoded by a polynucleotide of any of SEQ ID NOs: 1–131, as compared to a control, preferably SEQ ID NOs: 49, 50, 51, 65, 67, 85, 87 and 94–100, most preferably to inhibit SEQ ID NO 94, even more preferably wherein the compound is screened for the ability to inhibit a $Ca^{2+}$ promoted Ras inactivator encoded by a member of the KIAA0538 gene family; another preferred embodiment is wherein the compound is screened for the ability to activate or enhance the activity of a polypeptide encoded by KIAA0284.

The present invention further comprehends methods for screening for a compound or identifying a compound which induces or inhibits apoptosis after exposure of mammalian cells, preferably neural cells, to a neurotoxic insult, comprising the step of exposing the cells to the test compound and testing the change in expression, as compared to a control, of any one of the polynucleotides of the invention, preferably the change in expression of any member of the KIAA0538 gene family or the expression of KIAA0284.

The present invention further comprehends methods for screening for a compound or identifying a compound which induces or inhibits apoptosis after exposure of mammalian cells, preferably neural cells, to a neurotoxic insult, comprising the step of exposing the cells to the test compound and testing the change in activity of any one of the polypeptides of the invention, as compared to a control, preferably where the compound is screened for the ability to inhibit a $Ca^{2+}$ promoted Ras inactivator encoded by a member of the KIAA0538 gene family.

The present invention further comprehends methods for screening for a compound or identifying a compound capable of exerting a neuroprotective effect that ameliorates or diminishes the damage induced by a neurotoxic insult, comprising the step of screening for the ability of the compound to alter the level of expression of any of the polynucleotides of the invention, compared to a control, testing the compound for its ability to inhibit the expression of any polynucleotide of the KIAA0538 gene family.

The present invention further comprehends methods for screening for a compound or identifying a compound capable of exerting a neuroprotective effect that ameliorates or diminishes the damage induced by a neurotoxic insult, comprising the step of screening for the ability of the compound to alter the activity by enhancement or inhibition of any one of the polypeptides of the invention, preferably wherein the compound is screened for its ability to inhibit the activity of a $Ca^{2+}$ promoted Ras inactivator encoded by a member of the KIAA0538 gene family.

The present invention further comprehends methods for screening for a compound or identifying a compound which up-regulate or downregulate a gene, the improvement wherein said gene is a gene which is transcribed to an RNA complementary to any of the polynucleotides of the invention.

The present invention further comprehends methods for screening for or identifying a neuroprotective compound which specifically inhibits the polypeptide product of KIAA0538 gene which comprises:

(a) contacting cells expressing DNA encoding the KIAA0538 gene under conditions permitting expression of the DNA; and (b) determining if the compound inhibits the polypeptide as compared to a control; preferably the cells in this method are either transfected with the KIAA0538 gene or endogenously express the KIAA0538 gene, most preferably the cells are neuronal cells.

The present invention further comprehends a method of preparing a pharmaceutical composition which comprises the steps of:

(a) obtaining a compound which specifically inhibits the activity of the polypeptide product of the KIAA0538 gene; and (b) admixing said compound with a pharmaceutically acceptable carrier. The inhibitory compound may be obtained by using one of the screening assay methods disclosed herein for identifying such compounds.

The compositions and methods of invention can be used to treat the adverse consequences of central nervous system injuries that result from any of a variety of conditions. Thrombus, embolus, and systemic hypotension are among the most common causes of cerebral ischemic episodes. Other injuries may be caused by hypertension, hypertensive cerebral vascular disease, rupture of an aneurysm, an angioma, blood dyscrasias, cardiac failure, cardiac arrest, cardiogenic shock, septic shock, head trauma, spinal cord trauma, seizure, bleeding from tumor, or other blood loss. Where the ischemia is associated with stroke, it can be either global or focal ischemia, as defined below.

The present invention is additionally directed to pharmaceutical compositions which include the nucleic acids, proteins or polypeptides in accordance with the present invention, along with pharmaceutically acceptable carriers or excipients.

In addition, the present invention is directed to knockout or transgenic non-human animals, in which a gene identified by the present invention has been introduced or knocked out.

DETAILED DESCRIPTION OF PREFERRED EMBODIMENTS

I. Definitions

Figure 1:
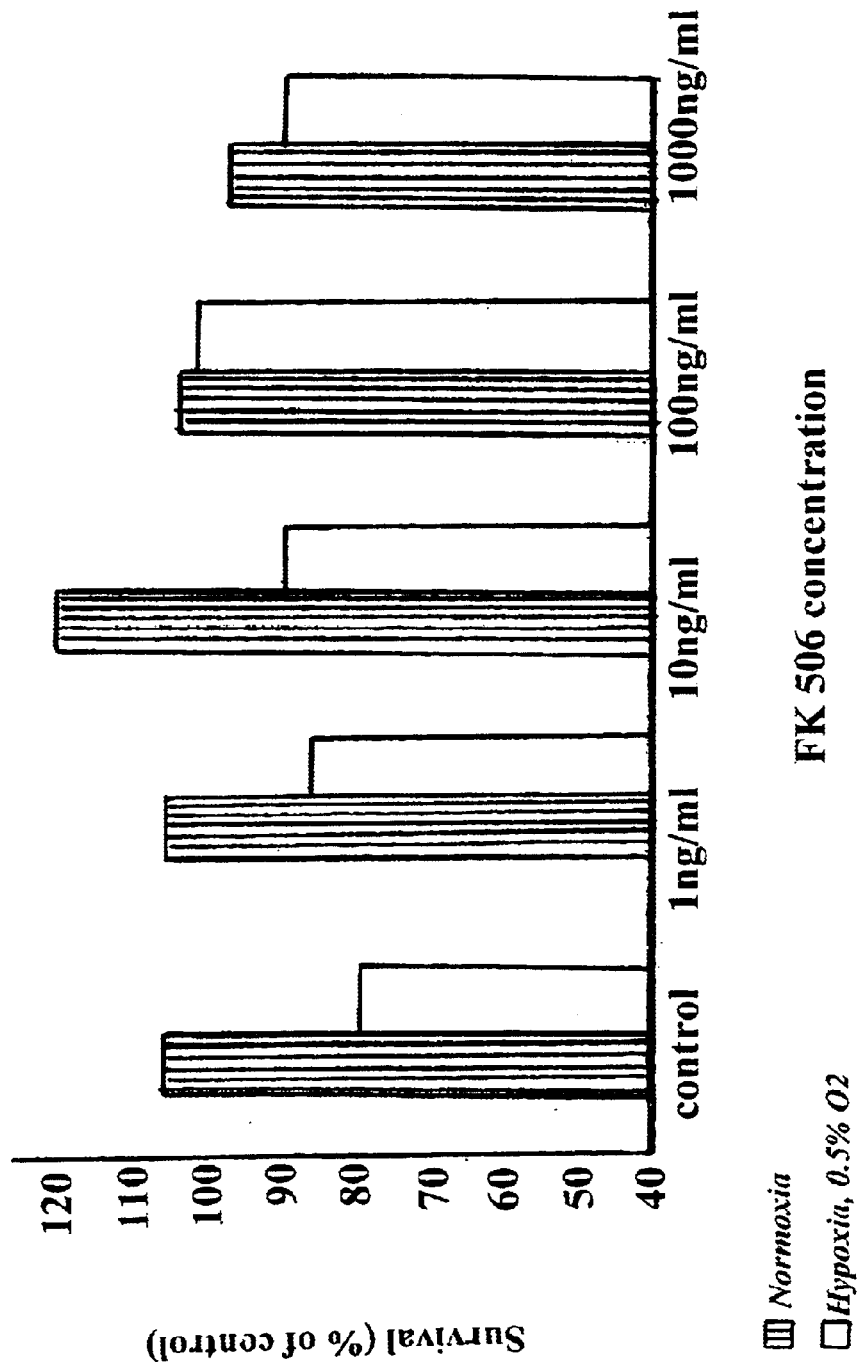
FIG. 1 is a graph showing the effect of FK506 on primary neurons undergoing 16 h hypoxia treatment. An optimal neuroprotective effect is achieved after 16 h hypoxia in the presence of 100 ng/mL of FK506.

The following definitions apply to the terms used in the present specification and claims:

The term "gene" refers to the genomic nucleotide sequence which is transcribed to a full-length RNA. Such RNA molecules may be converted into corresponding cDNA molecules by techniques well known to the art of recombinant DNA technology. The term "gene" classically refers to the genomic sequence, which, upon processing, can produce different RNAs, e.g., by splicing events. However, for ease of reading, any full-length counterpart RNA sequence will also be referred to by shorthand herein as a "gene".

The term "neurotoxic stress" as used herein is intended to comprehend any stress that is toxic to normal neural cells. Such stress may be hypoxia or hyperoxia or ischemia or trauma, or it may involve subjecting the cells to a substance that is toxic to the cells in vivo, such as glutamate or dopamine or the A protein. The neurotoxic substance may be endogenous or exogenous and the term neurotoxic is also intended to comprehend exposure to various known neurotoxins including organophosphorous poisoning, or any other insult of this type.

By "ischemic episode" is meant any circumstance that results in a deficient supply of blood to a tissue. Cerebral ischemic episodes result from a deficiency in the blood supply to the brain. The spinal cord, which is also part of the central nervous system, is equally susceptible to ischemia resulting from diminished blood flow. An ischemic episode may be caused by a constriction or obstruction of a blood vessel, as occurs in the case of a thrombus or embolus. Alternatively, the ischemic episode can result from any form of compromised cardiac function, including cardiac arrest. It is expected that the invention will also be useful for treating injuries to the central nervous system that are caused by mechanical forces, such as a blow to the head or spine. Trauma can involve a tissue insult such as an abrasion, incision, contusion, puncture, puncture, compression, etc., such as can arise from traumatic contact of a foreign object with any locus of or appurtenant to the head, neck, or vertebral column. Other forms of traumatic injury can arise from constriction or compression of CNS tissue by an inappropriate accumulation of fluid (for example, a blockade or dysfunction of normal cerebrospinal fluid or vitreous humor fluid production, turnover, or volume regulation, or a subdural or intracranial hematoma or edema). Similarly, traumatic constriction or compression can arise from the presence of a mass of abnormal tissue, such as a metastatic or primary tumor.

By "focal ischemia" as used herein in reference to the central nervous system, is meant the condition that results from the blockage of a single artery that supply blood to the brain or spinal cord, resulting in the death of all cellular elements (pan-necrosis) in the territory supplied by that artery.

By "global ischemia" as used herein in reference to the central nervous system, is meant the condition that results from general diminution of blood flow to the entire brain, forebrain, or spinal cord, which causes the death of neurons in selectively vulnerable regions throughout these tissues. The pathology in each of these cases is quite different, as are the clinical correlates. Models of focal ischemia apply to patients with focal cerebral infarction, while models of global ischemia are analogous to cardiac arrest, and other causes of systemic hypotension The term "Expressed Sequence Tag" or "EST" refers to a partial cDNA sequence of about 150 to 500, more preferably about 300, sequential nucleotides of a longer sequence obtained from a cDNA library prepared from a selected cell, cell type, tissue type, organ or organism which longer sequence corresponds to an mRNA (or other full-length RNA) transcribed in the above mentioned library sources. One or more libraries made from a single tissue type typically provide many different (i.e., unique) ESTs and potentially the full complement of all possible ESTs representing all cDNAs, e.g., 50,000–100,000 in an animal such as a human. Further background and information on the construction of ESTs is described in Adams et al (1991) and International Application Number PCT/US92/05222 (Jan. 7, 1993).

The term "apoptosis" is particularly defined as execution of built-in cell death program resulting in chromatin fragmentation into membrane-bound particles, changes in cell cytoskeleton and membrane structure and subsequent phagocytosis of apoptotic cell by other cells. However, as used herein, it should be understood that this term should be construed more broadly as encompassing neuronal cell death, whether or not that cell death is strictly by means the apoptotic process described above.

Two proteins are "cognate" if they are produced in different species, but are sufficiently similar in structure and biological activity to be considered the equivalent proteins for those species. Two proteins may also be considered cognate if they have at least 50% amino acid sequence identity (when globally aligned with a pam250 scoring matrix with a gap penalty of the form $q+r(k-1)$ where k is the length of the gap, $q=-12$ and $r=-4$; percent identity= number of identities as percentage of length of shorter sequence) and at least one biological activity in common. Similarly, two genes are cognate if they are expressed in different species and encode cognate proteins.

Whenever used in this invention "KIAA0538" (also referred to as "CAPRI") is defined as: any member of the KIAA0538 gene family, either full-length, mutant, splice variant, as a chimera with other proteins, or a polypeptide or biologically active fragment or domain of KIAA0538, or of any member of the KIAA0538 gene family having similar biological activity. KIAA0538 or KIAA0538 gene family member may be present in different forms, including: soluble protein; membrane-bound; bead-bound; or any other form of presenting KIAA0538 protein or fragments and polypeptides derived therefrom.

II. Gene Discovery Techniques

Two different techniques were used to identify genes that are involved in stroke response and/or regulated by FK506. The first technique is known as microarray hybridization (differential profiling). It was performed using two different types of microarrays: the rat "Stroke Chip" human "Apoptosis Chip" or "HAP Chip". The second technique is direct functional selection of genes which confer protection of neuron-like cells from genotoxic stressed as full-length cDNAs or as their fragments expressed either in sense or antisense orientation (functional profiling).

In the chip techniques, cDNA clones are arranged in a microarray on a chip substrate. The peculiarity of the the HAP chip is that printed cDNA clones are selected by above-mentioned functional profiling. Thus, in the HAP Chip, the cDNA fragments are those that correspond to genes with pro- or anti-apoptotic activity.

In the Stroke Chip, the cDNA fragments are those that correspond to genes that are believed to be stroke specific. They are obtained from brain tissue of rats subjected to MCAO and from primary neurons cultured in vitro under hypoxic conditions.

The cDNA libraries that served a source for the clones printed on the "Stroke chip" were prepared by two different techniques. First, by subtractive hybridization (by SSH) to enrich for clones differentially expressed in ischemic rat brains and hypoxic neurons and sequence-dependent gene identification (SDGI) to ensure maximal library comlexity and minimal redundancy. The clones originating from these two cDNA libraries are combined on the same stroke chip.

The expression libraries for functional profiling are made by cloning total cellular cDNA into retroviral expression vectors. The clones of such library may contain either full-length cDNA either in sense or in the antisense orientation or cDNA fragments also expressed either as an "antisense RNA" or it can make a short protein that can act as a dominant negative peptide. When the cDNA is expressed in the antisense orientation or as short peptide,the result will be inhibition of the expression or activity of the matching endogenous gene. A plasmid DNA pool is prepared from the bacteria and used for the introduction of the library into mammalian mammalian retroviral packaging cells of choice. The rescued recombinant retrovirus mixture is further used for transduction of the target cells. The cDNA fragment that is expressed by such mammalian cells can potentially inhibit or stimulate the expression of a specific endogenous gene or the function of the protein expressed by such a gene. The pool of mammalian cells is subjected to a certain selection process in which the activity of a number of genes is necessary for the cells to show a specific phenotype, after a specific induction, that can be followed experimentally. Thus, if the expression of a key gene is inhibited, the phenotype does not show for that cell. The selection process allows the selection of exactly these types of cells. This is followed by identification of the cDNA fragment that was present in the expression vector that was found in the cell. The identity of this cDNA fragment is indicative of the identity of the inhibited gene, thus identifying it as a key gene required for the change in phenotype. In the direct functional profiling method, these identified fragments are used as the candidates for further analysis.

Alternatively, the rescued cDNA clones are used for the printing of HAP chip. Further implication of such a chip in differential profiling enables a direct identification of "functional" genes differentially expressed in pathological conditions. The chips may be used for differential hybridization experiments. Thus, cells, either in vivo or in vitro, may be subjected to a developmental, physiological, pharmacological or other cued event that will cause genes to be activated or repressed in response thereto. Such a cued event may be mechanical, chemical, toxic, pharmaceutical or other stress, hormones, physiological disorders or disease. A library of clones is made from the cDNA expressed by the cells subjected to such a cued event. These clones may then be labeled and used as a first probe. A control probe is made from the cDNA of cells that have not been subjected to the cued event. The two probes are labeled with first and second different fluorescent reporters. A mixture of the labeled cDNAs from the two cell types is added to the array of polynucleotides on the chip, under conditions that result in hybridization of the cDNAs to the complementary-sequence polynucleotides in the array. The array is then examined by fluorescence under fluorescence excitation conditions in which (i) polynucleotides in the array that are hybridized predominantly to cDNAs derived from one of the first or second cell types give a distinct first or second fluorescence emission color, respectively, and (ii) polynucleotides in the array that are hybridized to substantially equal numbers of cDNAs derived from the first and second cell types give a distinct combined fluorescence emission color, respectively. The relative expression of each polynucleotide in the array on the chip can then be determined by the observed fluorescence emission color of each spot. Thus, one can rapidly determine which genes are differentially expressed between the control cells and the cells which have been subjected to the cued event and one can readily determine if the gene has been upregulated or downregulated. This gene expression array technology is disclosed, for example in U.S. Pat. No. 5,807,522, the entire contents of which are hereby incorporated herein by reference.

In the production of the Stroke Chip, the cDNA microarray was constructed by combining various types of libraries. An ischemia (stroke) model was created in SD and SHR rats by permanent middle cerebral artery occlusion (MCAO). Control rats of the same strain were subjected to a sham operation (Sham). Half of the rats of each group were given FK506 treatment at 0 hour. Subtraction libraries comprised: genes expressed in the MCAO rats but not in the sham operated rats (MCAO—Sham); and those genes expressed in the MCAO rats treated with FK506 (taken at 3 hours and 6 hours after FK506 treatment) but not in the MCAO treated rats which had not been exposed to FK506 treatment ([MCAO+FK506]–[MCAO]).

Another library included in the Stroke Chip was derived from in vitro treatment of primary neurons from the cerebellum of 7 day rat pups. The cells were subjected to hypoxia (0.5% $O_2$) for 16 hours. The cells under hypoxia and control cells under normal oxygen concentration (normoxia) were treated with FK506 (100 ng/ml) at 0 hour and the cDNA extracted after 16 hours. A subtraction library was made from the cDNA fragments expressed in the FK506 treated cells under hypoxia but not in the FK506 treated cells under normoxia ([Hypoxia+FK506]–[Normoxia+FK506]).

Additional libraries were generated by sequence-dependent gene identification (SDGI). This technique is described in U.S. application Ser. No. 09/538,709, now PCT publication No. WO 01/75180, the entire contents of which are hereby incorporated herein by reference. SDGI libraries were prepared from brain tissues of rats subjected to MCAO, MCAO rats three and six hours after treatment with FK506, and sham operated rats three and six hours after treatment with FK506. SDGI libraries were prepared from primary neurons that were subjected to hypoxia for 16 hours in the in vitro experiments and from primary-neurons, pretreated with FK506 and subjected to hypoxia for 16 hours.

Polynucleotides from each of these libraries were combined onto the Stroke Chip, which contained about 10,000 clones.

In the HAP Chip, the clones were selected from among seven different libraries prepared using different functional profiles obtained by functional selection. A library of human BE2C neuroblastoma cells was prepared having inserted therein expression vectors with cDNA derived from human A172 or T98G glioma cells. The cells were subjected either to dopamine, glutamate or hypoxia. In all cases, the treatment in the selection type normally causes cell death. Cells that survived the selection by virtue of the library clone expression were selected and the cDNA fragments found in the expression vectors were recovered as a pool. This cDNA pool is highly enriched for cDNA fragments of genes required for cell death caused by the treatments mentioned in the selection type or by full-length cDNA required for cell survival under the conditions applied. Each cDNA pool was cloned to make a small library from which clones were taken for printing on the HAP chip.

Similarly, human HeLa cells were transformed with the TKO expression libraries (coassigned U.S. Pat. No. 6,057, 111; Deiss and Kimchi, 1991, Science, 252, 117–120) with antisense cDNA derived from HeLa cells therein. The library-transfected cells were subjected either to either irradiation, or taxol, or serum starvation, or serum starvation in conjunction with FAS antibody treatment. Again, the selection type normally causes cell death. Cells that survived the selection were selected and the cDNA fragments found in the expression vectors were recovered as a pool. Clones from these pools were also taken for printing on the HAP Chip.

III. Novel Polynucleotide Sequences

Once candidate sequences are identified by one or more of the three selection processes, they were subjected to a bioinformatics analysis to annotate them and to identify if they are part of any known genes or ESTs or to determine whether they may be part of novel genes.

Polynucleotides that are selected on the basis of the stroke chip model discussed above originated as rat cDNA. Thus, when the positively identified polynucleotides from the array are sequenced, they will correspond to at least a fragment of a rat cDNA whose expression in neural cells is modulated when those cells are subjected to neurotoxic stress. Polynucleotides that are selected on the basis of the HAP chip model or the direct functional profiling originated as human cDNA. Thus, when the positively identified polynucleotides from the HAP chip array or directly identified from the functional profiling are sequenced, they will correspond to at least a fragment of a human cDNA whose expression in neural cells is modulated when those cells are subjected to neurotoxic stress.

The polynucleotides determined in these assays fall within two categories. The first have novel sequences which are not found in any sequence databank or not substantially homologous to any sequence found in any sequence databank, or at least are not homologous to any sequence which is identified as being part of a known gene or having any known function. Some of the polynucleotides discussed in the present specification have such novel sequences, SEQ ID Nos: 1–48, 52–64, 66, 68–84, 86, 88–93, 101–131. The second is sequences that turn out to be a part of a known gene or are substantially homologous to a part of a known gene in another species, e.g. KIAA sequences, but were not previously known to have a connection to hypoxia or stroke. Some of the polynucleotides discussed in the present specification have such known sequences. Such polynucleotides have SEQ ID Nos: 49–51, 65, 67, 85, 87, 94–100.

To the extent that the sequence is positively identified, the present invention comprehends that sequence, as well as any naturally-occurring polynucleotide that includes that sequence as a part thereof. The sequence per se has utility based on the fact that it has been identified on the basis of differential expression in cells subjected to neurotoxic stress. It can be used in diagnostic processes and kits for determining whether any given neurological cells have been subjected to neurotoxic stress or whether neurons in vivo have been protected from neurotoxicity by some means. Even when such sequences are rat sequences, there is real-world utility for the purpose of medical research for determining in a rat model which cells have been subjected to neurotoxic stress and which cells may have been protected from neurotoxic stress when subjected to a treatment protocol in a rat model. By using the novel sequence as a probe, or a portion thereof as a oligonucleotide probe, one can identify the places in the brain (whether the brain is a rat brain when the sequence is a rat sequence or a human brain when the sequence is a human sequence) where the cDNA including the sequence is expressed and whether or not, or in what degree, it is expressed when subjected to various treatment protocols.

Human genes may be directly discovered using the HAP chip or functional profiling or indirectly discovered by determining the human gene which corresponds to the rat gene discovered using the stroke chip. Such human genes are also useful for determining whether human neural cells have been subjected to neurotoxic stress, for example in diagnosing whether or not a patient has suffered a stroke. As will be discussed in greater detail below, it is a procedurally routine matter to determine a cognate human gene based on the sequence of a rat gene. Thus, regardless of whether or not one knows the actual sequence of the corresponding human gene, the rat gene has utility as a probe for seeking and identifying the corresponding human gene which, when identified, will have its own utility.

The positively identified polynucleotide sequences are ESTs. The location of an EST in a full-length cDNA is determined by analyzing the EST for the presence of coding sequence. A conventional computer program is used to predict the extent and orientation of the coding region of a sequence (using all six reading frames). Based on this information, it is possible to infer the presence of start or stop codons within a sequence and whether the sequence is completely coding or completely non-coding or a combination of the two. If start or stop codons are present, then the EST can cover both part of the 5'-untranslated or 3'-untranslated part of the mRNA (respectively) as well as part of the coding sequence. If no coding sequence is present, it is likely that the EST is derived from the 3' untranslated sequence due to its longer length and the fact that most cDNA library construction methods are biased toward the 3' end of the mRNA. It should be understood that both coding and non-coding regions may provide ESTs equally useful in the described invention.

Methods for obtaining complete gene sequences from ESTs are well-known to those of skill in the art. See, generally, Sambrook et al, (1989) and Ausubel et al (1994–2000). Briefly, one suitable method involves purifying the DNA from the clone that was sequenced to give the EST and labeling the isolated insert DNA. Suitable labeling systems are well known to those of skill in the art. See, e.g., Davis et al (1986). The labeled EST insert is then used as a probe to screen a lambda phage cDNA library or a plasmid cDNA library, identifying colonies containing clones related to the probe cDNA that can be purified by known methods. The ends of the newly purified clones are then sequenced to identify full-length sequences and complete sequencing of full-length clones is performed by enzymatic digestion or primer walking. A similar screening and clone selection approach can be applied to clones from a genomic DNA library. The entire naturally-occurring cDNA or gene sequence, including any allelic variations thereof, all will have the same utility as discussed above for the identified polynucleotide.

The complete gene sequence of naturally-occurring variants of the gene in question, such as, for example, allelic variations, may be determined by hybridization of a cDNA library using a probe which is based on the identified polynucleotide, under highly stringent conditions or under moderately stringent conditions. Stringency conditions are a function of the temperature used in the hybridization experiment and washes, the molarity of the monovalent cations in the hybridization solution and in the wash solution(s) and the percentage of formamide in the hybridization solution. In general, sensitivity by hybridization with a probe is affected by the amount and specific activity of the probe, the amount of the target nucleic acid, the detectability of the label, the rate of hybridization, and the duration of the hybridization. The hybridization rate is maximized at a Ti (incubation temperature) of 20–25° C. below Tm for DNA:DNA hybrids and 10–15° C. below Tm for DNA:RNA hybrids. It is also maximized by an ionic strength of about 1.5M Na$^+$. The rate is directly proportional to duplex length and inversely proportional to the degree of mismatching.

Specificity in hybridization, however, is a function of the difference in stability between the desired hybrid and "background" hybrids. Hybrid stability is a function of duplex length, base composition, ionic strength, mismatching, and destabilizing agents (if any).

The Tm of a perfect hybrid may be estimated for DNA:DNA hybrids using the equation of Meinkoth et al (1984), as $$Tm=81.5° C.+16.6(\log M)+0.41(\% GC)-0.61(\% form)-500/L$$

and for DNA:RNA hybrids, as $$Tm=79.8° C.+18.5(\log M)+0.58(\% GC)-11.8(\% GC)^2-0.56(\% form)-820/L$$

where

M, molarity of monovalent cations, 0.01–0.4 M NaCl,

% GC, percentage of G and C nucleotides in DNA, 30%–75%,

% form, percentage formamide in hybridization solution, and

L, length hybrid in base pairs.

Tm is reduced by 0.5–1.5° C. (an average of 1° C. can be used for ease of calculation) for each 1% mismatching.

The Tm may also be determined experimentally. As increasing length of the hybrid (L) in the above equations increases the Tm and enhances stability, the full-length rat gene sequence can be used as the probe.

Filter hybridization is typically carried out at 68° C., and at high ionic strength (e.g., 5–6×SSC), which is non-stringent, and followed by one or more washes of increasing stringency, the last one being of the ultimately desired stringency. The equations for Tm can be used to estimate the appropriate Ti for the final wash, or the Tm of the perfect duplex can be determined experimentally and Ti then adjusted accordingly.

Hybridization conditions should be chosen so as to permit allelic variations, but avoid hybridizing to other genes. In general, stringent conditions are considered to be a Ti of 5° C. below the Tm of a perfect duplex, and a 1% divergence corresponds to a 0.5–5° C. reduction in Tm. Typically, rat clones were 95–100% identical to database rat sequences, and the observed sequence divergence may be artifactual (sequencing error) or real (allelic variation). Hence, use of a Ti of 5–15° C. below, more preferably 5–10° C. below, the Tm of the double stranded form of the probe is recommended for probing a rat cDNA library with rat EST probes. However, when probing for a human gene cognate, more moderate stringency hybridization conditions should be used.

As used herein, highly stringent conditions are those which are tolerant of up to about 15% sequence divergence, while moderately stringent conditions are those which are tolerant of up to about 30–35% sequence divergence. Without limitation, examples of highly stringent (5–15° C. below the calculated Tm of the hybrid) and moderately stringent (15–20° C. below the calculated Tm of the hybrid) conditions use a wash solution of 0.1× SSC (standard saline citrate) and 0.5% SDS at the appropriate Ti below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6× SSC (or 6×SSPE), 5× Denhardt's reagent, 0.5% SDS, 100 µg/ml denatured, fragmented salmon sperm DNA at an appropriate incubation temperature Ti.

Once any such naturally-occurring DNA is identified, it can be tested by means of routine experimentation to determine whether it is differentially expressed in the neuronal cells in which it naturally occurs when subjected to neuro-toxic stress. The present invention is intended to comprehend any such naturally-occurring DNA which binds to an EST of the present invention or any oligonucleotide fragment thereof, preferably having at least 20, more preferably at least 50, contiguous nucleic acids, under highly stringent conditions or under moderately stringent conditions, which identified DNA molecules are determined to be differentially expressed in the neural cells in which they naturally occur when such neural cells are subjected to neurotoxic stress. Any such identified DNA molecules would have the same utility as discussed above for the identified polynucleotide.

If the full-length sequence identified is a rat gene sequence or a sequence of any mammalian gene other than human, the cognate human gene sequence can be readily obtained, as would be readily appreciated by those of skill in the art. Comparison of known cognate protein and gene sequences between rat and human shows a high level of sequence identity, mostly on the order of 70% or higher. The cognate human gene sequence is quite readily identified and determined as long as there is a high level of sequence identity to the rat gene sequence.

While a rat EST sequence would be used to probe a rat cDNA library for a full-length cDNA sequence, and could even be used to probe human cDNA libraries, it would be expected that there would be some sequence divergence, especially at the EST sequence level, between cognate rat and human DNAs, which sequence divergence may be possibly as much as 25–50%. Preferably, the rat sequence used as a probe is from the coding region of the rat cDNA, as 5'- or 3'-uncoded region often lack significant homology among different mammalian species.

If a partial human cDNA is obtained, it may be used to isolate a larger human cDNA, and the process repeated as needed until the complete human cDNA is obtained.

For cross-species hybridization, such as to obtain the cognate human gene sequence from the rat gene sequence, the Ti should be reduced further, by about 0.5–1.5° C., e.g., 1° C., for each expected 1% divergence in sequence. The degree of divergence may be estimated from the known divergence of the most closely related pairs of known genes from the two species.

If the desired degree of mismatching results in a wash temperature less than 45° C., it is desirable to increase the salt concentration so a higher temperature can be used. Doubling the SSC concentration results in about a 17° C. increase in Tm, so washes at 45° C. in 0.1×SSC and 62° C. in 0.2×SSC are equivalent (1×SSC=0.15 M NaCl, 0.015M trisodium citrate, pH 7.0).

The person skilled in the art can readily determine suitable combinations of temperature and salt concentration to achieve these degrees of stringency.

Examples of successful cross-species-hybridization experiments include Braun et al (1989) (mouse v. human), Imamura et al (1991) (human v. rat), Oro et al (1988) (human v. Drosophila), Higuti et al (1991) (rat v. human), Jeung et al (1992) (rat, bovine v. human), Iwata et al (1992) (human v. mouse), Libert et al (1992) (dog v. human), Wang et al (1993) (human v. mouse), Jakubiczka et al (1993) (human v. bovine), Nahmias et al (1991) (human v. mouse), Potier et al (1992) (rat v. human), Chan et al (1989) (human v. mouse), Hsieh et al (1989) (human, mouse v. bovine), Sumimoto et al (1989) (human v. mouse), Boutin et al (1989) (rat v. human), He et al (1990) (human, rat v. dog, guinea pig, frog, mouse), Galizzi et al (1990) (mouse v. human). See also Gould et al (1989).

In general, for cross-species hybridization, Ti=25–35° C. below Tm. Wash temperatures and ionic strengths may be adjusted empirically until background is low enough.

Any non-rat mammalian sequences obtained from such hybridization experiments, which sequences test positive for the ability to be differentially expressed when the neuronal cells in which they naturally occur are subjected to neurotoxic stress, are also encompassed by the present invention.

Fragments of any such naturally-occurring sequences also have utility and are intended to be encompassed by the present invention. Fragments of preferably at least 20, more preferably at least 50, nucleotides in length can be used as probes for the diagnostic assays described above.

Polynucleotide sequences that are complementary to any of the sequences or fragments encompassed by the present invention discussed above are also considered to be part of the present invention. Whenever any of the sequences discussed above are produced in a cell, the complementary sequence is concomitantly produced and, thus, the complementary sequence can also be used as a probe for the same diagnostic purposes.

IV. Novel Proteins Encoded by Genes of Section III

Once the sequence of any full-length cDNA is obtained, the protein encompassed thereby is readily determinable by analysis of the sequence to find the start and stop codons and then decoding the amino acid sequence encoded by the cDNA. Thus, the present invention also encompasses any protein encoded by a full-length cDNA encompassed by the present invention as discussed above. Such proteins can be used for the same diagnostic utility, as discussed above for the polynucleotides, as they will be differentially expressed to the same degree that the corresponding cDNA is differentially expressed. They can be used to make a diagnostic tool which can be used to determine their presence in a cell. Thus, for example, they can be used to raise antibodies that could be used in such a diagnostic assay for the presence of such a protein. Such an assay would be useful to determine whether any given cell had been subjected to neurotoxic stress. Such proteins can also be used for any of the utilities discussed hereinbelow in the section related to methods of use.

Analogs of a protein or polypeptide encoded by the DNA sequences discovered in the assays described herein is also comprehended by the present invention. Preferably, the analog is a variant of the native sequence which has an amino acid sequence having at least 70% identity to the native amino acid sequence and retains the biological activity thereof. More preferably, such a sequence has at least 85% identity, at least 90% identity, or most preferably at least 95% identity to the native sequence.

The term "sequence identity" as used herein means that the sequences are compared as follows. The sequences are aligned using Version 9 of the Genetic Computing Group's GAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

Analogs in accordance with the present invention may also be determined in accordance with the following procedure. Polypeptides encoded by any nucleic acid, such as DNA or RNA, which hybridize to the complement of the native DNA or RNA under highly stringent or moderately stringent conditions, as long as that polypeptide maintains the biological activity of the native sequence are also considered to be within the scope of the present invention. Preferably, such nucleic acids hybridizing to the complement of the polynucleotides of the present invention under the specified conditions are naturally occurring nucleic acids, which may or may not be produced in cells of the same species as the original polynucleotides. As with any other analog, such polypeptide must retain the biological activity of the original polypeptide.

The term "active fragments" is intended to cover any fragment of the proteins identified by means of the present invention that retain the biological activity of the full protein. For example, fragments can be readily generated from the full protein where successive residues can be removed from either or both the N-terminus or C-terminus of the protein, or from biologically active peptides obtained therefrom by enzymatic or chemical cleavage of the polypeptide. Thus, multiple substitutions are not involved in screening for active fragments. If the removal of one or more amino acids from one end or the other does not affect the biological activity after testing in the standard tests, discussed herein, such truncated polypeptides are considered to be within the scope of the present invention. Further truncations can then be carried out until it is found where the removal of another residue destroys the biological activity.

"Functional derivatives" as used herein covers chemical derivatives which may be prepared from the functional groups which occur as side chains on the residues or the N- or C-terminal groups, by means known in the art, and are included in the invention as long as they remain pharmaceutically acceptable, i.e., they do not destroy the biological activity of the corresponding protein as described herein and do not confer toxic properties on compositions containing it. Derivatives may have chemical moieties, such as carbohydrate or phosphate residues, provided such a fraction has the same biological activity and remains pharmaceutically acceptable.

Suitable derivatives may include aliphatic esters of the carboxyl of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (e.g., that of seryl or threonyl residues) formed with acyl moieties. Such derivatives may also include for example, polyethylene glycol side-chains which may mask antigenic sites and extend the residence of the complex or the portions thereof in body fluids.

Non-limiting examples of such derivatives are described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidazoyl)propionic acid, chloroacetyl phosphate, B alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclodexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-[2-morpholinyl-(4-ethyl)] carbodiimide or 1-ethyl-3-(4-azonia-4,4-dimethlypentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

The term "derivatives" is intended to include only those derivatives that do not change one amino acid to another of the twenty commonly-occurring natural amino acids.

The term "salts" herein refers to both salts of carboxyl groups and to acid addition salts of amino groups of the complex of the invention or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must have substantially similar biological activity to the complex of the invention or its analogs.

V. Known Polynucleotides and Protein Sequences

After the polynucleotide sequences are identified following the gene discovery techniques discussed above, and these discovered sequences are subjected to bioinformatics review, it has been determined that many of these sequences appear in the sequence databanks and some are part of identified known genes with known function and encode known proteins. Once it is determined that an EST found by the gene discovery techniques of the present invention are part of a known gene, it is not necessary to go through the hybridization steps in order to find the full-length cDNA for such ESTs. Furthermore, in most cases, it will not be necessary to find the cognate human gene experimentally. If the rat EST is part of a known rat gene, it is likely that the cognate human gene is also known. If not, it may be determined by the techniques discussed hereinabove with respect to novel rat gene sequences.

As the protein encoded by the known gene is also known, it is not necessary to use the techniques discussed hereinabove for determining the sequence encoded by a polynucleotide sequence. However, to the extent that the protein is not known, the techniques discussed hereinabove with respect to novel polynucleotide sequences may also be used.

Any known allelic variants of the known gene would also be expected to have the properties discovered by the gene discovery techniques discussed herein and, therefore, are also considered to be part of the present invention. The existence of other naturally-occurring variants having the property of having its sequence modulated when subjected to neurotoxic stress may also be determined using hybridization experiments under highly stringent conditions or moderately stringent conditions, all as discussed in detail hereinabove with respect to the novel polynucleotide sequences.

Analogs, active fragments, functional derivatives and salts of the known proteins which retain the property of that protein for the purposes of the present invention (although not necessarily for the properties previously known for that protein) are comprehended by the present invention, if novel, and their use is considered to be part of the present invention.

VI. Utility of Good Genes and Bad Genes

The genes found in the in vivo experiment on the two chips which were upregulated by MCAO without FK506 treatment (vs. sham), but downregulated when treated with FK506 (vs MCAO without FK506), illustrate genes which contribute to the effects of stroke and which it would be desirable to downregulate in the treatment of stroke, or otherwise decrease the titer of the expression product of such genes or inactivate it at the site of the stroke. These genes will be referred to as "bad genes" herein. The utility of such bad genes and methods of use thereof will be discussed below The genes found in the in vivo experiment on the two chips that were downregulated by MCAO vs. sham but upregulated when the MCAO rats are treated with FK506, illustrate genes which contribute to the alleviation of the detrimental effects of stroke and which it would be desirable to upregulate or otherwise increase the titer of the expression product of such genes at the site of the stroke. These genes will be referred to as "good genes" herein. The utility of such good genes and methods of use thereof will be discussed below.

The genes found in the in vitro experiment on the Stroke chip that were upregulated in hypoxia cells sixteen hours after FK506 treatment are genes that contribute to the alleviation of the detrimental effects of stroke and therefore would fall into the category of good genes. Those that were downregulated after FK506 treatment contribute to the effects of stroke, although they are beneficially downregulated by FK506, and fall into the category of bad genes.

In the direct functional profiling assays, the inserted DNA fragments that protected the cells from death were functional either in effectively knocking out a gene that would otherwise have contributed to the cell death or being a complete cDNA of a protective gene by itself. If the original orientation of the sequence is antisense, its activity will be antisense, blocking expression from the sense sequence of the corresponding gene. Such genes fall into the category of bad genes. If the original orientation is sense, it may encode either a peptide having a dominant negative effect or the complete functional protein. If cDNAs codes for a protective dominant negative peptide that counteract with the normal function of the corresponding endogenous gene, the latter gene also falls in the category of bad genes. However, in some cases, short sense cDNA fragments may express a minimal active protein segment, thus falling in the category of good genes. cDNAs expressing full-length open reading frames in sense orientation also fall into the category of good genes. As indicated above, it is not always possible to determine directly from the results of the functional profiling tests whether the DNA fragments found are part of a good gene or a bad gene. Even more frequently, it may not be possible to directly determine whether DNA fragments identified in differential profiling are part of good genes or bad genes. It is reasonably certain, however, that the fragments so identified are one or the other as their expression has been significantly modulated based on the neurotoxic stress conditions to which the cells have been subjected, with or without FK506. Even a sham operation places neurotoxic stress on brain cells. However, by means of further experimentation, which experimentation would not be considered to be undue experimentation, one can determine whether the fragments are part of good genes or bad genes. Oneway to test whether the fragments are part of good genes or bad genes would be to knock out the gene of interest, either in a animal or by knocking out the gene by alternative method in the cell line being tested. In a cell line, the cells can then be tested with neurotoxic stress to determine whether the absence of that gene has a protective effect or enhances cell death. In a knockout mouse, similar tests can be conducted to see whether the absence of that gene has a protective or detrimental effect on the mouse when subjected to neurotoxic stress.

A gene can be knocked out in a cell line by means of homologous recombination or by transfecting the cell line with an antisense sequence which prevents the expression of that gene, or by expression of rationally designed dominant-negative mutant protein or by introduction of RNAi, all as is well known to those of ordinary skill in this art. A gene can be knocked out in an animal such as a mouse, by the techniques discussed below in Section XVII.

Another way is to overexpress the corresponding full-length cDNA either in animals (transgenic mice) or in cell line (transfection, transduction) and to test the effect of the overexpression of the gene, as regards protection from cell death or augmentation of cell death, under normal or stressful conditions.

Accordingly, even if it cannot be directly determined whether any of the DNA fragments of the present invention are parts of good genes or parts of bad genes, it is reasonably expected that they are parts of either one or the other, and, in either event, they have utility for the reasons discussed below. It can be determined whether they are good genes or bad genes without resorting to undue experimentation. Accordingly, such genes have utility and industrial applicability.

Good genes are useful as the protein encoded by such genes can be used to protect neural cells from neurotoxicity, to ameliorate the effects of hypoxia, ischemia, or other neurotoxic stressors, and ultimately in the therapeutic treatment of stroke, hypoxia and/or ischemia. Thus the genes, and the DNA encoding such a protein or active fragment or analog thereof, are useful in the recombinant production of such proteins or polypeptides. They are also useful as a target for assays for the discovery of drugs which selectively upregulate such genes or activate their protein products. The proteins encoded by such novel good genes, as well as active fragments thereof, analogs and functional derivatives thereof, are also part of the present invention and have utility to protect neural cells from neurotoxicity, to ameliorate the effects of hypoxia, ischemia, or other neurotoxic stressors, and ultimately in the therapeutic treatment of stroke, hypoxia and/or ischemia.

Good genes, whether novel or known, but whose relationship to neurotoxicity reported herein was previously unknown, may be used in novel processes which take advantage of these newly discovered properties. Thus, for example, the expression product of such genes, as well as active fragments, analogs and functional derivatives thereof, may be used to protect neural cells from neurotoxicity, to ameliorate the effects of hypoxia, ischemia, or other neurotoxic stressors, and ultimately for the treatment of the effects of stroke, hypoxia and/or ischemia by the therapeutic administration thereof in a manner which causes such product to be brought into the vicinity of the cells to be treated.

Bad genes, if their protein products are secreted into serum, are useful in that they can be used in diagnostic assays for cells that have been subjected to hypoxia, ischemia, and/or other neurotoxic stresses. If mRNA corresponding to such genes, or the translation product thereof, is found in the cells being assayed it is likely that they have been subjected to hypoxia, ischemia, and/or other neurotoxic stresses. If diagnosed pre-stroke, this may be predictive of incipient stroke. They are also useful as a target for assays for the discovery of drugs which selectively downregulate such genes or are otherwise dominant negative with respect to the expression of the gene product of such genes. Antisense RNA that prevents the expression of such gene is also part of the present invention and is useful to protect neural cells from neurotoxicity, to ameliorate the effects of hypoxia, ischemia, or other neurotoxic stressors, and ultimately for the treatment of the effects of stroke, hypoxia and/or ischemia.

Bad genes, whether novel or known but whose relationship to neurotoxic stresses including ischemic episodes as exemplified by, but not limited to the model of stroke reported herein, was previously unknown, may be used in novel processes which take advantage of these newly discovered properties. Antisense RNA having a sequence complementary to a portion of such a gene and that prevents the expression of such a gene may be produced and used therapeutically by administering same in a manner by which it enters cells which have been subjected to stroke, hypoxia, ischemia, and/or other neurotoxic stress in order to ameliorate the effects of such conditions. They may also be used in methods for assaying for drugs which downregulate such genes. To the extent that such proteins/polypeptides are enzymes, or ion channels, or transporters or other "druggable" entities, the present invention comprehends the protection of neural cells from neurotoxicity, the amelioration of the effects of hypoxia, ischemia, or other neurotoxic stress, and ultimately the therapeutic treatment of the effects of stroke, hypoxia, ischemia, and/or other neurotoxic stress by administering an inhibitor of such enzyme (or other druggable proteins, e.g. ion channel, or transporter, etc) in a manner that brings such inhibitor to the vicinity of the cells in which such enzyme has been upregulated.

It is known in the art, that in certain neurological diseases, for example, brain ischemia or stroke, the blood brain barrier (BBB) is relatively open compared to that of a normal subject, thus enabling penetration of even large molecules such as macromolecules, including antibodies into the brain, and subsequently allowing interaction of the latter with the target moieties. In this connection, the use of neutralizing therapeutic antibodies against the secreted protein products of bad genes is also contemplated by this invention Nevertheless, it will be appreciated by the skilled artisan that the use of small molecules in general, and particularly small molecules capable of penetration into the central nervous system is advantageous for treatment of the ischemic damage, neurotoxicity, and traumatic insults by inhibiting the genes or gene products of the present invention.

VII. Diagnostic Methods

Methods of detecting tissue hypoxia in mammalian tissue, or the fact that tissue has been subjected to another neurotoxic stress, are based on the use of the potentially secreted protein products of the bad genes as a diagnostic marker(s) for cells that have been subjected to hypoxia, ischemia, and/or other neurotoxic stresses. It is possible to determine the level of protein translation products corresponding to these bad genes, in normal tissue fluids as compared to hypoxic tissue fluids and, thus, determine the reference values of these bad genes protein products which are indicative of tissue hypoxia.

Furthermore, regardless of whether or not the gene or gene product has been designated as good or bad, that gene (or EST) can be used in the diagnostic methods of the present invention if it was found in the chip or functional experimentation reported herein to be modulated significantly upward after the cells have been subjected to neurotoxic stress, and particularly hypoxia. Any such gene may be considered to be a gene of interest for the purpose of the diagnostic assays reported herein.

The use of antibodies as diagnostics against the secreted protein products of bad genes is also contemplated by this invention.

Samples

The sample for use in the detection methods may be of any biological fluid or tissue which is reasonably expected to contain the the protein expressed from one of the above mentioned bad genes. Preferably, the sample isbody fluids of the subject being tested.

Analyte Binding Reagents

The assay target or analyte as a diagnostic marker is a secreted protein translation product of the gene of interest. When the assay target is a protein, the preferred binding reagent is an antibody, the specifically binding fragment of an antibody, or a molecule that has the antigen-binding portion of an antibody. The antibody may be monoclonal or polyclonal. It can be obtained by first immunizing a mammal with the protein target, and recovering either polyclonal antiserum, cr immunocytes for later fusion to obtain hybridomas, or by constructing an antibody phage library and screening the antibodies for binding to the target. The binding reagent may also be a binding molecule other than an antibody, such as a receptor fragment, an oligopeptide, or a nucleic acid. A suitable oligopeptide or nucleic acid may be identified by screening a suitable random library.

Signal Producing System (SPS)

In order to detect the presence, or measure the amount, of an analyte, the assay must provide for a signal producing system. (SPS) in which there is a detectable difference in the signal produced, depending on whether the analyte is present or absent (or, in a quantitative assay, on the amount of the analyte). The detectable signal may be one which is visually detectable, or one detectable only with instruments. Possible signals include production of colored or luminescent products, alteration of the characteristics (including amplitude or polarization) of absorption or emission of radiation by an assay component or product, and precipitation or agglutination of a component or product. The term "signal" is intended to include the discontinuance of an existing signal, or a change in the rate of change of an observable parameter, rather than a change in its absolute value. The signal may be monitored manually or automatically.

Labels

The component of the signal producing system which is most intimately associated with the diagnostic reagent for the analyte is called the "label". A label may be, e.g., a radioisotope, a fluorophore, an enzyme, a co-enzyme, an enzyme substrate, an electron-dense compound, an agglutinable particle, etc.

The radioactive isotope can be detected by such means as the use of a gamma counter or a scintillation counter or by autoradiography. Isotopes which are particularly useful for the purpose of the present invention are $^3$H, $^{32}$P, $^{125}$I, $^{131}$I, $^{35}$S, and $^{14}$C.

The label may also be a fluorophore. When the fluorescently labeled reagent is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

Alternatively, fluorescence-emitting metals such as $^{125}$Eu, or others of the lanthanide series, may be incorporated into a diagnostic reagent using such metal chelating groups as diethylenetriaminepentaacetic acid (DTPA) of ethylenediamine-tetraacetic acid (EDTA).

The label may also be a chemiluminescent compound. The presence of the chemiluminescently labeled reagent is then determined by detecting the presence of luminescence that arises during the course of a chemical reaction. Examples of particularly useful chemiluminescent labeling compounds are luminol, isolumino, theromatic acridinium ester, imidazole, acridinium salt and oxalate ester.

Likewise, a bioluminescent compound may be used for labeling. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Enzyme labels, such as horseradish peroxidase and alkaline phosphatase, can also be used. When an enzyme label is used, the signal producing system must also include a substrate for the enzyme. If the enzymatic reaction product is not itself detectable, the SPS will include one or more additional reactants so that a detectable product appears.

Conjugation Methods

A label may be conjugated, directly or indirectly (e.g., through a labeled anti-analyte binding reagent antibody), covalently (e.g., with N-succinimidyl 3-(2-pyridyldithzo) propionate (SPDP)) or non-covalently, to the analyte binding reagent, to produce a diagnostic reagent.

Similarly, the analyte binding reagent may be conjugated to a solid phase support to form a solid phase ("capture") diagnostic reagent.

Suitable supports include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention.

The support material may have virtually any possible structural configuration so long as the coupled molecule is capable of binding to its target. Thus the support configuration may be spherical, as in a bead, or cylindrical, as in the inside surface of a test tube, or the external surface of a rod. Alternatively, the surface may be flat such as a sheet, test strip, etc.

Binding Assay Formats

Binding assays may be divided into two basic types, heterogeneous and homogeneous. In heterogeneous assays, the interaction between the affinity molecule and the analyte does not affect the label, hence, to determine the amount or presence of analyte, bound label must be separated from free label. In homogeneous assays, the interaction does affect the activity of the label, and therefore analyte levels can be deduced without the need for a separation step.

In one embodiment, the analyte binding reagent is insolubilized by coupling it to a macromolecular support, and analyte in the sample is allowed to compete with a known quantity of a labeled or specifically labelable analyte analogue. The "analyte analogue" is a molecule capable of competing with analyte for binding to the analyte binding reagent, and the term is intended to include analyte itself. It may be labeled already, or it may be labeled subsequently by specifically binding the label to a moiety differentiating the analyte analogue from analyte. The solid and liquid phases are separated, and the labeled analyte analogue in one phase is quantified. The higher the level of analyte analogue in the solid phase, i.e., sticking to the analyte binding reagent, the lower the level of analyte in the sample.

In a "sandwich assay", both an insolubilized analyte binding reagent, and a labeled analyte binding reagent are employed. The analyte is captured by the insolubilized analyte binding reagent and is tagged by the labeled analyte binding reagent, forming a ternary complex. The reagents may be added to the sample in either order, or simultaneously. The analyte binding reagents may be the same or different. The amount of labeled analyte binding reagent in the ternary complex is directly proportional to the amount of analyte in the sample.

The two embodiments described above are both heterogeneous assays. However, homogeneous assays are conceivable. The key is that the label be affected by whether or not the complex is formed.

Detection of Protein Products of Genes of Interest

Techniques for detecting a protein translation product of interest include, but are not limited to, immunoblotting or Western blotting, ELISA, sandwich assays, fluorescence, or biotin or enzymatic labeling with or without secondary antibodies.

Western blot analysis can be done on the tissue biopsies or tissue aspirates. This would involve resolving the proteins on an electrophoretic gel, such as an SDS PAGE gel, and transferring the resolved proteins onto a nitrocellulose or other suitable membrane. The proteins are incubated with a target binding molecule, such as an antibody.

This binding reagent may be labeled or not. If it is unlabeled, then one would also employ a secondary, labeled molecule which binds to the binding reagent. One approach involves avidinating one molecule and biotinylating the other. Another is for the secondary molecule to be a secondary antibody which binds the original binding reagent.

To improve detection of the specific protein, immunoprecipitation can be conducted. This typically will involve addition of a monoclonal antibody against the protein of interest to samples, then allowing the Ig-protein complex to precipitate after the addition of an affinity bead (ie antihuman Ig Sepharose bead). The immunoprecipitates will undergo several washings prior to transfer onto a nitrocellulose membrane. The Western blot analysis can be performed using another antibody against the primary antibody used.

There are a number of different methods of delivering the radiolabeled analyte binding reagent to the end-user in an amount sufficient to permit subsequent dynamic and/or static imaging using suitable radiodetecting devices. It may be administered by any means that enables the active agent to reach the agent's site of action in the body of a mammal. Because proteins and nucleic acids are subject to being digested when administered orally, parenteral administration, i.e., intravenous, subcutaneous, orintramuscular, would ordinarily be used to optimize absorption of an analyte binding reagent, such as an antibody, which is a protein.

The dosage is the smallest amount capable of providing a diagnostically effective image, and may be determined by means conventional in the art, using known radioimaging agents as a guide.

Typically, the imaging is carried out on the whole body of the subject, or on that portion of the body or organ relevant to the condition or disease under study. The amount of radiolabeled analyte binding reagent accumulated at a given point in time in relevant target organs can then be quantified.

A particularly suitable radiodetecting device is a scintillation camera, such as a gamma camera. A scintillation camera is a stationary device that can be used to image distribution of radiolabeled analyte binding reagent. The detection device in the camera senses the radioactive decay, the distribution of which can be recorded. Data produced by the imaging system can be digitized. The digitized information can be analyzed over time discontinuously or continuously. The digitized data can be processed to produce images, called frames, of the pattern of uptake of the radiolabeled analyte binding reagent in the target tissue/organ at a discrete point in time. In most continuous (dynamic) studies, quantitative data is obtained by observing changes in distributions of radioactive decay in the target tissue/organ over time. In other words, a time-activity analysis of the data will illustrate uptake through clearance of the radiolabeled binding protein by the target organs with time.

Various factors should be taken into consideration in selecting an appropriate radioisotope. The radioisotope must be selected with a view to obtaining good quality resolution upon imaging, should be safe for diagnostic use in humans and animals (except for animal models which will be sacrificed thereafter and will be maintained anaesthetized until then), and should preferably have a short physical half-life so as to decrease the amount of radiation received by the body (with the same exceptions). The radioisotope used should preferably be pharmacologically inert, and, in the quantities administered, should not have any substantial physiological effect.

The analyte binding reagent may be radiolabeled with different isotopes of iodine, for example $^{123}I$, $^{125}I$, or $^{131}I$ (see for example, U.S. Pat. No. 4,609,725). The extent of radiolabeling must, however be monitored, since it will affect the calculations made based on the imaging results (i.e., a diiodinated analyte binding reagent will result in twice the radiation count of a similar monoiodinated analyte binding reagent over the same time frame).

In applications to human subjects, it may be desirable to use radioisotopes other than $^{125}I$ for labeling in order to decrease the total dosimetry exposure of the human body and to optimize the detectability of the labeled molecule (though this radioisotope can be used if circumstances require). Ready availability for clinical use is also a factor. Accordingly, for human applications, preferred radiolabels are for example, $^{99m}Tc$, $^{67}Ga$, $^{66}Ga$, $^{90}Y$, $^{111}In$, $^{113m}In$, $^{123}I$, $^{186}Re$, $^{188}Re$ or $^{211}At$.

The radiolabeled analyte binding reagent may be prepared by various methods. These include radiohalogenation by the chloramine-T method or the lactoperoxidase method and subsequent purification by HPLC (high pressure liquid chromatography), for example as described by Gutkowska et al (1987). Other known method of radiolabeling can be used, such as IODOBEADS™.

For animal models, such as mice or rats, the animal may be sacrificed after administration of the analyte binding reagent and regions which have been subjected to neurotoxic stress imaged on immobilized brain slices.

Diagnostic kits are also within the scope of this invention. Such kits include monoclonal or polyclonal antibodies that can rapidly detect tissue hypoxia.

VIII. General Screening Methods

Each of the genes identified by means of the present invention can be used as a candidate gene in a screening assay for identifying and isolating inhibitors of hypoxia or other neurotoxic stress. Many types of screening assays are known to those of ordinary skill in the art. The specific assay which is chosen will depend to a great extent on the activity of the candidate gene or the protein expressed thereby. Thus, if it is known that the expression product of a candidate gene has enzymatic activity, then an assay which is based on inhibition of the enzymatic activity may be used. If the candidate protein is known to bind to a ligand or other interactor, then the assay can be based on the inhibition of such binding or interaction. When the candidate gene is a known gene, then many of its properties will also be known, and these can be used to determine the best screening assay. If the candidate gene is novel, then some analysis and/or experimentation will be appropriate in order to determine the best assay to be used to find inhibitors of the activity of that candidate gene. The analysis may involve a sequence analysis to find domains in the sequence which would shed light on its activity. Other experimentation described herein to identify the candidate gene and its activity, which experiment would not amount to undue experimentation, may also be engaged in so as to identify the type of screen that would be appropriate to find inhibitors or enhancers, as the case may be, for the candidate gene or the protein encoded thereby.

As is well known in the art, the screening assays may be in vivo or in vitro. An in vivo assay is a cell-based assay using any eukaryotic cell. One such cell-based system is particularly relevant in order to directly measure the activity of candidate genes which are pro-apoptotic functional genes, i.e., expression of the gene will cause apoptosis or otherwise cause cell death in target cells. One way of running such an in vivo assay uses tetracycline-inducible (Tet-inducible) gene expression. Tet-inducible gene expression is well known in the art (Hofmann et al, 1996). Tet-inducible retroviruses have been designed incorporating the Self-inactivating (SIN) feature of a 3' LTRenhancer/promoter retroviral deletion mutant. Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population.

When dealing with pro-apoptotic function candidate genes, Tet-inducible expression causes apoptosis in target cells. One can screen for small molecules or peptides able to rescue the cells from the gene-triggered apoptosis.

If the gene product of the candidate gene phosphorylates with a specific target protein, a specific reporter gene construct can be designed such that phosphorylation of this reporter gene product causes its activation, which can be followed by a color reaction. The candidate gene can be specifically induced, using the Tet-inducible system discussed above, and a comparison of induced vs. non-induced genes provides a measure of reporter gene activation.

In a similar indirect assay, a reporter system can be designed that responds to changes in protein-protein interaction of the candidate protein. If the reporter responds to actual interaction with the candidate protein, a color reaction will occur.

One can also measure inhibition or stimulation of reporter gene activity by modulation of its expression levels via the specific candidate promoter or other regulatory elements. A specific promoter or regulatory element controlling the activity of a candidate gene is defined by methods well known in the art. A reporter gene is constructed which is controlled by the specific candidate gene promoter or regulatory elements. The DNA containing the specific promoter or regulatory agent is actually linked to the gene encoding the reporter. Reporter activity depends on specific activation of the promoter or regulatory element. Thus, inhibition or stimulation of the reporter will be a direct assay of stimulation/inhibition of the reporter gene.

Various in vitro screening assays are also well within the skill of those of ordinary skill in the art. For example, if enzymatic activity is to be measured, such as if the candidate protein has a kinase activity, the target protein can be defined and specific phosphorylation of the target can be followed. The assay may involve either inhibition of target phosphorylation or stimulation of target phosphorylation, both types of assay being well known in the art.

One can also measure in vitro interaction of a candidate protein with interactors. In this screen, the candidate protein is immobilized on beads. An interactor, such as a receptor ligand, is radioactively labeled and added. When it binds to the candidate protein on the bead, the amount of radioactivity carried on the beads (due to interaction with the candidate protein) can be measured. The assay would indicate inhibition of the interaction by measuring the amount of radioactivity on the bead.

Any of the screening assays, according to the present invention, will include a step of identifying the small molecule or peptide which tests positive in the assay and may also include the further step of producing that which has been so identified. The use of any such molecules identified for inhibiting hypoxia or other neurotoxic stress is also considered to be part of the present invention.

Specific screening methods suitable for use with the currently most preferred embodiment, gene comprising SEQ ID NO: 94 can be found at the end of Section X below.

IX. Therapeutic Methods Relating to Good Genes

In accordance with these findings, the present invention extends to the treatment of stroke by the administration of a stroke-ameliorating or stroke-inhibiting amount of an agent capable of at least partially preventing brain damage, or averting the occurrence or reducing the size and severity of an ischemic infarct due, for example, to stroke, aneurysm, cerebrovascular accident, apoplexy or other trauma.

The present invention therefore extends to methods for the treatment of stroke and to corresponding pharmaceutical compositions, comprising and including without limitation as active ingredients a protein encoded by a good gene, such as a protein encoded by a polynucelotide of the sequence of any one of SEQ ID NOs: 2, 3, 7–57, 61–63, 78–84 and 93–85, preferably SEQ ID NOs: 49, 50, 51, 65, 67, 85 and 87, as well as analogs, active fragments, functional derivatives or salts thereof.

Within minutes after cessation of local cerebral blood flow, a region of densely ischemic brain tissue becomes infarcted and dies. This infarcted core is surrounded however, by a zone of ischemic but potentially viable tissue termed the "ischemic penumbra," which receives suboptimal perfusion via collateral blood vessels. The volume of the penumbra that ultimately becomes infarcted after an acute arterial occlusion is determined by a variety of factors that mediate neurotoxicity within this zone during the hours following interrupted blood flow. The nature of these factors (including glutamate, superoxide radicals, and nitric oxide) is only partially understood, as are the complex interactions that will determine whether ischemic tissue will die or recover. Some of these factors are intrinsic to the locus of ischemia, and others are delivered to the penumbra via the circulation. The net result of signaling interactions between these factors can greatly enhance neuronal cytotoxicity in the ischemic penumbra, causing a significantly larger volume of brain damage and necrosis, with corresponding increases in functional damage. The good genes, in accordance with the present invention, participate in mediating increased volumes of cerebral infarction during focal cerebral ischemia.

Good genes may also be used as the target of screening processes to find agents capable of enhancing the expression of a good gene. Thus, the amount of mRNA produced by a cell, before and after subjecting the cell to a neurotoxic stress and administering a test agent, will determine whether that test agent causes further enhancement of expression of that good gene, as compared to a control in which no test agent is added. Such testing can reveal agents which are useful in the treatment of stroke. Screening methods are discussed in Section VIII, hereinabove.

X. Therapeutic Methods Relating to Bad Genes

The ability of an agent to inhibit expression of bad genes provides an additional therapeutic mechanism in the treatment of stroke since it would be expected to result in a reduction in the size and severity of the infarction. An example of a sequence which is part of a bad gene includes SEQ ID NOs: 1, 4–6, 68–71, 74–77 and 82, and most preferably 94, also identified as KIAA 0538, which is a currently most preferred embodiment according to the present invention, as exemplified in detail herein.

The present invention thus includes a method of screening for an agent capable of providing a neuroprotective effect and thus reducing the size and severity of infarct size in stroke, which method comprises administering a test agent concurrent with, or subsequent to, an infarct-producing amount of a product of a bad gene and measuring the resultant decrease in infarct size vis-a-vis a control dose of the infarct-producing amount of the polyamine. Such testing can reveal agents which are useful in the treatment of this aspect of stroke. General screening methods are discussed in Section VIII, hereinabove Specific screening methods suitable for use with the currently most preferred embodiment SEQ ID NO: 94 (which is a fragment of KIAA 0538) will now be presented in detail. The invention provides a method (also referred to herein as a "screening assay"for identifying modulators, i.e., candidate or test compounds or agents (including but not limited to peptides, peptido-mimetics, small molecules or other drugs) which bind to KIAA0538 or have an inhibitory effect on KIAA0538 expression or an inhibitory effect on KIAA0538 activity.

It is known that KIAA0538 is a member of the Ras GTPase-activating-protein family of proteins, recently shown to be a calcium ion dependent Ras-GAP, also known as $Ca^{2+}$ promoted Ras inactivator or "CAPRI" (Lockyer et al, 2001). The members of this family of Ras-GAP proteins have distinct phosphoinositide binding specificities (Minagawa et al., 2001). CAPRI, however, though possessing a recognizable PH domain involved in phosphoinositide binding, has several changes in critical for phosphoinositide binding amino acid position, thus rendering a protein that was shown to be insensitive to phosphoinositide stimulation/ interaction. Alternatively, its activation and translocation to the plasma membrane from the cytosol pool was demonstrated to be regulated by increased concentration of intracellular calcium. Whenever used in this invention KIAA0538 or "CAPRI" is defined as: any member of the KIAA0538 gene family, either full-length, mutant, splice variant, as a chimera with other proteins, or a polypeptide or biologically active fragment or domain of KIAA0538, or of any member of the KIAA0538 gene family, having similar biological activity. KIAA0538 or KIAA0538 gene family member may be present in different forms, including: soluble protein; membrane-bound; bead-bound; or any other form of presenting KIAA0538 protein or fragments and polypeptides derived therefrom.

As used herein, a "target molecule" is a molecule with which KIAA0538 or a KIAA0538 gene family member binds or interacts in nature; for example, an ion, a molecule associated with the cell membrane or a cytoplasmic molecule. As an example, a target molecule may also be a component of a signal transduction pathway which facilitates transduction of an extracellular signal (e.g. a signal generated by binding of a compound to membrane-bound receptor) through the cell membrane and into the cell. The target, for example, can be a second intercellular protein that mediates downstream signaling from KIAA0538. One such known example is the small GTP-binding protein p21Ras. Several signaling pathways have been identified downstream to p21Ras (Kolch (2000) Biochem. J. 351:289), the best understood being that which culminates in Elk and SAP transcription factor activation, further leading to specific gene transcription. This pathway is known to involve the sequential activation of the MAP kinases Raf, Mek and Erk.

As used herein, "cell stimulation" may be induced by many different stimuli that activate intracellular signaling processes, including (but not excluding): G-coupled receptor activation; activation of ion channels; receptor tyrosine kinase activation; etc. As an example, "cell stimulation" relates to any extracellular or intracellular agent, be it exogenous or endogenous that acts to increase intracellular free calcium ion ($[Ca^{2+}]_i$) concentration.

In one embodiment, the invention provides assays for screening candidates or test compounds that bind to, modulate the activity of, influence the subcellular localization of, or affect the expression level of KIAA0538. The test compounds of the present invention can be obtained using any of the numerous approaches in combinatorial and non-combinatorial library methods known in the art, including: Biological libraries (proteins, peptides, etc.); spatially addressable parallel solid phase or solution phase libraries; synthetic library methods; and natural product libraries.

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412–421), or on beads (Lam (1991) Nature 354:82–84), chips (Fodor (1993) Nature 364:555–556), bacteria (Ladner U.S. Pat. No. 5,223, 409), spores (Ladner USP '409), plasmids (Cull et al. (1992) Proc Natl Acad Sci USA 89:1865–1869) or on phage (Scott and Smith (1990) Science 249:386–390); (Devlin (1990) Science 249:404–406); (Cwirla et al. (1990) Proc. Natl. Acad. Sci. 87:6378–6382); (Felici (1991) J. Mol. Biol. 222:301–310).

In one embodiment, an assay is a cell-based assay in which a cell (e.g., of mammalian origin, preferably a neuronal cell) that expresses KIAA0538 is contacted with a test compound and the ability of the test compound to modulate the sub-cellular localization of KIAA0538 is determined. Determining the ability of the test compound to modulate the sub-cellular localization of KIAA0538 can be accomplished, for example by determining its effect on the stimulation-induced translocation of KIAA0538 to the plasma membrane following cell stimulation. This translocation is monitored, for example, by expressing a green fluorescent protein (GFP)-KIAA0538 fusion protein and determining its subcellular localization by fluorescence microscopy. Alternatively, the translocation of KIAA0538 to the plasma membrane may be monitored in cells expressing wild-type KIAA0538 by subcellular fractionation to separate the plasma membrane fraction. The amount of KIAA0538 that is associated with the plasma membrane fraction is then determined by resolving individual plasma membrane proteins using SDS-polyacrylamide gel electrophoresis (SDS-PAGE), followed by protein transfer to an appropriate membrane (e.g., PVDF) and analysis of transferred proteins by Western blot analysis using KIAA0538—specific antibodies.

In another embodiment, an assay is a cell-based assay in which a cell (e.g., of mammalian origin, preferably a neuronal cell) that expresses KIAA0538 is contacted with a test compound and the ability of the test compound to modulate the association of CAPRI with its downstream effectors and/or its target molecule(s) is determined. One example for an identified target molecule of KIAA0538 is p21Ras. Determining the ability of the test compound to modulate the association between KIAA0538 and p21Ras following cell stimulation can be accomplished, for example by specifically precipitating KIAA0538 from whole cell lysates and determining the amount of co-precipitated p21Ras. Such co-precipitation and specific immunoblotting techniques are well known in the art.

In a preferred embodiment of the invention an assay is a cell-based assay in which a cell that expresses KIAA0538, e.g. a mammalian cell, preferably a neuronal cell is contacted with a test compound and the ability of the test compound to modulate (i.e., stimulate or inhibit) the activity of KIAA0538 is determined. Determining the ability of the test compound to modulate the activity of CAPRI can be accomplished, preferably, by monitoring its effect on p21Ras-mediated GTP hydrolysis. Since KIAA0538 acts as a GTPase activating protein (GAP) for p21Ras, it is expected that CAPRI activation will result in increased GTP hydrolysis by p21Ras. This will result in a decrease in the amount of p21Ras-bound GTP. The p21Ras binding domain (RBD) in the signaling protein Raf has been identified and previously used for specifically precipitating the GTP-bound form of p21Ras. This assay can therefore be employed for determining the state of KIAA0538 activation. As an example, a typical assay is comprised of stimulating a KIAA0538-expressing cell in the presence of a test compound and determining the effect of the latter on the amount of p21Ras-associated GTP by lysing the cells in an Ad appropriate lysis buffer and using RBD (as its fusion with glutathione S-transferase) to extract GTP-bound p21Ras.

These extracts are then subjected to SDS-PAGE, followed by protein transfer to appropriate membranes (e.g., PVDF) and analysis of transferred proteins by Western blot analysis using p21Ras-specific antibodies. The intensity of the p21Ras-specific signal should correlate with the cellular level of GTP-bound p21Ras, which in turn is indicative of the level of CAPRI activation.

In another preferred embodiment, determining the ability of the test compound to modulate the activity of CAPRI can be accomplished, for example, by determining the effect of a test compound on a known downstream signaling activity of KIAA0538. For example, the ability of a test compound to modulate the activity of KIAA0538 is determined by following the phosphorylation of cellular proteins downstream to KIAA0538 by, for example, immunoblot analysis using phosphorylation state-specific antibodies. As a specific example, the activation of KIAA0538 should lead to p21Ras inactivation, further leading to dephosphorylation of the kinases Erk1/2 which are known targets downstream to p21Ras activation. Additionally, KIAA0538 activity can be determined by any of the following techniques/approaches: Detecting induction of a cellular second messenger; detecting changes in the catalytic/enzymatic activity of the target molecule using an appropriate endogenous or exogenous substrate; detecting the induction of a reporter gene (for example, comprising a Elk/SAP-responsive regulatory element operatively linked to a nucleic acid encoding a detectable marker, e.g. luciferase); or detecting a cellular response, for example, cell survival, cellular differentiation, cell proliferation, etc., In yet another embodiment, an assay of the present invention is a cell-free assay comprising contacting recombinant KIAA0538 with a test compound and determining the ability of the test compound to bind to CAPRI. Binding of the test compound to KIAA0538 can be determined either directly or indirectly by labeling the test compound with a radioisotope, reacting the test compound with KIAA0538 and determining the amount of labeled compound in complex with KIAA0538. For example, test compounds can be labeled with $^{125}$I, $^{35}$S, $^{14}$C, or $^{3}$H, either directly or indirectly, allowing the test compound to be detected by direct counting of radio-emission or by scintillation counting. In a preferred embodiment, the assay comprises contacting KIAA0538 with a known compound which binds KIAA0538 (e.g., p21Ras or $Ca^{2+}$) to form an assay mixture, contacting the assay mixture with a test compound, and determining the ability of the test compound to interact with KIAA0538, wherein determining the ability of the test compound to interact with KIAA0538 comprises determining the ability of the test compound to preferentially bind to CAPRI as compared to the known compound. This can be accomplished, for example, by radio-labeling the compound known to bind to KIAA0538 and monitoring its displacement from its complex with KIAA0538 as a result of the interaction with the unlabeled test compound.

In another embodiment, an assay is a cell-free assay comprising contacting KIAA0538 with a test compound and determining the ability of the test compound to modulate (e.g. stimulate or inhibit) the activity of KIAA0538. Determining the ability of the test compound to modulate the activity of CAPRI can be accomplished, for example, by determining the ability of the test compound to block the GTPase activity of the complex of XIAA0538 with p21Ras. This assay can be set up by incubating together recombinant KIAA0538, recombinant p21Ras and gamma-$^{32}$p-labeled GTP and following the amount of residual radioactive label in GTP by any of the several techniques known in the art.

The cell-free assays of the present invention are compatible with the use of both, the soluble form or the membrane-bound form of KIAA0538. In more than one embodiment of the above assay methods of the present invention, it may be desirable to immobilize either KIAA0538 or its target molecule to facilitate separation of complexed from uncomplexed forms of one or both of the proteins, as well as to accommodate automation of the assay. Binding of a test compound to KIAA0538, or interaction of KIAA0538 with its target molecule in the presence and/or absence of a candidate test compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to bind to a matrix. For example, glutathione-S-transferase/KIAA0538 fusion proteins or glutathione-S-transferase/target fusion proteins can be adsorbed onto glutathione sepharose beads or glutathione derivatized microtitre plates, which are then combined with the test compound and either the non-adsorbed target protein or KIAA0538 (appropriately), and the mixture incubated under conditions suitable for complex formation. Following incubation, the beads or microtitre plate wells are washed to remove any unbound components, the matrix immobilized in the case of beads and the amount of formed complex is determined either directly or indirectly, for example, as described above. Alternatively, the complexes can be dissociated from the matrix, and the level of CAPRI binding or activity determined using standard techniques.

Other techniques for immobilizing proteins on matrices can also be used in the screening assays of the invention. For example, either KIAA0538 or its target molecule can be immobilized utilizing conjugation of biotin and streptavidin. Biotinylated KIAA0538 or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with CAPRI or its target molecules but which do not interfere with binding of CAPRI to its target molecule can be bound to the wells of the plate, and free target or KIAA0538 trapped in the wells by antibody conjugation. Methods for detecting such complexes, in addition to those described above for the GST-immobilized complexes, include immunodetection of complexes using antibodies reactive with CAPRI or target molecule, as well as enzyme-linked assays which rely on detecting an enzymatic activity of KIAA0538 or that associated with CAPRI or its target molecule.

In another embodiment, modulators of CAPRI expression are identified in a method wherein a cell is contacted with a candidate compound and the expression of KIAA0538 mRNA or protein in the cell is determined. The level of expression of KIAA0538 mRNA or protein in the presence of the candidate compound is compared to the level of expression of KIAA0538 mRNA or protein in the absence of the candidate compound. The candidate compound can then be identified as a modulator of KIAA0538 expression based on this comparison. For example, when expression of KIAA0538 mRNA or protein is greater in the presence of the candidate compound than in its absence, the candidate compound is identified as a stimulator of KIAA0538 mRNA or protein expression. Alternatively, when expression of KIAA0538 mRNA or protein is less in the presence of the candidate compound than in its absence, the candidate compound is identified as an inhibitor of KIAA0538 mRNA or protein expression. The level of KIAA0538 mRNA or protein expression in the cells can be determined by methods described herein for detecting KIAA0538 mRNA or protein.

In yet another aspect of the invention, KIAA0538 protein can be used as "bait protein" in a two-hybrid or three hybrid assay (see, e.g., U.S. Pat. No. 5,283,317; Zervos et al. (1993) Cell 72:223–232; Madura el al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins which bind to or interact with KIAA0538 (target molecules) and modulate KIAA0538 activity. Such KIAA0538-binding proteins are also likely to be involved in the propagation of signals by KIAA0538 as, for example, upstream or downstream elements of the KIAA0538 signaling pathway.

The two-hybrid system is based on the modular nature of most transcription factors, which consist of separable DNA-binding and activation domains. Briefly, the assay utilizes two different DNA constructs. In one construct, the gene that codes for KIAA0538 is fused to a gene encoding the DNA binding domain of a known transcription factor (e.g., GAL-4). In the other construct, a DNA sequence, from a library of DNA sequences, that encodes an unidentified protein "prey" or "sample"is fused to a gene that codes for the activation domain of the known transcription factor. If the "bait" and the "prey" proteins are able to interact, in vivo, forming a KIAA0538-dependent complex, the DNA-binding and activation domains of the transcription factor are brought into close proximity. This proximity allows transcription of a reporter gene (e.g., LacZ) which is linked to a transcriptional regulatory site responsive to the transcription factor. Expression of the reporter gene can be detected and cell colonies containing the functional transcription factor can be isolated and used to obtain the cloned gene that encodes the protein which interacts with KIAA0538.

This invention further pertains to novel agents identified by the above-described screening assays and uses thereof for treatments as described herein.

The production and administration of antisense sequences and ribozymes that specifically bind and cleave a particular mRNA sequence are discussed in Sections XII and XIII hereinafter. Such ribozymes and antisense sequences relating specifically to bad genes and the mRNA they describe will inhibit the expression of these bad genes and, thus, will provide an additional therapeutic mechanism in treating the effects of stroke, hypoxia and/or ischemia.

XI. Antibodies

The present invention also comprehends antibodies specific for the proteins encoded by a naturally-occurring cDNA which is part of the present invention as discussed above. Such an antibody may be used for diagnostic purposes to identify the presence of any such naturally-occurring proteins. Such antibody may be a polyclonal antibody or a monoclonal antibody or any other molecule that incorporates the antigen-binding portion of a monoclonal antibody specific for such a protein. Such other molecules may be a single-chain antibody, a humanized antibody, an F(ab) fraction, a chimeric antibody, an antibody to which is attached a label, such as fluorescent or radioactive label, or an immunotoxin in which a toxic molecule is bound to the antigen binding portion of the antibody. The examples are intended to be non-limiting. However, as long as such a molecule includes the antigen-binding portion of the antibody, it will be expected to bind to the protein and, thus, can be used for the same diagnostic purposes for which a monoclonal antibody can be used. The antibodies to the novel polypeptides encoded by the novel polynucleotides of this invention are also novel, and are considered an integral aspect of this invention XIX. Antisense Sequences In order to manipulate the expression of a bad gene, it is desirable to produce antisense RNA in a cell. To this end, the complete or partial cDNA of a bad gene in accordance with the present invention is inserted into an expression vector comprising a promoter. The 3' end of the cDNA is thereby inserted adjacent to the 3' end of the promoter, with the 5' end of the cDNA being separated from the 3' end of the promoter by said cDNA . Upon expression of the cDNA in a cell, an antisense RNA is therefore produced which is incapable of coding for the protein. The presence of antisense RNA in the cell reduces the expression of the cellular (genomic) copy of the bad gene.

For the production of antisense RNA, the complete cDNA may be used. Alternatively, a fragment thereof may be used, which is preferably between about 9 and 2,000 nucleotides in length, more preferably between 15 and 500 nucleotides, and most preferably between 30 and 150 nucleotides.

The fragment is preferably corresponding to a region within the 5' half of the cDNA, more preferably the 5' region comprising the 5' untranslated region and/or the first exon region, and most preferably comprising the ATG translation start site. Alternatively, the fragment may correspond to DNA sequence of the 5' untranslated region only.

A synthetic oligonucleotide may be used as antisense oligonucleotide. The oligonucleotide is preferably a DNA oligonucleotide. The length of the antisense oligonucleotide is preferably between 9 and 150, more preferably between 12 and 60, and most preferably between 15 and 50 nucleotides. Suitable antisense oligonucleotides that inhibit the production of the protein of the present invention from its encoding mRNA can be readily determined with only routine experimentation through the use of a series of overlapping oligonucleotides similar to a "gene walking" technique that is well-known in the art. Such a "walking" technique as well-known in the art of antisense development can be done with synthetic oligonucleotides to walk along the entire length of the sequence complementary to the mRNA in segments on the order of 9 to 150 nucleotides in length. This "gene walking" technique will identify the oligonucleotides that are complementary to accessible regions on the target mRNA and exert inhibitory antisense activity.

Alternatively, an oligonucleotide based on the coding sequence of a protein capable of binding to a bad gene or the protein encoded thereby can be designed using Oligo 4.0 (National Biosciences, Inc.). Antisense molecules may also be designed to inhibit translation of an mRNA into a polypeptide by preparing an antisense which will bind in the region spanning approximately −10 to +10 nucleotides at the 5' end of the coding sequence.

The mechanism of action of antisense RNA and the current state of the art on use of antisense tools is reviewed in Kumar et al (1998). The use of antisense oligonucleotides in inhibition of BMP receptor synthesis has been described by Yeh et al (1998). The use of antisense oligonucleotides for inhibiting the synthesis of the voltage-dependent potassium channel gene Kv1.4 has been described by Meiri et al (1998). The use of antisense oligonucleotides for inhibition of the synthesis of Bcl-x has been described by Kondo et al (1998). The therapeutic use of antisense drugs is discussed by Stix (1998); Flanagan (1998); Guinot et al (1998), and references therein.

Modifications of oligonucleotides that enhance desired properties are generally used when designing antisense oligonucleotides. For instance, phosphorothioate bonds are used instead of the phosphoester bonds that naturally occur in DNA, mainly because such phosphorothioate oligonucleotides are less prone to degradation by cellular enzymes. Peng Ho et al teach that undesired in vivo side effects of phosphorothioate oligonucleotides may be reduced when using a mixed phosphodiester-phosphorothioate backbone. Preferably, 2'-methoxyribonucleotide modifications in 60% of the oligonucleotide is used. Such modified oligonucleotides are capable of eliciting an antisense effect comparable to the effect observed with phosphorothioate oligonucleotides. Peng Ho et al teach further that oligonucleotide analogs incapable of supporting ribonuclease H activity are inactive.

Therefore, the preferred antisense oligonucleotide of the present invention has a mixed phosphodiester-phosphorothioate backbone. Preferably, 2'-methoxyribonucleotide modifications in about 30% to 80%, more preferably about 60%, of the oligonucleotide are used.

In the practice of the invention, antisense oligonucleotides or antisense RNA may be used. The length of the antisense RNA is preferably from about 9 to about 3,000 nucleotides, more preferably from about 20 to about 1,000 nucleotides, most preferably from about 50 to about 500 nucleotides.

In order to be effective, the antisense oligonucleotides of the present invention must travel across cell membranes. In general, antisense oligonucleotides have the ability to cross cell membranes, apparently by uptake via specific receptors. As the antisense oligonucleotides are single-stranded molecules, they are to a degree hydrophobic, which enhances passive diffusion through membranes. Modifications may be introduced to an antisense oligonucleotide to improve its ability to cross membranes. For instance, the oligonucleotide molecule may be linked to a group which includes partially unsaturated aliphatic hydrocarbon chain and one or more polar or charged groups such as carboxylic acid groups, ester groups, and alcohol groups. Alternatively, oligonucleotides may be linked to peptide structures, which are preferably membranotropic peptides. Such modified oligonucleotides penetrate membranes more easily, which is critical for their function and may, therefore, significantly enhance their activity. Palmityl-linked oligonucleotides have been described by Gerster et al (1998). Geraniol-linked oligonucleotides have been described by Shoji et al (1998). Oligonucleotides linked to peptides, e.g., membranotropic peptides, and their preparation have been described by Soukchareun et al (1998). Modifications of antisense molecules or other drugs that target the molecule to certain cells and enhance uptake of the oligonucleotide by said cells are described by Wang (1998).

The antisense oligonucleotides of the invention are generally provided in the form of pharmaceutical compositions. These compositions are for use by injection, topical administration, or oral uptake.

Preferred uses of the pharmaceutical compositions of the invention by injection are subcutaneous injection, intravenous injection, and intramuscular injection. Less convenient routes of administration may include intraperitoneal, intradural, intra-thecal administration or intra-arterial administration when required.

The pharmaceutical composition of the invention generally comprises a buffering agent, an agent which adjusts the osmolarity thereof, and optionally, one or more carriers, excipients and/or additives as known in the art, e.g., for the purposes of adding flavors, colors, lubrication, or the like to the pharmaceutical composition.

Carriers may include starch and derivatives thereof, cellulose and derivatives thereof, e.g., microcrystalline cellulose, xanthan gum, and the like. Lubricants may include hydrogenated castor oil and the like.

A preferred buffering agent is phosphate-buffered saline solution (PBS), which solution is also adjusted for osmolarity.

A preferred pharmaceutical formulation is one lacking a carrier. Such formulations are preferably used for administration by injection, including intravenous injection.

The preparation of pharmaceutical compositions is well known in the art and has been described in many articles and textbooks, see e.g., *Remington's Pharmaceutical Sciences*, especially pp 1521–1712 therein.

Additivese may also be selected to enhance uptake of the antisense oligonucleotide across cell membranes. Such agents are generally agents that will enhance cellular uptake of double-stranded DNA molecules. For instance, certain lipid molecules have been developed for this purpose, including the transfection reagents DOTAP (Boehringer Mannheim), Lipofectin, Lipofectam, and Transfectam, which are available commercially. For a comparison of various of these reagents in enhancing antisense oligonucleotide uptake, see e.g., Quattrone et al (1995) and Capaccioli et al (1993). The antisense oligonucleotide of the invention may also be enclosed within liposomes. The preparation and use of liposomes, e.g., using the above-mentioned transfection reagents, is well known in the art. Other methods of obtaining liposomes include the use of Sendai virus or of other viruses. Examples of publications disclosing oligonucleotide transfer into cells using the liposome technique are, e.g., Meyer et al (1998), Kita et al (1999), Nakamura et al (1998), Abe et al (1998), Soni et al (1998), Bai et al (1998), see also discussion in the same Journal p. 819–20, Bochot et al (1998), Noguchi et al (1998), Kanamaru et al (1998), and references therein. The use of Lipofectin in liposome-mediated oligonucleotide uptake is described in Sugawa et al (1998). The use of fusogenic cationic-lipid-reconstituted influenza-virus envelopes (cationic virosomes) is described in Waelti et al (1998).

The above-mentioned cationic or nonionic lipid agents not only serve to enhance uptake of oligonucleotides into cells, but also improve the stability of oligonucleotides that have been taken up by the cell.

XIII. Ribozymes

Given the known mRNA sequence of a gene, ribozymes, which are RNA molecules that specifically bind and cleave said mRNA sequence (see, e.g., Chen et al (1992), Zhao et al (1993), Shore et al (1993), Joseph et al (1993), Shimayama et al (1993), and Cantor et al (1993), may be designed.

Accordingly, a ribozyme-encoding RNA. sequence may be designed that cleaves the mRNA of a bad gene of the present invention. The site of cleavage is preferably located in the coding region or in the 5' nontranslated region, more preferably, in the 5' part of the coding region close to the AUG translational start codon.

A DNA encoding a ribozyme according to the present invention may be introduced into cells by way of DNA uptake, uptake of modified DNA (see modifications for oligonucleotides and proteins that result in enhanced membrane permeability, as described above for oligonucleotides and described below for proteins), or viral vector-mediated gene transfer.

XIV. Introduction of Proteins, Peptides, and DNA into Cells

The present invention provides proteins encoded by good genes, peptides derived therefrom, antisense DNA molecules corresponding to bad genes, and oligonucleotides. A therapeutic or research-associated use of these tools necessitates their introduction into cells of a living organism or into cultured cells. For this purpose, it is desired to improve membrane permeability of peptides, proteins and oligonucleotides. Ways to improve membrane permeability of oligonucleotides have been discussed above. The same principle, namely, derivatization with lipophilic structures, may also be used in creating peptides and proteins with enhanced membrane permeability. For instance, the sequence of a known membranotropic peptide as noted above may be added to the sequence of the peptide or protein. Further, the peptide or protein may be derivatized by partly lipophilic structures such as the above-noted hydrocarbon chains, which are substituted with at least one polar or charged group. For example, lauroyl derivatives of peptides have been described by Muranishi et al (1991). Further modifications of peptides s and proteins include the oxidation of methionine residues to thereby create sulfoxide groups, as described by Zacharia et al (1991). Zacharia and coworkers also described peptide or derivatives wherein the relatively hydrophobic peptide bond is replaced by its ketomethylene isoester ($COCH_2$). It is known to those of skill in the art of protein and peptide chemistry these and other modifications enhance membrane permeability.

Another way of enhancing membrane permeability is to make use of receptors, such as virus receptors, on cell surfaces in order to induce cellular uptake of the peptide or protein. This mechanism is used frequently by viruses, which bind specifically to certain cell surface molecules. Upon binding, the cell takes the virus up into its interior. The cell surface molecule is called a virus receptor. For instance, the integrin molecules CAR and AdV have been described as virus receptors for Adenovirus (Hemmi et al, 1998, and references cited therein). The CD4, GPR1, GPR15, and STRL33 molecules have been identified as receptors/coreceptors for HIV (Edinger et al, 1998 and references cited therein).

By conjugating peptides, proteins or oligonucleotides to molecules that are known to bind to cell surface receptors, the membrane permeability of said peptides, proteins or oligonucleotides will be enhanced. Examples of suitable groups for forming conjugates are sugars, vitamins, hormones, cytokines, transferrin, asialoglycoprotein, and the like molecules. Low et al U.S. Pat. No. 5,108,921 describes the use of these molecules for the purpose of enhancing membrane permeability of peptides, proteins and oligonucleotides, and the preparation of said conjugates.

Low and coworkers further teach that molecules such as folate or biotin may be used to target the conjugate to a multitude of cells in an organism, because of the abundant and nonspecific expression of the receptors for these molecules.

The above use of cell surface proteins for enhancing membrane permeability of a peptide, protein or oligonucleotide of the invention may also be used in targeting the peptide, protein or oligonucleotide of the present invention to certain cell types or tissues. For instance, if it is desired to target neural cells, it is preferable to use a cell surface protein that is expressed more abundantly on the surface of those cells.

The protein, peptide or oligonucleotide of the invention may therefore, using the above-described conjugation techniques, be targeted to a certain cell type. For instance, if it is desired to protect from neurotoxic stress in neural cell, a good gene, or protein encoded thereby or an antisense or ribozyme of the invention designed to inhibit a bad gene, may be targeted at such cells, for instance, by using molecules that are expressed on these cells. The skilled person will recognize the possibilities of using a cell surface marker selected from a multitude of known markers of neural and other cells, and of these, further selecting those that are expressed constitutively or inducibly.

XV. Virus-Mediated Cellular Targeting

The proteins, peptides and antisense sequences of the present invention may be introduced into cells by the use of a viral vector. The use of a vaccinia vector for this purpose is described in Chapter 16 of Ausubel et al (1994–2000). The use of adenovirus vectors has been described, e.g., by Teoh et al (1998), Narumi et al (1998), Pederson et al (1998), Guang-Lin et al (1998), and references therein, Nishida et al (1998), Schwarzenberger et al (1998), and Cao et al (1998). The use of SV-40 derived viral vectors and SV-40 based packaging systems has been described by Fang et al (1997). The use of papovaviruses which specifically target B-lymphocytes, has been described by Langner et al (1998).

When using viruses as vectors, the viral surface proteins are generally used to target the virus. As many viruses, such as the above adenovirus, are rather unspecific in their cellular tropism, it may be desirable to impart further specificity by using a cell-type or tissue-specific promoter. Griscelli et al (1998) teach the use of the ventricle-specific cardiac myosin light chain 2 promoter for heart-specific targeting of a gene whose transfer is mediated by adenovirus.

Alternatively, the viral vector may be engineered to express an additional protein on its surface, or the surface protein of the viral vector may be changed to incorporate a desired peptide sequence. The viral vector may thus be engineered to express one or more additional epitopes which may be used to target said viral vector. For instance, cytokine epitopes, MHC class II-binding peptides, or epitopes derived from homing molecules may be used to target the viral vector in accordance with the teaching of the invention. The above Langer et al. (1998) reference teach the use of heterologous binding motifs to target B-lymphotrophic papoaviruses. For brain delivery, the preferred vectors are HSV-based and lentiviral ones.

XVI. Pharmaceutical Compositions

The pharmaceutical compositions of the invention are prepared generally as known in the art. Thus, pharmaceutical compositions comprising nucleic acids, e.g., ribozymes, antisense RNA or antisense oligonucleotides, are prepared as described above for pharmaceutical compositions comprising oligonucleotides and/or antisense RNA. The above considerations apply generally also to other pharmaceutical compositions. For instance, the pharmaceutical composition of the invention may contain naked DNA, e.g., good genes or fragments or derivatives thereof and a pharmaceutically acceptable carrier as known in the art. A variety of ways to enhance uptake of naked DNA is known in the art. For instance, cationic liposomes (Yotsuyanagi et al, 1998), dicationic amphiphiles (Weissig et al, 1998), fusogenic liposomes (Mizuguchi et al, 1996), mixtures of stearyl-poly (L-lysine) and low density lipoprotein (LDL), (terplex, Kim et al, 1998), and even whole bacteria of an attenuated mutant strain of *Salmonella typhimurium* (Paglia et al, 1998) have been used in the preparation of pharmaceutical compositions containing DNA.

Administration of virus particles has been described in prior art publications, see, e.g., U.S. Pat. No. 5,882,877, where Adenovirus based vectors and administration of the DNA thereof is described. The viral DNA was purified on a CsCl gradient and then dialyzed against Tris-buffered saline to remove CsCl. In these preparations, viral titers (pfu/ml) of $10^{14}$ to $10^{10}$ are preferably used. Administration of virus particles as a solution in buffered saline, to be preferably administered by subcutaneous injection, is known from U.S. Pat. No. 5,846,546. Croyle and coworkers (Croyle et al, 1998) describe a process for the preparation of a pharmaceutical composition of recombinant adenoviral vectors for oral gene delivery, using CsCl gradients and lyophilization in a sucrose-containing buffer.

Where the pharmaceutical composition of the invention includes a peptide or protein according to the present invention, the composition will generally contain salts, preferably in physiological concentration, such as PBS (phosphate-buffered saline), or sodium chloride (0.9% w/v), and a buffering agent, such as phosphate buffer in water or in the well-known PBS buffer. In the following section, the term "peptide" is meant to include all proteins or peptides according to the invention. The preparation of pharmaceutical compositions is well known in the art, see e.g., U.S. Pat. Nos. 5,736,519, 5,733,877, 5,554,378, 5,439,688, 5,418,219, 5,354,900, 5,298,246, 5,164,372, 4,900,549, 4,755,383, 4,639,435, 4,457,917, and 4,064,236.

The peptide of the present invention, or a pharmacologically acceptable salt thereof is preferably mixed with an excipient, carrier, diluent, and optionally, a preservative or the like, pharmacologically acceptable vehicles as known in the art, see, e.g., the above U.S. patents. Examples of excipients include, glucose, mannitol, inositol, sucrose, lactose, fructose, starch, corn starch, microcrystalline cellulose, hydroxypropylcellulose, hydroxypropylmethylcellulose, polyvinylpyrrolidone and the like. Optionally, a thickener may be added, such as a natural gum, a cellulose derivative, an acrylic or vinyl polymer, or the like.

The pharmaceutical composition is provided in solid, liquid or semi-solid form. A solid preparation may be prepared by blending the above components to provide a powdery composition. Alternatively, the pharmaceutical composition is provided as a lyophilized preparation. The liquid preparation is provided preferably as an aqueous solution, aqueous suspension, oil suspension or microcapsule composition. A semi-solid composition is provided preferably as hydrous or oily gel or ointment. About 0.001 to 60 w/v %, preferably about 0.05 to 25 w/v % of peptide is provided in the composition.

A solid composition may be prepared by mixing an excipient with a solution of the peptide of the invention, gradually adding a small quantity of water, and kneading the mixture. After drying, preferably in vacuo, the mixture is pulverized. A liquid composition may be prepared by dissolving, suspending or emulsifying the peptide of the invention in water, a buffer solution or the like. An oil suspension may be prepared by suspending or emulsifying the peptide of the invention or protein in an oleaginous base, such as sesame oil, olive oil, corn oil, soybean oil, cottonseed oil, peanut oil, lanolin, petroleum jelly, paraffin, Isopar, silicone oil, fatty acids of 6 to 30 carbon atoms or the corresponding glycerol or alcohol esters. Buffers include Sorensen buffer (*Ergeb Physiol*, 12:393, 1912), Clark-Lubs buffer (*J Bact*, 2 (1):109, 191, 1917), MacIlvaine buffer (*J Biol Chem*, 49:183, 1921), Michaelis buffer (*Die Wasserstoffinonenkonzentration*, p. 186, 1914), and Kolthoff buffer (*Biochem Z*, 179:410, 1926).

A composition may be prepared as a hydrous gel, e.g., for transnasal administration. A hydrous gel base is dissolved or dispersed in aqueous solution containing a buffer, and the peptide of the invention, and the solution warmed or cooled to give a stable gel.

Preferably, the peptide of the invention is administered through intravenous, intramuscular or subcutaneous administration. Oral administration is expected to be less effective, because the peptide may be digested before being taken up. Of course, this consideration may apply less to a peptide of the invention which is modified, e.g., by being a cyclic peptide, by containing non-naturally occurring amino acids, such as D-amino acids, or other modifications which enhance the resistance of the peptide to biodegradation. Decomposition in the digestive tract may be lessened by use of certain compositions, for instance, by confining the peptide of the invention in microcapsules such as liposomes. The pharmaceutical composition of the invention may also be administered to other mucous membranes. The pharmaceutical composition is then provided in the form of a suppository, nasal spray or sublingual tablet. The dosage of the peptide of the invention may depend upon the condition to be treated, the patient's age, bodyweight, and the route of administration, and will be determined by the attending physician.

The uptake of a peptide of the invention may be facilitated by a number of methods. For instance, a non-toxic derivative of the cholera toxin B subunit, or of the structurally related subunit B of the heal-labile enterotoxin of enterotoxic *Eschericia coli* may be added to the composition, see U.S. Pat. No. 5,554,378.

In another embodiment, the peptide of the invention is provided in a pharmaceutical composition comprising a biodegradable polymer selected from poly-1,4-butylene succinate, poly-2,3-butylene succinate, poly-1,4-butylene fumarate and poly-2,3-butylene succinate, incorporating the peptide of the invention as the pamoate, tannate, stearate or palmitate thereof. Such compositions are described, e.g., in U.S. Pat. No. 5,439,688.

In a further embodiment, a composition of the invention is a fat emulsion. The fat emulsion may be prepared by adding to a fat or oil about 0.1–2.4 w/w of emulsifier such as a phospholipid, an emulsifying aid, a stabilizer, mixing mechanically, aided by heating and/or removing solvents, adding water and isotonic agent, and optionally, adjusting adding the pH agent, isotonic agent. The mixture is then homogenized. Preferably, such fat emulsions contain an electric charge adjusting agent, such as acidic phospholipids, fatty acids, bilic acids, and salts therof. Acidic phospholipids include phosphatidylserine, phosphatidylglycerol, phosphatidylinositol, and phosphatidic acid. Bilic acids include deoxycholic acid, and taurocholic acid. The preparation of such pharmaceutical compositions is described in U.S. Pat. No. 5,733,877.

XVII. Knock-Out or Tranagenic Animals

Tranagenic Nice. The introduction of gene constructs into the genome of mice (transgenic mice) is a well-established procedure. Transgenic mice provide the opportunity to examine the phenotypic outcome of over-expression or ectopic expression of genes (gain-of-function experiments). Specific phenotypes obtained after such expression is a very strong predictor of gene function. Many human genes have been expressed in transgenic mice and in most cases they function appropriately. Thus, for the purpose of examining gain-of-function, human genes can be used. Specific plasmid vector constructs are available. They carry any of a variety of promoters that allow expression of the gene in specific tissues. For example, promoters that are brain specific are available, liver specific promoters, vascular-endothelial cell specific promoters, bone specific promoters, cardiac muscle specific promoters and many more.

Knockout Nice. Loss-of-function experiments in mice are mostly done by the technique of gene knockout. The technology is well established. It requires the use of mouse genes for the purpose of generating knockout of the specific gene in embryonic stem (ES) cells that are then incorporated into the mouse germ-line cells from which mice carrying the gene knockout are generated. From a human gene there are several ways to recover the homologous mouse gene. One way is to use the human gene to probe mouse genomic libraries of lambda phages, cosmids or BACs. Positive clones are examined and sequenced to verify the identity of the mouse gene. Another way is to mine the mouse EST database to find the matching mouse sequences. This can be the basis for generating primer-pairs or specific mouse probes that allow an efficient screen of the mouse genomic libraries mentioned above by PCR or by hybridization. For the vast majority of genes the mouse homologue of the human gene retains the same biological function. The loss-of-function experiments in mice indicate the consequences of absence of expression of the gene on the phenotype of the mouse and the information obtained is applicable to the function of the gene in humans. On many occasions a specific phenotype observed in knockout mice was similar to a specific human inherited disease and the gene was then proved to be involved and mutated in the human disease.

XVIII. Promoters

As promoters and regulatory elements of the candidate genes in accordance with the present invention are also useful in the screening assays described in Section VIII, the present invention is also directed to the sequence of such promoters and/or other regulatory agents. Once the gene has been identified, it is within the routine skill in the art for one ordinary skill to identify the sequence of the promoter region or other regulatory regions. This may be accomplished as discussed below.

It is well recognized that promoters are generally located upstream of the coding sequence. There are numerous methods used conventionally in the art for determining a promoter region and portions of that region essential for promoter activity. For example, Kähäri et al (1990) made constructs in which a region from −2260 to −14 upstream of the ATG initiation codon of the human elastin gene was systematically truncated from −2260 towards −14 to create a set of nested deletions, all with the same −14 end point, which is linked to and controls the expression of a coding sequence for a reporter molecule (chloramphenicol acetyltransferase). The constructs are assayed for the expression of the reporter as a measure of the promoter activity of the truncated DNA fragments. Using this type of deletion analysis, Kähäri et al isolated a 497 bp fragment which provided maximal gene expression.

The above method is directed to locating the promoter region, as well as identifying the portions thereof essential for activity. Other mutagenesis techniques, such as linker scanning, which generate a series of clustered point mutations can also be used to fine map the sequence elements required for promoter function.

Although in a great majority of cases the 5'-flanking region is sufficient to promote gene expression, it has been reported that in some instances intron, or even the 3'-untranslated sequences, provide regulatory sequences that contribute to promoter activity. For example, intron I sequences were found to be important for high-level and tissue-specific expression of an alpha-skeletal actin gene, a beta-globin gene and a peripherin gene (Reecy et al, 1998; James-Pederson et al, 1995; Belecky-Adams et al, 1993). In view of these examples of introns or 3'-untranslated sequences contributing to promoter activity, promoter constructs (i.e., fused to reporter gene) may include intron I sequences of the candidate gene and, when necessary, 3'-untranslated sequences. In the former case, a DNA fragment can be isolated that spans the 5'-flanking region, the first exon and the first intron, followed by the reporter gene. The translation initiation codon of the candidate gene could also be mutated to avoid translation of truncated candidate gene product.

XIX. Examples

The specific sequences found in accordance with the present invention are set forth and discussed in the Examples hereinafter.

A. Chip Design

Two proprietary DNA chips were used in the present experimentation:

Human Apoptosis Chip (HAP-chip): A "functional" human apoptosis DNA microarray, containing 10,000 cDNA clones, was constructed from cDNA clones selected by functional profiling, which potentially identifies cDNA fragments that correspond to genes with pro- or anti-apoptotic activity.

cDNA clones were selected in the following functional screens:

Differentiated neuroblastoma (BE2C cells) subjected to:

dopamine selection glutamate selection hypoxia selection

HeLa cells subjected to apoptotic stimuli:

FAS selection serum starvation taxol irradiation

Thus, the HAP chip contains cDNA clones related to cell death. The microarray contains 5,000 clones.

Rat Stroke Chip: The Stroke cDNA microarray was constructed by combining two types of cDNA libraries (Table 1): (1) a library generated by sequence-dependent gene identification (SDGI) (U.S. application Ser. No. 09/538,709, now PCT publication No. WO 01/75180, which is hereby incorporated herein by reference), which reduced the redundancy of the printed library, and (2) a subtraction library, to enrich for stroke specific genes. As a result, the Stroke chip consists of -non-redundant clones specific for stroke and hypoxia in primary neurons. The microarray contains 10,000 cDNA clones. The libraries printed on the Stroke chip were as follows:

TABLE 1

| Type of Library | Material | | Time points | | | |
|---|---|---|---|---|---|---|
| | In vivo | In vitro | 3h | 6h | 16h | 24h |
| Subtraction Library (five independent libraries) | [MCAO] - [Sham] | | ■ | ■ | | |
| | [MCAO + FK506] - [MCAO] | | + | + | | |
| | | Primary neurons: [Hypoxia + FK506] - [Normoxia + FK506] | + | + | + | + |
| SDGI library (proof of 6 conditions) | MCAO | | + | | | |
| | MCAO + FK506 | | ■ | | | |
| | Sham + FK506 | | ■ | | | |
| | | Primary neurons: [Hypoxia] | ■ | | ■ | |
| | | Primary neurons: [Hypoxia + FK506] | | | ■ | |

The design of the Stroke chip: library types and cDNA sources. Each library is in a different shade of gray. Note that the four libraries found at the different time points in the third line of the table were combined into a single library, as were the four libraries of the seventh line.

B. Hybridization Scheme

Human Apoptosis (HAP) Chip: Eleven hybridizations were performed on the Human Apoptosis Chip (Table 2). The probes used for these hybridizations were derived from rats' brains. Rats were either untreated (Sham-operated) or treated (middle cerebral artery occlusion) with or without FK506.

TABLE 2

| HAP chip hyb. | Probe 1 | | | | Probe 2 | | | |
|---|---|---|---|---|---|---|---|---|
| | Probe ID | Probe label | Treatment | Probe type | Probe ID | Probe Label | Treatment | Probe type |
| 681 | FJ1B | Cy3 | MCAO 3 Hr | Total | FJ1A | Cy5 | Common control | Total |
| 683 | FJ3B | | Sham 3 Hr | Nuclear | FJ3A | | | |
| 684 | FJ4A | | MCAO 3 Hr | Nuclear | FJ4A | | | |
| 685 | FJ5A | | MCAO 3 Hr + | Nuclear | FJ5A | | | |
| 686 | FJ6A | | MCAO 3 Hr + | Total | FJ6A | | | |
| 687 | FJ7A | | MCAO 6 Hr | Total | FJ7A | | | |
| 688 | FJ8A | | MCAO 6Hr + | Total | FJ8A | | | |
| 689 | FJ9A | | SHR Sham 3 Hr | Total | FJ9A | | | |
| 690 | FJ10A | | SHR Sham 6 Hr | Total | FJ10 | | | |
| 691 | FJ11A | | SHR MCAO 3 Hr | Total | FJ11 | | | |
| 692 | FJ12A | | SHR MCAO 6 Hr | Total | FJ12 | | | |

Probes used for hybridizations on the Human Apoptosis Chip: common control probe (a mixture of total RNA extracted from cortex of sham operated rats and from primary neurons); The "Nuclear" probe type is the Nuclear RNA probe described in WO99/58718, the entire contents of which are hereby incorporated Stroke Chip: Hybridizations were performed on the streke Chip. Probes were derived from brains of SD and SHR and from primary neurons exposed to 16 hours of hypoxia (with or without FK506).

TABLE 3

In Vivo Set

| Probe name | LABEL | Treatment | 2 blocks: |
|---|---|---|---|
| FJ39B | Cy3 | SD MCAO 3 Hr FK | |
| FJ39A | Cy5 | Common control | |
| FJ40B | Cy3 | SD Sham 3 Hr FK | Probes 39 40 41 divided by 46 |
| FJ40A | Cy5 | Common control | |
| FJ41B | Cy3 | SD MCAO 3 Hr | Probes 42 43 45 divided by 47 |
| FJ41A | Cy5 | Common control | |
| FJ42B | Cy3 | SHR Sham 6 Hr | |
| FJ42A | Cy5 | Common control | |
| FJ43B | Cy3 | SHR Sham 3 Hr | |
| FJ43A | Cy5 | Common control | |
| FJ44B | Cy3 | SHR MCAO 3 Hr | * 44 Not Included in this run |
| FJ44A | Cy5 | Common control | |
| FJ45B | Cy3 | SHR MCAO 6 Hr | |
| FJ45A | Cy5 | Common control | |
| FJ46B | Cy3 | SD control | |
| FJ46A | Cy5 | Common control | |
| FJ47B | Cy3 | SHR control | |
| FJ47A | Cy5 | Common control | |

In Vitro Set

| Probe name | dye | Treatment, RNA source | |
|---|---|---|---|
| FJ31B | Cy3 | PN normoxia | |
| FJ31A | Cy5 | Common probe | * Divided By Biological Control: Probe No 31 |
| FJ32B | Cy3 | PN normoxia FK | |
| FJ32A | Cy5 | Common probe | |
| FJ33B | Cy3 | PN hypoxia 16 hr | |
| FJ33A | Cy5 | Common probe | |
| FJ34B | Cy3 | PN hypoxia 16 hr FK | |
| FJ34A | Cy5 | Common probe | |
| FJ35B | Cy3 | PN normoxia | |

TABLE 3-continued

| FJ35A | Cy5 | Common probe |
|---|---|---|
| FJ36B | Cy3 | PN normoxia FK |
| FJ36A | Cy5 | Common probe |

TABLE 3-continued

| | | |
|---|---|---|
| FJ37B | Cy3 | PN hypoxia 16 hr |
| FJ37A | Cy5 | Common probe |
| FJ38B | Cy3 | PN hypoxia 16 hr FK |
| FJ38A | Cy5 | Common probe |

C. Functional Analysis

In order to identify genes responsible for hypoxia-, glutamate- or dopamine-induced neuronal cell death, positive selection was performed using expression cDNA libraries in retroviral vector. Libraries were prepared from mRNA of human glioma or neuroblastoma cell lines and in both cases mRNA from both healthy and dying cells was used. Positive selection by hypoxia, by glutamate or by dopamine was done in the established human neuroblastoma cell line BE2C Differentiated human neuroblastoma cells BE2C are a suitable and reliable model for in vitro study of processes that occur in brain of patients suffering from acute and chronic neuronal damage. BE2C is a subclone of SK-N-BE (2) human neuroblastoma cell line. Unlike the parental cell line, which grows as a mixed population of adherent and floating cells, BE2C cells are strictly adherent. The cells have polygonal form and grow as clusters of flattened neuroblasts with numerous short cytoplasmic processes, while few cells may also have one long neurite. The BE2C cells exhibit moderate levels of tyrosine hydroxylase and dopamine beta hydroxylase activity. They contain neurofilaments and specifically express D2-dopaminergic, alpha2-adrenergic, m2/m4-muscarinic and delta-opioid receptors. We have modified BE2C cells to express the retroviral ecotropic receptor. This manipulation made the modified cells suitable for retroviral gene delivery. The library was delivered by retroviral transduction with further induction of cell differentiation into a neuron-like phenotype. Every cell after differentiation expresses a unique library-derived cDNA (i.e., cells that obtained a cDNA fragment with an anti-apoptotic activity will not die upon application of hypoxia, dopamine, or glutamate). The protecting sequences were rescued from the surviving cells by RT-PCR and further analyzed. Several rounds of selection were performed for additional enrichment of protective elements. The corresponding full-length genes are likely to code for neuronal cell death-related proteins in hypoxic/ischemic neurons.

D. Bioinformatics Analysis

The data obtained from all microarray hybridization experiments were analyzed by bioinformatics experts, in several steps:

1. Selection of cDNA clones from expression data: cDNA clones were selected by comparison of gene expression patterns according to pre-defined criteria (See Sections XIX G and H for Apoptosis and Stroke chip, respectively). Selected clones were sequenced.

2. Sequence annotation: All sequences were annotated using a sequence annotation platform which includes:

Sensitive filtering of repetitive sequences (Smith-Waterman algorithm).

Homology searches in the non-redundant protein database (nr), (Frame_n2p algorithm), nucleotide database (nt) (gapped Blast algorithm) and ESTs database (dbEST) (Smith-Watermann algorithm).

Assembly of EST contigs for unidentified sequences, by automated EST-clustering software.

3. Literature analysis: The annotated sequences were studied in light of the biomedical literature, in order to select preferred gene candidates for further research.

E. Preparation of Tissues for in situ Hybridization

Coronal sections were prepared from paraffin blocks of sham operated rat brains and brains subjected to MCAO. A trial in situ hybridization experiment was performed using PGK probe to define the optimal prehybridization treatment of sections. After establishing the optimal conditions for in situ hybridization additional sections were hybridized to c-fos specific probe. Results of this hybridization demonstrated upregulation of c-fos expression at the side ipsilateral to occluded artery in all MCAO samples. Microscopically, hybridization signal locates to the cortical and striatal neurons. It must be noted that in most of the sham-operated samples, a weak activation of c-fos was detected in some cortical neurons at the side ipsilateral to operation. This could point to a possibility that other genes could show similar behavior, thus diminishing differential expression assessed by comparison between MCAO and sham-operated samples. Altogether, suitability of obtained paraffin blocks for in situ hybridization study was demonstrated allowing further validation of candidate genes.

F. In vitro experiments in Primary Neuron Cultures

Due to the relatively small proportion of neurons in brains (compared to glia cells), cultured primary neurons exposed to hypoxia were used as an additional in vitro model system. A primary neuron culture derived from cerebellum of 7 day old rat pups was used. The duration of hypoxia and FK506 concentrations were optimized for exerting an optimal neuroprotective effect in vitro, and 16 h hypoxia and 100 ng/mL of FK506 were selected (FIG. 1). The extracted RNA was used both for probes and for Stroke chip preparation.

G. Hybridizations on the HAP Chip

Differential expression data obtained by the 11 hybridizations on the HAP microarray (Table 2), was analyzed according to several pre-set criteria. Since a common reference probe was used in all hybridizations (common control, Table 2), different experiments could be compared to each other.

The criteria used for this analysis was a significant increase or decrease from control 3 hours after MCAO using either a nuclear or a total probe, and either with or without FK506, or 6 hours after MCAO using a total probe, with or without FK506. In order to distinguish between FK506 dependence and MCAO dependence, the differentially regulated genes were compared following MCAO treatment with those particularly enhanced by FK506 after MCAO. Three genes are reported here which were upregulated by MCAO treatment (without FK506) vs. sham but were downregulated when FK506 was present (vs. MCAO). These would be expected to be bad genes, as is the gene found to be upregulated after MCAO treatment. The two genes in Table 4 which were upregulated when FK506 was present would be expected to be good genes which could serve as potential indicators of the protective effect of FK506 in stroke.

The total and nuclear probes yielded distinct sets of differentially expressed genes, stressing the role of the different cDNA probes in highlighting different molecular events. It should be noted that at 3 hours MCAO (without FK506 treatment), a substantially higher number of differentially expressed genes was detected by a nuclear probe compared to a total probe, albeit in different rat strains. This further stresses the importance of the nuclear probe in detecting early gene transcription events, implicated in acute responses.

All clones were sequenced, annotated, and evaluated where possible in light of the biomedical literature. Table 4 lists certain novel genes that were selected according to their potential interest.

TABLE 4

Genes Selected for Further Analysis frrom the HAP Chip

| Clone | SEQ ID NO | Annotation | NCAO Dependent | FK506 Dependent | Good/ Bad |
|---|---|---|---|---|---|
| HAP-91F7 | 1 | Similar to EST03783 *Homo sapiens* (T05894) | 6 h Total (2.14) | | bad |
| HAP-2F5 | 2 | Novel | | 6 h Total (2.09) | good |
| HAP-2E5 | 3 | Novel | | 6 h Total (4.72) | good |
| HAP-8C7 | 4 | Novel | 3 h Total (2.07) | 3 h Nuc. (−2.08) | bad |
| HAP-2C3 | 5 | Novel | 3 h Total (2.16) | 3 h Nuc. (−2.33) | bad |
| HAP-6C1 | 6 | Novel | 3 h Total (2.33) | 3 h Nuc. (−2.17) | bad |

H. Hybridizations on the Stroke Chip

Thirty-four hybridizations were performed on the stroke chip (Table 3). Table 5 lists genes that were selected on the basis of these hybridizations. The genes identified using the STR chip are grouped in Table 5 according to results of hybridization with different probes. The same gene may be listed in more than one group.

Group 1: Genes upregulated by hypoxia in vitro. This group contains 38 novel genes which give differentials higher than 1.6 upon hybridization with probes representing RNA from primary rat neurons incubated for 16 h in hypoxic conditions, in the presence of FK506 or without it (see columns FJ33B, FJ37B, FJ34B and FJ38B of Table 5, in conjunction with Table 3).

Group 2: Genes upregulated in brains of rats after 3 h of MCAO and also in sham operated Sprague-Dawley rats (SD rats) with FK506, as well as upregulated in SHR rats after 6 h of MCAO (see columns FJ39B, FJ40B, FJ41B and FJ45B of Table 5). This group includes two novel genes.

Group 3: Genes upregulated only in SD rats which have received either MCAO or a sham operation (see columns FJ39B, FJ40B and FJ41B of Table 5). This group includes 4 novel genes.

Group 4: Genes upregulated only in SHR rats (see particularly column FJ42B of Table 5). This group includes one novel gene.

Group 5: Genes downregulated by hypoxia in primary neurons (see particularly columns FJ33B, FJ37B, FJ34B and FJ38B of Table 5). This group includes 3 novel genes.

Group 6: Genes downregulated only in SD rats (see columns FJ39B, FJ40B and FJ41B of Table 5). This group includes one novel gene.

Group 7: Genes oppositely regulated in operated SD rats versus primary neurons in hypoxia (compare columns FJ39B, FJ40B and FJ41B with columns FJ33B, FJ34B, FJ37B and FJ38B of Table 5). This group includes three novel genes.

Group 8: Genes oppositely regulated in SHR rats after MCAO versus primary neurons in hypoxia (compare column FJ45B with columns FJ39B, FJ34B, FJ37B and FJ38B of Table 5). This group includes one novel gene.

Group 9: Genes coregulated in vivo in MCAO model and in vitro in primary neurons in hypoxia (compare columns FJ39B, FJ41B and FJ45B with columns FJ33b, FJ34B, FJ37B and FJ38B in Table 5). This group includes two novel genes.

Group 10: Genes influenced by FK506 in the tests using probes derived from cells subjected to stress in vitro (see columns FJ34B and FJ38B in Table 5) or in the tests using probes derived from cells subjected to stress in vivo (see column FJ39B in Table 5). This group includes 15 novel genes.

While the genes in most of these groups could conceivably be either good or bad genes, as discussed above, the categorization can be accomplished without undue experimentation. It is expected, however, that those genes which were upregulated by MCAO without FK506 treatment (vs. sham), but downregulated when treated with FK506 (vs. MCAO without FK506) are bad genes. Those genes in Table 5 which are upregulated in column FJ41B and downregulated in column FJ39B are in this category. Thus, genes incorporating SEQ ID NOs: 60, 84 and 89 may be categorized as bad genes. As SEQ ID NO:93 is downregulated in column FJ41B and upregulated in column FJ39B, it may be categorized a good gene. Those genes upregulated in hypoxia cells sixteen hours after FK506 treatment (column FJ34B or FJ38B) fall into the category of good genes. These include genes incorporating SEQ ID NOs: 7–57, 61–63, 78–81 and 83–85. More preferred of these are SEQ ID NOs: 49 (KIAA0893), 50, 51 (both corresponding to KIAA0911), 85 (KIAA0735) and 87 (corresponding to, KIAA0323) Conversely, those genes downregulated in the same columns may be categorized as bad genes, i.e., genes incorporating SEQ ID NOs: 68–71, 74–77 and 82.

TABLE 5

| Seq ID # | Gene Description | Gene ID | FJ43B | FJ42B | FJ40B | FJ41B | FJ39B | FJ45B | FJ35B | FJ32B | FJ36B | FJ33B | FJ37B | FJ34B | FJ38B |
|---|---|---|---|---|---|---|---|---|---|---|---|---|---|---|---|
| | | | | | Group 1: Upregulated by Hypoxia In Vitro | | | | | | | | | | |
| 7 | none:01_STR_39H12_T7.fa | STR-39H12 | 1.2 | 1 | -1.1 | -1.1 | -1 | -1.1 | 1 | 1.2 | 1.3 | 2.2 | 2.3 | 2.5 | 2.8 |
| 8 | none:04_STR_36F1_T7.fa | STR-36F1 | 1.1 | 1.1 | -1.2 | -1.1 | 1 | -1 | 1 | 1.3 | 1.5 | 2.8 | 2.6 | 2.9 | 3 |
| 9 | none:05_STR_36F12_T7.fa | STR-36F12 | 1.1 | 1.1 | -1.1 | -1.1 | 1.1 | -1.1 | 1.2 | 1.2 | 1.2 | 1.7 | 1.6 | 2 | 1.9 |
| 10 | none:06_STR_83F10_T7_F01_014.ab1.fa | STR-83F10 | 1.1 | 1.1 | -1.2 | -1.1 | -1.3 | 1.1 | -1.1 | 1.3 | 1.2 | 3.4 | 2.9 | 2.3 | 2.5 |
| 11 | none:08_STR_36H3_T7.fa | STR-36H3 | 1.1 | 1.3 | 1.4 | -1.1 | 1.2 | -1 | 1.3 | 1 | 1.1 | 2.3 | 2.5 | 2.9 | 2.7 |
| 12 | none:09_STR_19B3_T7.ab1.fa | STR-19B3 | -1.1 | 1 | -1.1 | -1.2 | 1 | -1 | 1.2 | 1 | 1.2 | 2.4 | 2.7 | 2.7 | 2 |
| 13 | none:09_STR_55A6_M13F.fa | STR-55A6 | -1 | 1 | -1.1 | -1.1 | -1.5 | 1.2 | 1.1 | -1.1 | -1 | 3 | 2.9 | 3 | 3 |
| 14 | none:09_STR_55A6_M13R.fa | | | | | | | | | | | | | | |
| 15 | none:33_STR_55A6_1_T7.ab1.fa | | | | | | | | | | | | | | |
| 16 | none:08_STR_37B5_M13F.fa | STR-37B5 | 1.1 | 1.1 | -1.1 | -1.3 | -1.1 | -1.2 | 1 | -1.1 | -1 | 1.9 | 1.9 | 1.9 | 1.8 |
| 17 | none:11_STR_37B5_T7.fa | | | | | | | | | | | | | | |
| 18 | none:13_STR_55B3_T7_E02_018.ab1.fa | STR-55B3 | -1 | 1.1 | -1.1 | 1 | -1.5 | 1.2 | -1.1 | -1.1 | -1 | 2.9 | 2.7 | 2.9 | 2.5 |
| 19 | none:14_STR_55E2_T7_F02_026.ab1.fa | STR-55E2 | 1 | 1.3 | -1.1 | -1 | -1.6 | 1.2 | -1.2 | -1.4 | -1.3 | 2.4 | 2.4 | 2.6 | 2.4 |
| 20 | none:66_STR_55E2_T7_B09_076.ab1.fa | | | | | | | | | | | | | | |
| 21 | none:15_STR_55F12_T7_G02_019.ab1.fa | STR-55F12 | 1 | 1.2 | -1.1 | -1.1 | -1.4 | 1 | -1.1 | -1.2 | -1.1 | 2.8 | 2.5 | 2.5 | 2.3 |
| 22 | none:16_STR_55H7_T7_H02_027.ab1.fa | STR-55H7 | 1 | 1.1 | -1.1 | -1.3 | -1.4 | -1.3 | 1.2 | -1.2 | -1.1 | 2.6 | 2.7 | 2.6 | 2.9 |
| 23 | none:17_STR_55H8_T7_A03_020.ab1.fa | STR-55H8 | -1.1 | 1.1 | -1.1 | 1.1 | -1.4 | -1.1 | 1.1 | -1.2 | 1 | 3.2 | 2.6 | 2.8 | 2.3 |
| 24 | none:17_STR_65C12_M13F.fa | STR-65C12 | 1.2 | -1.1 | 1.1 | 1.1 | 1 | -1.2 | -1.3 | -1.3 | -1.3 | 2 | 2 | 1.7 | 1.7 |
| 25 | none:38_STR_65C12_1_T7.fa | | | | | | | | | | | | | | |
| 26 | none:18_STR_55H11_T7_B03_028.ab1.fa | STR-55H11 | 1.2 | 1.1 | -1.1 | -1 | -1.4 | 1 | -1.1 | -1.1 | -1.2 | 2.6 | 2.7 | 2.5 | 2.5 |
| 27 | none:18_STR_65E6_M13F.fa | STR-65E6 | -1.2 | -1.2 | -1.1 | 1.1 | -1.1 | -1.1 | -1.2 | -1.3 | -1.2 | 1.9 | 1.9 | 1.7 | 1.8 |
| 28 | none:20_STR_65E6_M13R.fa | | | | | | | | | | | | | | |
| 29 | none:20_STR_65E6_M13F.fa | | | | | | | | | | | | | | |
| 30 | none:19_STR_101D5_M13F.fa | STR-101D5 | 1.2 | 1.2 | -1 | -1 | 1 | 1.2 | 1.2 | 1.3 | 1.4 | 2.3 | 2 | 1.8 | 1.9 |
| 31 | none:20_STR_S.12_5_T7.fa | | | | | | | | | | | | | | |
| 32 | none:49_STR_101D5_1_T7.ab1.fa | | | | | | | | | | | | | | |
| 33 | none:26_STR_41F5_M13R.fa | STR-41F5 | 1.2 | 1.1 | -1.2 | 1.2 | -1.1 | -1.1 | 1.1 | 1.2 | 1.3 | 2.3 | 2.5 | 2.4 | 2.7 |
| 34 | none:26_STR_5D12_T7.ab1.fa | STR-5D12 | -1 | -1.4 | 1 | -1 | -1.1 | -1.3 | 1.2 | -1 | 1 | 2.3 | 2.5 | 2.5 | 2.2 |
| 35 | none:30_STR_55C5_M13F.fa | STR-55C5 | -1.1 | -1.2 | 1.1 | -1.3 | -1.1 | -1.1 | 1 | 1 | 1.1 | 2.1 | 1.7 | 1.7 | 1.8 |
| 36 | none:32_STR_38D9_T7.fa | STR-38D9 | -1.1 | -1.1 | -1.1 | 1.1 | -1 | -1.2 | 1.1 | 1.2 | 1.3 | 2.8 | 2.6 | 3.2 | 3 |
| 37 | none:38_STR_42C8_T7.fa | STR-42C8 | 1.1 | -1.2 | 1.1 | -1.4 | -1.4 | -1.2 | 1.1 | 1.1 | 1.1 | 2.3 | 2.4 | 2.2 | 2 |
| 38 | none:41_STR_889_T7.ab1.fa | STR-8B9 | 1.1 | 1 | 1.1 | -1.1 | 1.4 | 1.1 | 1 | 1 | 1.1 | 3.4 | 3.8 | 3.7 | 3.5 |
| 39 | none:43_STR_95H10_T7_C06_049.ab1.fa | STR-95H10 | 1.2 | 1.1 | -1 | -1.2 | -1.6 | 1.1 | -1.1 | -1.1 | -1 | 3.3 | 3.1 | 2.8 | 3 |
| 40 | none:56_STR_95H10_T7_H07_063.ab1.fa | | | | | | | | | | | | | | |
| 41 | none:44_STR_65E3_T7_D06_057.ab1.fa | STR-65E3 | -1.2 | 1 | -1.2 | 1.2 | -1.1 | -1.1 | -1.1 | -1.2 | -1.1 | 2.1 | 2.7 | 1.8 | 2.1 |
| 42 | none:45_STR_42F8_T7.fa | STR-42F8 | 1.1 | 1.1 | 1 | -1 | 1 | -1.1 | 1.1 | -1.1 | 1.3 | 2.1 | 2.1 | 2.6 | 2.6 |
| 43 | none:55_STR_47E5_T7_G07_055.ab1.fa | STR-47E5 | 1.3 | 1.4 | 1.1 | -1.1 | 1.2 | 1.3 | 1.1 | 1.1 | 1.2 | 1.6 | 1.6 | 1.7 | 2.1 |
| 44 | none:78_STR_50B9_T7_F10_090.ab1.fa | STR-50B9 | 1 | -1 | -1.2 | 1.1 | 1 | -1.1 | 1.1 | 1.2 | 1.4 | 3 | 2.8 | 3.6 | 2.7 |
| 45 | none:01_STR_42H7_M13F.fa | STR-42H7 | 1.1 | 1.1 | -1.1 | -1 | 1 | -1.1 | -1 | 1.2 | 1.2 | 2.1 | 1.9 | 2.2 | 2.3 |
| 46 | none:01_STR_42H7_M13F.fa | | | | | | | | | | | | | | |
| 47 | none:10_STR_48B6_M13F.fa | STR-48B6 | 1.2 | | | -1 | | -1 | 1.1 | 1.4 | 1.4 | 2.7 | 2.7 | 2.8 | 3.2 |
| 48 | none:10_STR_48B6_M13R.fa | | | | | | | | | | | | | | |
| 49 | Homo sapiens KIAA0893 protein (KIAA0893), mRNA; nt_non_genomic(identity)25_STR_5D2_T7.ab1.fa | STR-5D2 | 1 | -1.1 | 1.1 | -1.1 | 1 | 1 | 1 | 1.3 | 1.2 | 2.8 | 3.1 | 3.4 | 3 |
| 50 | none:13_STR_32D4_1_T7.ab1.fa | STR-32D4 | -1 | -1.4 | -1 | -1 | | -1.4 | 1 | 1.4 | 1.4 | 1.6 | 1.6 | 1.7 | 1.8 |
| 51 | none:90_STR_32D4_MI3F_B12_096.ab1.fa | | | | | | | | | | | | | | |

TABLE 5-continued

| Seq ID # | Gene Description | Gene ID | FJ43B | FJ42B | FJ40B | FJ41B | FJ39B | FJ45B | FJ35B | FJ32B | FJ36B | FJ33B | FJ37B | FJ34B | FJ38B |
|---|---|---|---|---|---|---|---|---|---|---|---|---|---|---|---|
| 52 | none:82_STR_50E5_T7_B11_092.abl.fa | STR-50E5 | -1 | -1.1 | -1 | -1 | -1 | -1.1 | 1.1 | 1.2 | 1.1 | 1.5 | 1.7 | 1.6 | 1.8 |
| 53 | none:74_STR_76C2_1_T7.abl.fa | STR-76C2 | 1.1 | 1.1 | -1.1 | 1.1 | -1.5 | 1.2 | 1 | -1.1 | -1.3 | 3 | 2.8 | 2.7 | 2.4 |
| 54 | none:14_STR_39E12_M13F.fa | STR-39E12 | -1.2 | -1 | -1 | 1.3 | 1.1 | 1 | 1 | 1 | 1.1 | 1.6 | 1.8 | 1.8 | 1.9 |
| 55 | none:12_STR_S.60_6_T7.fa | STR-102H10 | 1 | -1.4 | 1.1 | 1 | -1 | -1.1 | 1 | 1.4 | 1.2 | 2.3 | 1.6 | 1.9 | 1.8 |
| 56 | none:31_STR_59E12_M13F.fa | STR-59E12 | 1 | -1.1 | -1.2 | -1.2 | -1.2 | 1.1 | 1.1 | -1.2 | -1.2 | 2.1 | 1.9 | 2.3 | 1.9 |
| 57 | none:34_STR_59E12_1_T7.abl.fa | | | | | | | | | | | | | | |

Group 2: Upregulated by 3 hrs MCAD/Sham-FK in SD Rats and 6 hrs MCAO in SHR Rats

| 58 | none:45_STR_8G3_T7.abl.fa | STR-8G3 | 1.6 | 1.4 | 1.8 | 2.3 | 2.7 | 1.8 | 1.1 | 1.3 | 1.2 | 1.2 | 1.1 | 1.3 | 1.2 |
| 59 | none:54_STR_15G9_T7_F05_046.abl.fa | STR-15G9 | 1.2 | 1 | 1.4 | 4.8 | 2.7 | 3 | -1.1 | -1.3 | -1.2 | 1.1 | -1.1 | -1.1 | -1.3 |
| 60 | none:95_STR_15G9_T7.abl.fa | | | | | | | | | | | | | | |

Group 3: Upregulated Only in SD Rats

| 61 | none:24_STR_S.35_6_T7.fa | STR-102A2 | 1 | 1.2 | 2.5 | 3.4 | 3.1 | 1.2 | 1 | 1.3 | 1.3 | 1.6 | 1.2 | 1.6 | 1.3 |
| 62 | none:20_STR_77E1_T7_D03_029.abl.fa | STR-77E1 | 1.1 | 1.2 | 2.8 | 3.7 | 3.7 | 1.1 | -1.1 | 1.2 | 1.4 | 1.4 | 1.3 | 1.5 | 1.7 |
| 63 | none:85_STR_77E1_T7_E11_086.abl.fa | | | | | | | | | | | | | | |
| 64 | none:92_STR_15C5_T7.abl.fa | STR-15C5 | 1.4 | -1.1 | 1.6 | 1.6 | 1.7 | 1.1 | 1 | -1.2 | -1.1 | -1.4 | -1.4 | -1.4 | -1.4 |
| 65 | none:68_STR_11D5_T7.abl.fa | STR-11D5 | 1.2 | -1.1 | 2.8 | 3.2 | 4.1 | 1.3 | 1.2 | 1.4 | 1.4 | 1.2 | -1.1 | 1.3 | 1.6 |

Group 4: Upregulated Only in SHR Rats

| 66 | none:10_STR_71H11_M13R.fa | STR-71H11 | 1.4 | 1.6 | 1 | 1.2 | 1.1 | 1.5 | 1 | 1.2 | 1.1 | 1.1 | -1.1 | 1.1 | 1 |
| 67 | Homo sapiens KIAA0103 gene product (KIAA0103). mRN non_genomic(identity):35_STR_71H11_M13F.fa | | | | | | | | | | | | | | |

Group 5: Downregulated by Hypoxia in Primary Neurons

| 68 | none:33_STR_60H2_T7_A05_036.abl.fa | STR-60H2 | 1.2 | 1.1 | -1 | -1.1 | -1.1 | 1.1 | -1.1 | -1.3 | -1.3 | -1.5 | -1.6 | -1.6 | -1.6 |
| 69 | none:16_STR_8H4_M13F.fa | STR-8H4 | -1.1 | 1 | -1.1 | -1.1 | -1.1 | -1 | -4.5 | -4.3 | -5.2 | -5.1 | -4.5 | -5 | -5 |
| 70 | none:29_STR_8H4_M13R.fa | | | | | | | | | | | | | | |
| 71 | none:06_STR_54A11_T7_F01_014.abl.fa | STR-54A11 | 1 | -1.1 | -1.3 | -1.2 | -1.3 | -1 | -1.1 | 2.3 | 1.1 | -1.6 | -1.8 | -1.9 | -1.6 |

Group 6: Downregulated Only in SD Rats

| 72 | none:21_STR_S.54_5_T7.fa | STR-102F3 | -1.3 | -1 | -2.6 | -1.7 | -1.6 | -1.2 | 1.1 | 1.2 | 1.3 | 1 | -1.1 | 1.2 | 1.2 |
| 73 | none:55_STR_102F3_1_T7.abl.fa | | | | | | | | | | | | | | |

Group 7: Oppositely Regulated in Operated SD Rats and Primary Neurons/Hypoxia

| 74 | none:19_STR_21AB_T7.abl.fa | STR-21A8 | 1.7 | -1.1 | 1.8 | 1.8 | 1.5 | 1.2 | 1 | -1.1 | -1.1 | -2.8 | -3 | -3.3 | -3.1 |
| 75 | none:22_STR_21H9_T7.abl.fa | STR-21H9 | 1.7 | -1.1 | 1.7 | 1.5 | 1.4 | 1.3 | 1.3 | 1.1 | 1.2 | -2.6 | -2.4 | -2.8 | -2.6 |

Group 8: Oppositely Regulated in SHR/MCAO and in Primary Neurons/Hypoxia

| 76 | Homo sapiens EST from clone 251760, 5′ end; nt_non_genomic(identity):24_STR_31G6_T7_Hnon_g enomic(identity):65_STR_31G6_T7.abl.fa | STR-31G6 | -1 | 1.2 | 1.2 | 1.2 | 1.1 | 1.7 | 1.1 | 1.1 | -1.1 | -2.4 | -1.8 | -2.3 | -1.8 |
| 77 | | | | | | | | | | | | | | | |

Group 9: Genes Coregulated in MCAO and in Primary Neurons/Hypoxia

Group 10: Genes influenced by FK506 in Vitro

| 78 | 7e62e09.x1 Soares_NSF_F8_9W_OT_PA_P_S1 Homo sapien; est(identity):69_STR_11E11_T7.abl.fa | STR-11E11 | 1.6 | 1.6 | 1.6 | 2 | 2.1 | 1.7 | -1 | 1.1 | 1.2 | 1.7 | 1.5 | 1.7 | 1.6 |

TABLE 5-continued

| Seq ID # | Gene Description | Gene ID | FJ43B | FJ42B | FJ40B | FJ41B | FJ39B | FJ45B | FJ35B | FJ32B | FJ36B | FJ33B | FJ37B | FJ34B | FJ38B |
|---|---|---|---|---|---|---|---|---|---|---|---|---|---|---|---|
| 79 | none:09_STR_40E1_T7.fa | STR-40E1 | 1 | -1 | -1.2 | -1.1 | 1 | -1 | -1.1 | 1.2 | 1.2 | 1.5 | 1.6 | 1.9 | 2.1 |
| 80 | none:16_STR_41A8_T7.fa | STR-41A8 | -1 | 1 | -1 | -1 | 1 | -1.1 | -1.1 | 1.2 | 1.2 | 1.3 | 1.2 | 1.7 | 1.6 |
| 81 | none:24_STR_41D5_T7.fa | STR-41D5 | 1.2 | 1.1 | -1.1 | 1 | 1 | -1.1 | -1.1 | -1 | 1.2 | 1.4 | 1.5 | 1.7 | 1.9 |
| 82 | none:72_STR_75D9_T7_H09_079.ab1.fa | STR-75D9 | -1.2 | -1.3 | -1.2 | 1.1 | 1.1 | -1.1 | -1.4 | -1.5 | -1.2 | -1.5 | -1.4 | -1.7 | -1.9 |
| 83 | none:64_STR_31G3_T7.ab1.fa | STR-31G3 | -1.1 | -1.4 | -1.1 | -1.3 | -1.1 | -1.5 | 1.3 | -1 | 1.4 | 1.4 | 1.4 | 1.8 | 1.9 |
| 84 | none:52_STR_98F5_T7_D07_061.ab1.fa | STR-98F5 | -1.1 | -1 | -1.2 | 1.1 | -1.4 | 1.3 | 1.1 | 1.1 | 1.3 | 1.4 | 1.3 | 2 | 1.9 |
| 85 | Homo sapiens KIAA0735 gene product; synaptic vesi; nt_non_genomic(identity):07_STR_84C12_T7_G01_007.ab1.fa | STR-84C12 | 1.2 | 1.3 | 1.3 | 1 | 1.1 | 1.3 | -1 | 1.2 | 1.2 | 1.3 | 1.4 | 1.7 | 1.6 |
| 86 | none:43_STR_65B9_T7_C06_049.ab1.fa | STR-65B9 | 1.5 | -1 | 1.6 | 2.3 | 1.9 | 1.4 | -1.4 | -1.4 | -1.5 | 2 | 1.9 | 1.5 | 1.4 |
| | | | | | in Vivo | | | | | | | | | | |
| 87 | Human mRNA for KIAA0323 gene, partial cds; nt_non_genomic(identity):46_STR_12B5_T7_F04_042.ab1.fa | STR-12B5 | 1 | -1.1 | -1.4 | | -1.7 | -1.1 | 1 | 1.1 | 1.2 | -1 | 1 | -1.1 | 1 |
| 88 | Human mRNA for KIAA0323 gene, partial cds; nt_non_genomic(identity):73_STR_12B5_T7.ab1.fa | | | | | | | | | | | | | | |
| 89 | none:08_STR_86B5_T7_H01_015.ab1.fa | STR-86B5 | 1 | -1.2 | -1.1 | 1.1 | -1.6 | 1 | 1 | 1.2 | 1.4 | 1.1 | -1.1 | 1 | -1.1 |
| 90 | none:43_STR_80G8_1_M13F.fa | STR-80G8 | 1 | -1.1 | -1.2 | -1.2 | -1.8 | -1.1 | 1.1 | 1.5 | 1.4 | 1.2 | -1 | 1 | 1.2 |
| 91 | none:31_STR_77A12_T7.fa | STR-77A12 | 1.1 | -1 | -1.2 | -1.2 | -1.6 | -1.2 | 1 | -1.2 | -1.1 | -1 | 1.1 | 1.1 | 1.2 |
| 92 | none:81_STR_77A12_T7_A11_084.ab1.fa | | | | | | | | | | | | | | |
| 93 | none:23_STR_91B4_T7_G03_023.ab1.fa | STR-91B4 | 1 | 1 | -1 | -1.1 | 1.7 | -1.1 | -1 | 1.4 | 1.2 | 1 | -1.2 | -1.1 | -1.1 |

Six of the genes in Table 5 have been disclosed as undefined ESTs in sequence databases. Table 6 shows the known accession numbers with respect to these genes.

TABLE 6

| Gene ID | Accession No. | SEQ ID NO |
|---|---|---|
| STR-5D2 | gi\|7662363\|ref\|NM_014969.1\| | 49 |
| STR-71H11 | gi\|7661909\|ref\|NM_014673.1\| | 67 |
| STR-31G6 | gi\|8670869\|emb\|AL359650.1\|IROEST123 | 76 |
|  | gi\|8670869\|emb\|AL359650.1\|IROEST123 | 77 |
| STR-11E11 | gi\|9969291\|gb\|BE644980.1\|BE644980 | 78 |
| STR-84C12 | gi\|7662269\|ref\|NM_014848.1\| | 85 |
| STR-12B5 | gi\|2224586\|dbj\|AB002321.1\|AB002321 | 87 |
|  | gi\|2224586\|dbj\|AB002321.1\|AB002321 | 88 |

I. Results of Functional Profiling

Figure 2A:
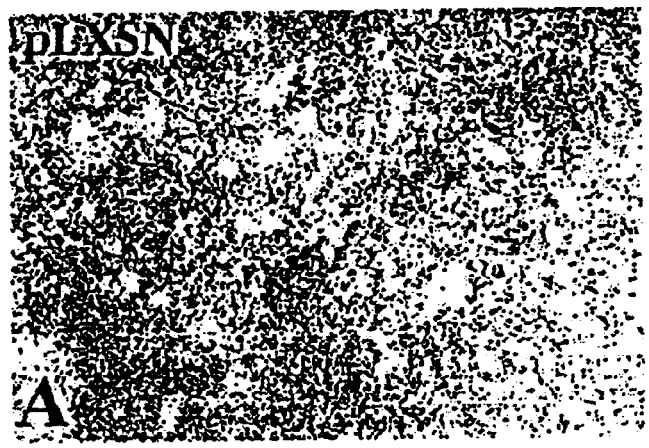
FIGS. 2A and 2B are microphotographs showing glutamate-induced killing of BE2C cells infected with an empty pLXSN vector (FIG. 2A) or the expression cDNA sub-library, following 2 rounds of selection (FIG. 2B) aimed for isolation of library clones resistant to glutamate toxicity by virtue of library-derived cDNA expression. A comparison of FIG. 2B with FIG. 2A shows that a significant portion of the cells infected with the enriched sublibrary was protected from the toxic effects of glutamate.
Figure 2B:
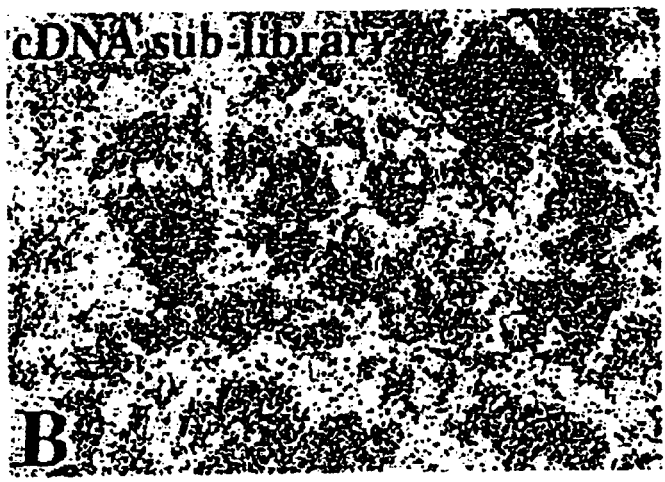

As described, positive selection in BE2C cells was employed in order to select for neuronal cell death-related proteins in hypoxic/ischemic neurons. The efficiency of the selection was illustrated in two ways:

1. BE2C cells infected with control empty retroviral vector (FIG. 2A) and with the sub-library of elements obtained after two rounds of enrichment (FIG. 2B). A significant portion of the cells infected with the enriched sub-library was protected against the toxic effect of glutamate.

Figure 3A:
FIGS. 3A and 3B show agarose gel electrophoresis of elements from libraries after 1 (FIG. 3A) and 4 (FIG. 3B) rounds of selection. Discrete bands can be seen in FIG. 3B in enrichment of certain protective cDNA fragments in the course of functional selection
Figure 3B:

2. Library elements from survived cell clones were rescued by PCR, after 4–5 rounds and after 1–2 rounds of selection, and separated by 2.5% agarose gel electrophoresis. As seen in FIG. 3 nice discrete bands were observed after 4–5 rounds of selection (FIG. 3A), in comparison to DNA smears in earlier rounds (FIG. 3B).

Thus, a library of decreased complexity and increased effect is obtained with repeated rounds of selections.

The output of functional analysis comprised many genes, some of which were found to be novel. Some were identical to those found as differentially expressed by hybridization analysis. Table 7 is a list of genes from the functional analysis output which are either novel or whose function was previously unknown.

TABLE 7

Functional Genes

| SEQ ID # | Name of Gene | Name of Clone | Accession No. |
|---|---|---|---|
|  | KIAAs |  |  |
| 94 | KIAA0538 (Ras-GAP like) | FUNDII1.53; FUNDII1.36 | AB011110 |
| 95 | KIAA0399 | FUNH1III.12 | AB007859 |
| 96 | KIAA0494 | FUNGIII.13 | AB007963 |
| 97 | KIAA0638 | FUNDII2.22 | AB014538 |
| 98 | KIAA0750 | FUNH5III.15 | AB018293 |
| 99 | KIAA0100 | FUNDIII3.59 | D43947 |
| 100 | KIAA0239 | FUNGII1.44 | DB7076 |
| 101 | KIAA1014 | FUNH2III.20 | AB023231 |
|  | ESTs |  |  |
| 102 |  | FUNHII1.75 | AA059375 |
| 103 |  | FUNGIII1.1 | AA300642 |
| 104 |  | FUNGII1.21 | AA305249 |
| 105 |  | FUNDII1.37 | AA325087 |
| 106 |  | FUNHII1.85 | AA610691 |
| 107 |  | FUNGII1.46 | AA730668 |
| 108 |  | FUNGII1.23 | AA737193 |
| 109 |  | FUNDII1.33 | AA960916 |
| 110 |  | FUNH4III.9 | AA974390 |

TABLE 7-continued

Functional Genes

| SEQ ID # | Name of Gene | Name of Clone | Accession No. |
|---|---|---|---|
| 111 |  | FUNGII1.15 | AA984133 |
| 112 |  | FUNDII1.54 | AA524678 |
| 113 |  | FUNGIII1.24 | THC216469 |
| 114 |  | FUNDIII3.55 | AI003295 |
| 115 |  | FUNDII1.29 | AI003295 |
| 116 |  | FUNDII1.49 | AI057127 |
| 117 |  | FUNDIII2.39 | AI085933 |
| 118 |  | FUNHII1.76 | AI124570 |
| 119 |  | FUNDII1.75 | AI222354 |
| 120 |  | FUNH2III.7 | AI423961 |
| 121 |  | FUNGIII2.32 | THC175379 |
| 122 |  | FUNDII1.18 | H10578 |
| 123 |  | FUNHII1.71 | H94806 |
| 124 |  | FUNHII1.64 | N28509 |
| 125 |  | FUNHII1.59 | N51767 |
| 126 |  | FUNGII1.5 | R16526 |
| 127 |  | FUNGIII1.23 | THC221157 |
| 128 |  | FUNDII1.5 | U92985 |
| 129 |  | FUNH2III.3 | W31179 |
| 130 |  | FUNGII1.37 | THC212363 |
| 131 |  | FUNH5III.8 | Z21350 |

J. Literature Review of Candidate Genes

The selected and annotated sequences were studied in light of the biomedical literature. We have currently completed the analysis of results obtained from differential expression profiling with the Apoptosis array (HAP). Preliminary results are presented for the Stroke array (STR) and functional profiling (FUN). Note, however, that several promising candidates have already emerged from this data, and further analysis and verification may yield additional ones.

Currently more preferred polynucleotides according to the present invention are SEQ ID Nos: 49 (corresponding to KIAA0893), 50 and 51 (corresponding to KIAA0911), 65 (corresponding to KIAA0284), 67 (corresponding to KIAA0103), 85 (corresponding to KIAA0735), 87 (corresponding to KIAA0323), and 94–100 (corresponding KIAA numbers presented in Table 7)

Currently most preferred embodiments according to the present invention are SEQ ID NO:65 (corresponding to KIAA 0284) and SEQ ID NO 94 (corresponding to KIAA0538, also identified as CAPRI), as discussed in detail herein above.

K. Validation of KIAA0538; in Vitro Results

In addition to the selection of candidate clones for use in screening assays, the utility of one of the currently most preferred embodiments KIAA 0538 was further validated by use of in vitro assays.

Figure 4:
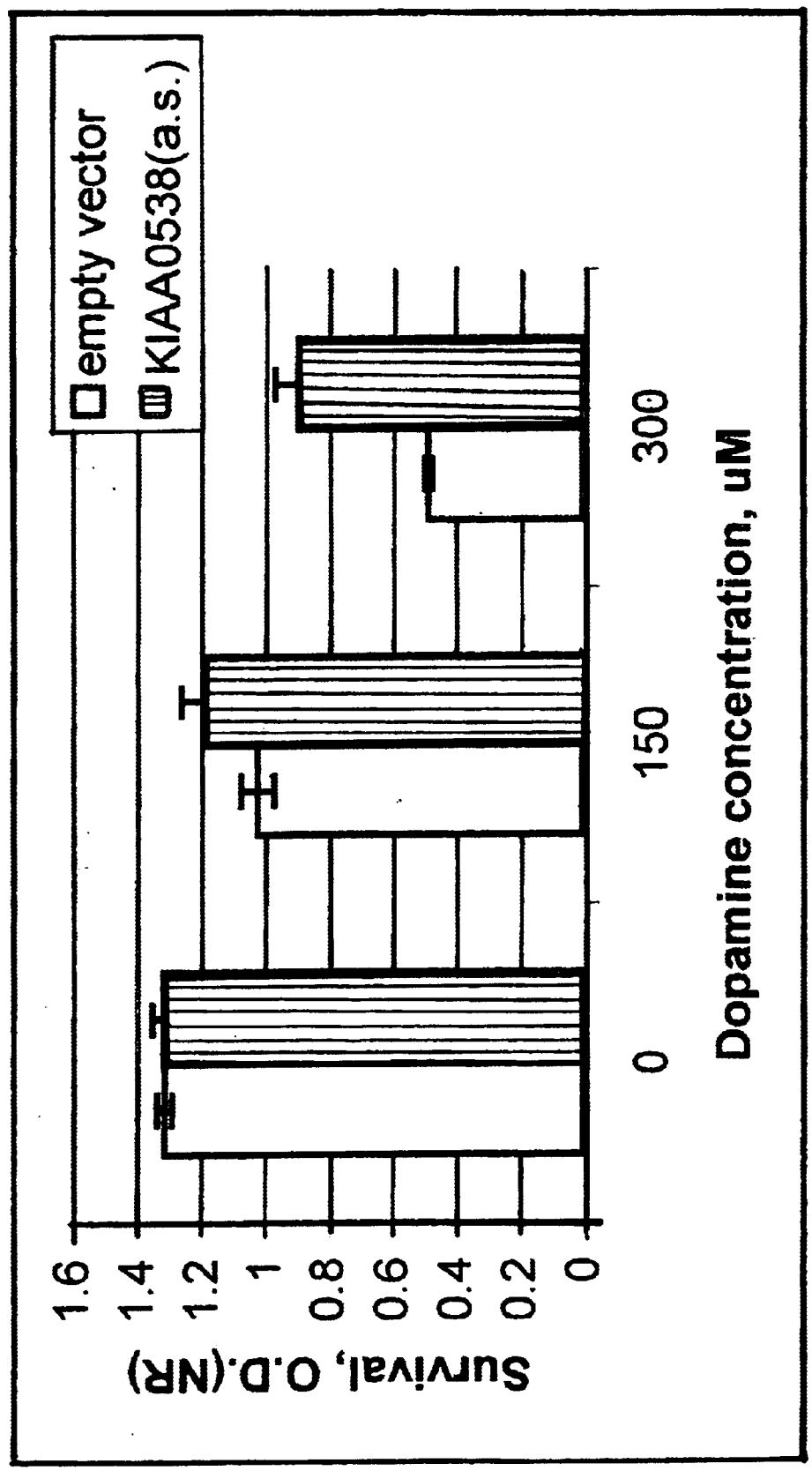
FIG. 4 shows the protection of infected BE2C cells (human neuroblastoma cells) expressing SEQ ID No 94 [i.e. library-derived antisense (a.s.) cDNA fragment of KIAA 0538] 24 hours after exposure to high dopamine concentrations, compared to control vector-transfected cells (PLXSN).Neutral red staining.
Figure 5:
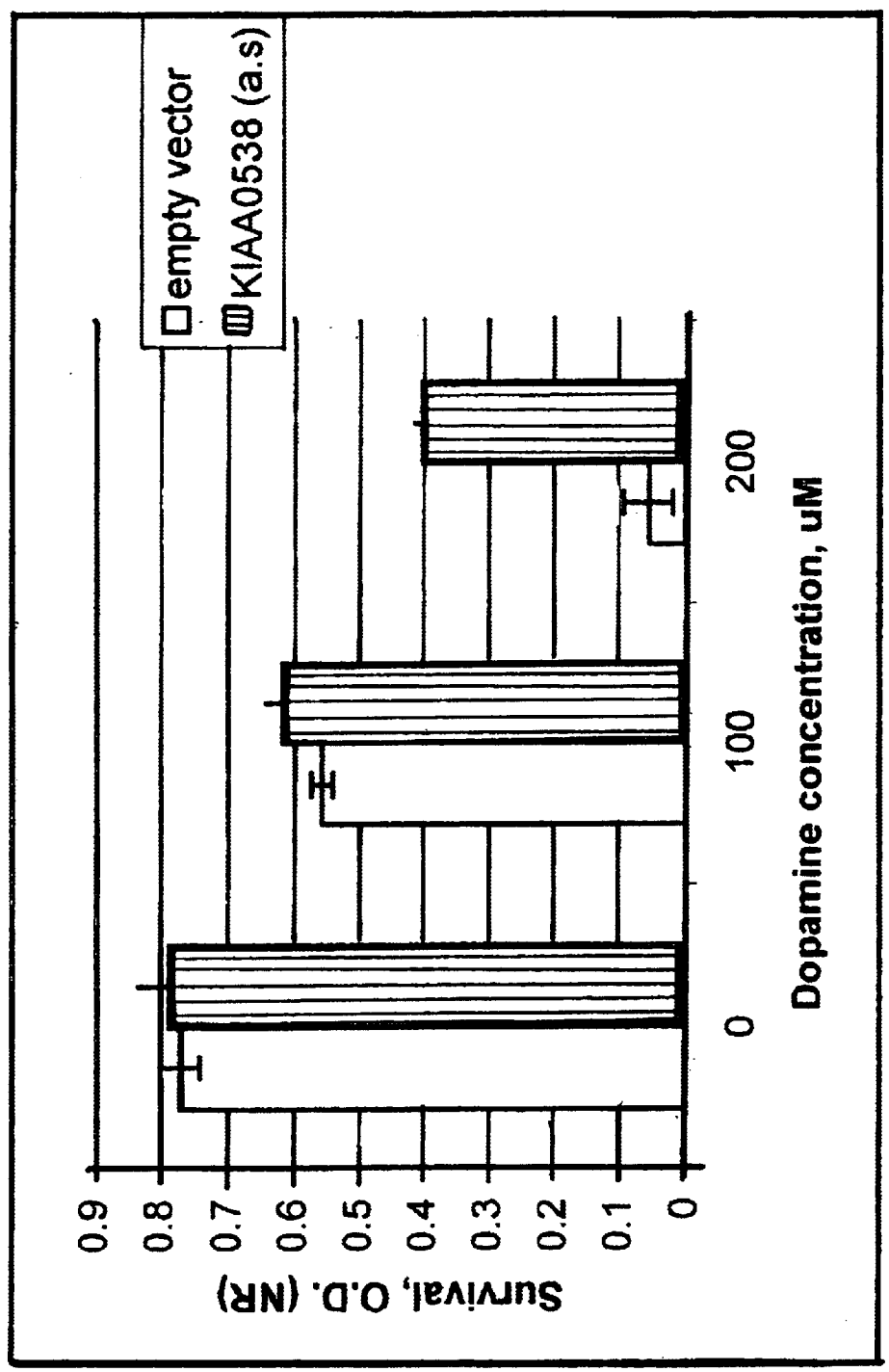
FIG. 5 shows the protection of transiently transfected BE2C cells expressing SEQ ID No 94 [i.e. library-derived antisense (a.s.) cDNA fragment of KIAA 0538] 24 hours after exposure to high dopamine concentrations, compared to control vector-transfected cells(PLXSN).Neutral red staining.

The aim of the experiment was validation of the fragment of KIAA0538 found using Dopamine selection (SEQ. I.D. No 94) which has 253 nucleotides. A slightly smaller fragment was used, wherein the first 12 of the nucleotides of SEQ. I.D. No 94 were replaced with 5 different nucleotides. The location of this smaller fragment (having 246 nucleotides) within the KIAA0538 cDNA is from nucleotide 2020 to nucleotide 2265. For purpose of validation, cells were studied either after decrease of the gene expression by means of transfection or transduction with an antisense expressing vector (the fragment rescued from the library during the functional screening), or after increased gene expression using transfection with a full length expression vector. For experiment, BE2C cells were seeded into 6-well plates at density 100,000 cells/well. Retroviral vector expressing KIAA0538 antisense fragment (rescued in functional selection) fragment or empty vector (pLXSN) were introduced in neuroblastoma cells by two different methods—transfection using Fugen6 reagent (Rosh) or by retroviral infection. Population of transfected/transduced cells was enriched by 3 days G418 selection. BE2C cells were further treated with different concentrations of Dopamine for 24 hours and assayed for viability by Neutral red staining (FIG. 4—infection; FIG. 5—transfection). As shown in FIG. 4 and FIG. 5 the antisense fragment of KIAA0538 is confers an increased cell survival at high Dopamine concentrations compared to control.

Figure 6A:
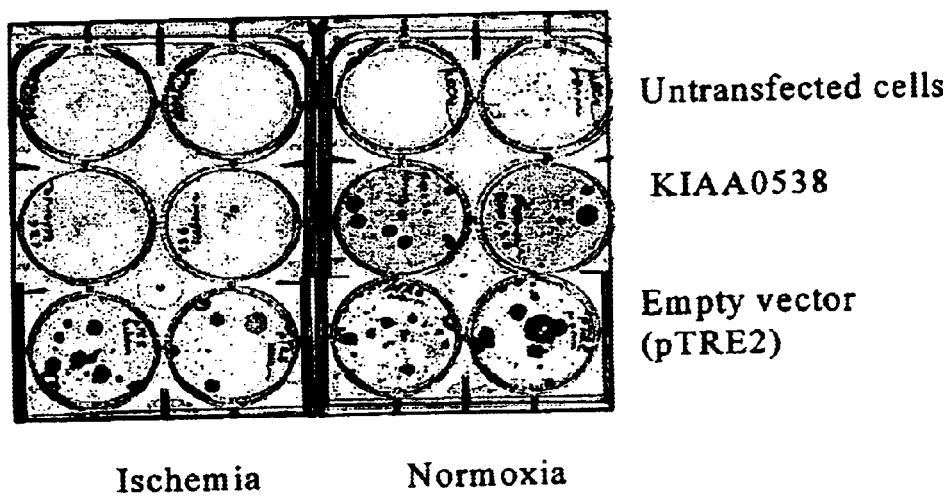
FIG. 6A shows the cytotoxic effect exerted by full length cDNA clone of KIAA 0538 in a colony formation assay (in P19 mouse embryonic stem cells) performed either in normoxic or hypoxic/low glucose(ischemic) conditions. This shows that the full length cDNA clone of KIAA 0538 sensitizes P19 cells in ischemic conditions, since there are very few colonies remaining, compared to the control (empty vector).
Figure 6B:
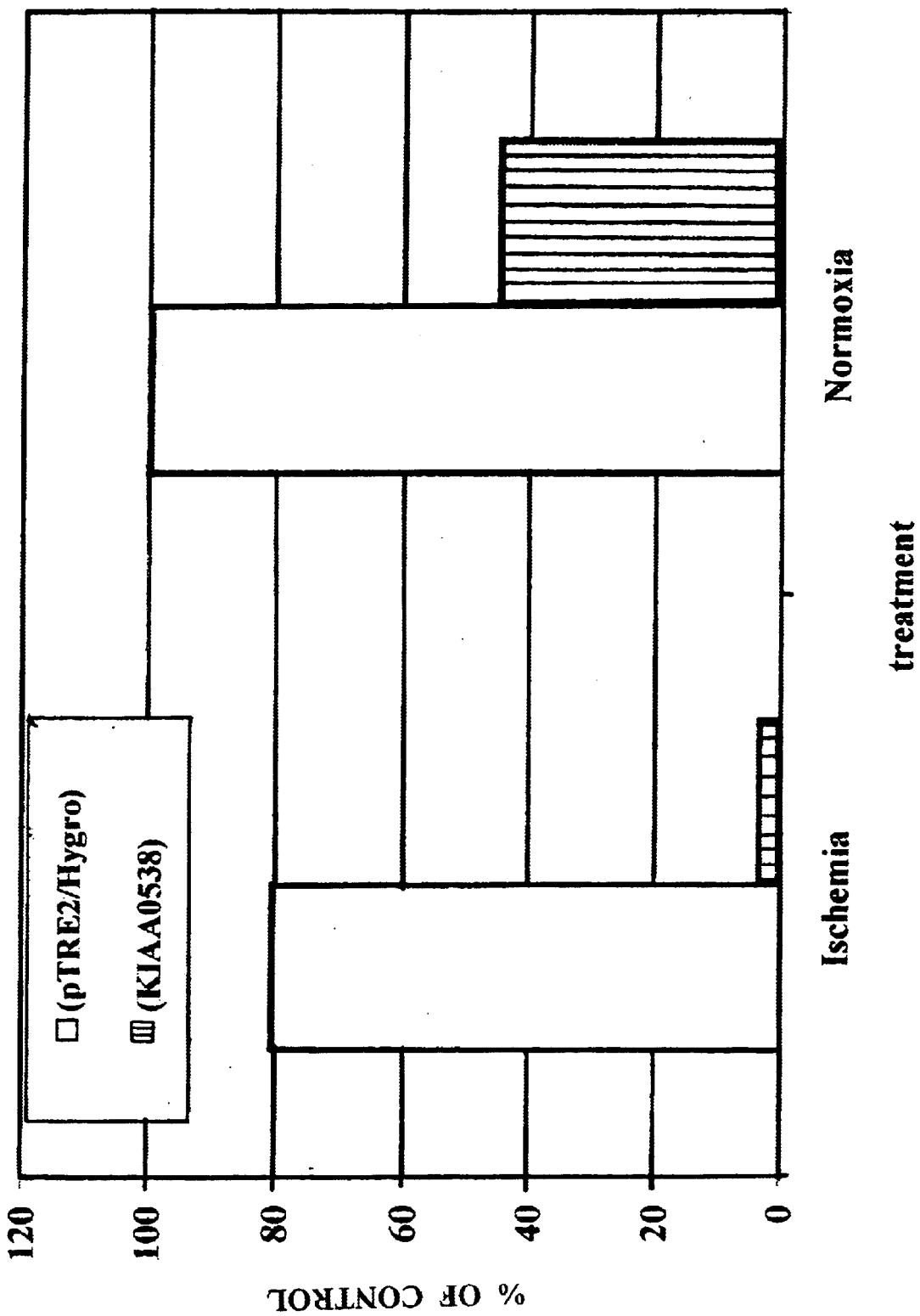
FIG. 6B is a graphical representation of FIG. 6A.

The effect of the full length KIAA0538 cDNA on cell survival was tested in colony formation assay in non-differentiated P19 cells stably expressing Tet-activator (confers high level of expression from responsive promoters). P19 cells were transfected with eithet empty vector or the same vector containing the full-length KIAA0538 cDNA under the control of Tet-repressible promoter. The number of transfected cells further taken for colony formation assay was normalized by cotransfection with GFP, so that the equal number of GFP-positive cells was taken for the assay. The cells were further plated and grown in the absence of tetracycline (to ensure the gene's expression) and in the presence of hygromycin (selectable marker) for 48 hours. Then part of the plates were subjected to 16 hours ischemia (0.5% O2 and no glucose) and following the transfer into normoxic conditions were further grown until the accomplishing of hygromycin selection (death of mock-transfected cells). The cell colonies grown in plates were fixed, stained with methylene blue and photographed with a CCD camera (FIG. 6). The area of the colonies was quantified using the IMAGE-Pro program. As shown in FIG. 6 gain of function (i.e., increased expression of KIAA0538) is detrimental to these cells even at normoxia and under hypoxia the cells overexpressing KIAA0538 are almost entirely non-viable Thus, we have obtained the experimental evidence that while overexpression of antisense KIAA0538 fragment protects BE2C cells from dopamine-induced toxicity, overexpression of the full-length cDNA is moderately cytotoxic under normoxic conditions and dramatically cytotoxic under ischemic conditions. Dopamine-induced cytotoxicity is known to have oxidative stress as its component (Offen, D. et al., 1999, Adv. Neurol, 80, 265–269) The same is true for ischemia (Shoshani et al., 2002, Mol Cell Biol.) It is known that buffering of intracellular calcium protects neuronal cells from death elicited by oxidative stress. The presence of calbindin in rat cortical neurons protects in vitro from oxidative stress. (Hugon J, Hugon F. Esclaire F, Lesort M, Diop AG, Brain Res 1996 Jan 29;707(2): 288–92). Thus, Ca2+ appears as a mediator of cytotoxicity produced by oxidative stress. It is also known that ischemic injury in stroke is associated with excitotoxicity (Horn J, Limburg M. Calcium antagonists for ischemic stroke: a systematic review.Stroke. 2001 Feb;32(2):570–6) and that KIAA0538 is activated by increased ca concentrations. Thus, activation of KIAA0538 should accompany numerous ischemic and neurodegenerative disorders making the ischemic cells more vulnerable to the injury. In accord, we have demonstrated the rescue of cells from apoptotic death by virtue of overexpression of KIAA0538 antisense fragment. Moreover, activated KIAA0538 was shown to suppress both Ras and ERK2 activation while the corresponding pathway is known to be involved in cell survival (Bonni A, Brunet A, West A E, Datta S R, Takasu M A, Greenberg M E. Cell survival promoted by the Ras-MAPK signaling pathway by transcription-dependent and -independent mechanisms. Science. 1999 Nov 12;286(5443): 1358–62). Altogether, our experimental and literature data argue that KIAA0538 is an attractive target for inhibition by drugs for treatment of ischemic and neurodegenerative diseases.

L. In vivo Utility

The pharmaceutical compositions of the present invention can be used for treatment of many diseases. By treatment of disease is meant prevention or amelioration of the disease or of symptoms associated with the disease, or minimizing subsequent worsening of the disease or of symptoms associated with the disease. The diseases to be treated include acute ischemic diseases, such as stroke, preferably, but also include myocardial infarction, acute renal failure, retinal artery occlusion, renal infarct, mesenteric ischemia and peripheral embolic events. The conditions to be treated also include chronic ischemic events such as peripheral vascular disease (PVD)and retinopathy. The diseases to be treated also include degenerative diseases causing chronic degenerative damage such as Parkinson's disease, Huntingdon's Chorea, Alzheimer's disease, amyotropic lateral sclerosis, multiple sclerosis, Shy-Drager Syndrome depression, bipolar diseases and Schizophrenia. Treatment of the effects of neurotoxicity, hypoxia, and/or ischemia in different organs, like e.g. brain, heart, liver, kidney is also envisaged as an aspect of the invention .

It will be appreciated that the most appropriate administration of the pharmaceutical compositions of the present invention will depend on the type of injury or disease being treated. Thus, the treatment of an acute event will necessitate systemic administration of the active composition comparatively rapidly after induction of the injury. On the other hand, diminution of chronic degenerative damage will necessitate a sustained dosage regimen.

The potential of preventing or reducing CNS injury by regulating gene expression or by modulating the action of the gene product of the invention is evaluated in animal models.

The models represent varying levels of complexity, by comparison of control animals to the treated animals. The efficacy of such treatment is evaluated in terms of clinical outcome, neurological deficit, dose-response and therapeutic window.

1. Closed Head Injury (CHI)—Experimental TBI produces a series of events contributing to neurological and neurometabolic cascades, which are related to the degree and extent of behavioral deficits. CHI is induced under anesthesia, while a weight is allowed to free-fall from a prefixed height (Chen et al, J. Neurotrauma 13, 557, 1996) over the exposed skull covering the left hemisphere in the midcoronal plane.

2. Transient middle cerebral artery occlusion (MCAO)—a 90 to 120 minutes transient focal ischemia is performed in adult, male Sprague Dawley rats, 300–370 gr. The method employed is the intraluminal suture MCAO (Longa et al., Stroke, 30, 84, 1989, and Dogan et al., J. Neurochem. 72, 765, 1999). Briefly, under halothane anesthesia, a 3-0-nylon suture material coated with Poly-L-Lysine is inserted into the right internal carotid artery (ICA) through a hole in the external carotid artery. The nylon thread is pushed into the ICA to the right MCA origin (20–23 mm). 90–120 minutes later the thread is pulled of, the animal is closed and let recover.

3. Permanent middle cerebral artery occlusion (MCAO)—occlusion is permanent, unilateral-induced by electrocoagulation of MCA. Both methods lead to focal brain ischemia of the ipsilateral side of the brain cortex leaving the contralateral side intact (control).

Evaluation Process

The efficacy of the treatment is determined by mortality rate, weight gain, infarct volume and by short and long term clinical and neurological outcomes in surviving animals. Infarct volumes are assessed histologically (Knight et al., Stroke, 25, 1252, 1994, and Mintorovitch et al., Magn. Reson. Med. 18, 39, 1991). The staircase test (Montoya et al., J. Neurosci. Methods 36, 219, 1991) or the motor disability scale according to Bederson's method (Bederson et al., Stroke, 17, 472, 1986) are employed to evaluate the functional outcome following MCAO. The animals are followed for different time points, ranging from hours up to two months. At each time point (24 h, 1 week, 3, 6, 8 weeks), animals are scarified and cardiac perfusion with 4% formaldehyde in PBS is performed. Brains are removed and serial coronal sections (200 m thick for example), are prepared for processing and paraffin embedding. They are stained with suitable dyes such as TCC. The infarct area is measured in these sections using computerized image analyzer.

Utilization of the treatments as is exemplified in the above animal models provides new possibilities for treatment of human brain injury or damage.

Table 8 is a list of all the sequences referred to hereinabove.

TABLE 8

SEQ ID NO: 1

>HAP_91F7_RF

CCAACTTGCCCGTTGTCCACGGGTCCCACCCCTTCTTGCCGCTCCTCCTCTGCAGGTCCCGC

CCTCTCCCCCTGCCTCACTCCCAATGTCTCCTTTGGCTAAGCCCCCTCCACAGGCCCCACCT

GCTCTGGCCACACCTCCTCTGCAGGCCCTTCCCTCTCCGCCTGCCTCATTCCCTGGGCAGGC

CCCTTTCTCACCCTCTGCCTCACTCCCAATGTCTCCTTTGGCCACGCCTCCTCCACAGGCCC

CACCTGTTCTGTAGTTAGTTA

SEQ ID NO: 2

>HAP_2F5_RF

CCAAGTCCACCCGATCACAAGGCTCAGCTCTTAAGTGCTCTGCGATACTGCTTTTCTAACAA

TGCCTGGTGCCTCCCTGAGTGAATTCCCAATAGGAGTCTTTCCACTTTAGTCCAACATGAGG

CAAGTAGTTGCAGGTGCCAGGTAACATAATGAGCTCCACCTTGGTAATCACTCTGAGTAGAC

AATGCTCAAAAAAACAGAGCACCACATAATGTATCAACCCTAACAGTCACCCTTCTGACATC

TCTATTGGAAAGAGGGGATAAGTAGTTAGTTA

SEQ ID NO: 3

>HAP_2E5_RF

CCTTTAAATTTTTACACTATCACACTTTATTTATTCAATCACCAAGCCCCACCTTATCTATT

CCCCTGCTCACACACAAATCCACTATTCTAATCCTGCTTACACACCCCTTCCACAGGGTTTT

ATCTCACTTATGATAAAATCCAAAACTCACAGCATAGCCACTCTCCCCAAAGCATACTATGC

TTTAACCACACTGGTCTTTCCTAAAAGTTTCTCCTATTCCCCAATCTTTCTTCCTTACTCTA

AGGTAGTTAGTTA

SEQ ID NO: 4

>HAP_8C7_RF

TAACTAACTAGGGAACCTGGGGGCCAAGGGGCCCCAGCAGTCAGCACCAATGCAATAGTCCT

TGAAGATCACGGCCAAAGCTATACTTGCTCTGGACAGGTAACTCCCCCTTTCATGGGCAGGG

GTGGTAAAAGGAGCAAGCAGAAGCAAAAAGGAATTTTCCTCTAAAAACAGAATTGCTGAAAG

GCACTTAATAGAGGGATAGGGGCCAGACACGGTGGCTCACACCTATAATCCCAGTACTTTAA

TAGGAAGAGGCTG

SEQ ID NO: 5

>HAP_2C3_RF

TAACTAACTATGCCAAAGGGAAATGTTAAGCTTGGGAACTGAGTCACGCAATAGCCTTTTGT

TABLE 8-continued

CCCTAAGCAGATGGCTGTAAGACAGAAGGTCACCTATCTCCCGAGTGG

SEQ ID NO: 6

>HAP_6C1_RF

TAACTAACTAGATAAGTGATCTGTGGCCACATTTGCAGTACGTGATCCTGACCCACTGGCCA

CTGCTAATTGGATAATAAGCAGCTACCACATCCAGTATGAGCCAGTCAGATCCTCTCTCTTG

GGAAACTAGCATTCACAGCCAGTGCCTCTACAGAGAAGGAAGCATAAGCATTTAGAAAGATA

GTTCTCCTGACTCTAGGGGGCCACTGGTAATAACAATCTCAGTTTCTGAGGCTTTCCAGTTT

CTGGATCC

SEQ ID NO: 7

01_STR_39H12_T7.fa

CCTCAGTAGGAGGGAGCGCGTGTGTGTGTGTGCGCGTGTGTGAGTGTGTGTAACAACCCA

GAAAGCTGGTAAGAGCTGCAGAGAGGCAGTGTTTATTAGATTCACACTTAGACACTGATTGT

GGGTTCTGGTTTAGCTCTTTTATAATTGTAAAGTTATATTTTTGCTGCTTTGTAATAGGATA

ATTCTTAAGCATCATCTTAAAATAGAGGTATTTTGATTCTTTTTTGTGGAGCTGTGACTAAA

GTGCAGNGTCTCACATAGGCTAAGCAAGTGCTGTGCACTGAGTTGAACCCCAGCAGAAGTAG

GTGCTGCAAGTGTAAAACAAGGCTAAAGGGCCTAATGCACACAGCCTGTGCAGGCCGCGAGT

GCACCGACTATAAGCCCCATGCTATTAAAGC

SEQ ID NO: 8

D4_STR_36F1_T7.fa

CCTCAGTAGGAGGGAGCGCGTGTGTGTGTGTGCGCGTGTGTGAGTGTGTGTAACAACCCA

GAAAGCTGGGAAGAGCTGCAGAGAGGCAGTGTTTATTAGATTCACACTTAGACACTGATTGT

GGGTTCTGGCTTAGCTCTTTTATAATTGTACAGCTATATTTTTGCTGCTTTGTAATAGGATA

ATTCTTAAGCATCATCTTAACATAGAGGTATTTTGCTTCTTTTTTGTGGCGCTTGACATTAA

CTGCAGCCTCTCACATAGGCTAAGCAAGTGCTGCGCACTTGAGTGAACTGCAGCAGAAGTAG

TCGCTGCACGTGTAAAACAAGGCTACAGATTCTAATGCACACAGCCTGTGCAGACCGCGTGT

CCACCGTCTATAAGGCATGGCTATAACGG

SEQ ID NO: 9

05_STR_36F12_T7.fa

CTTTAATAGCCATGGCCTTATAGACGGTGGCCACGCGGCCTGCACAGGCTGTGTGCATTAGG

CCCTTTAGCCTTGTTTTACACTTGCAGCACCTACTTCTGCTGGGGTTCAACTCAGTGCACAG

CACTTGCTTAGCCTATGTGAGACCCTGCACTTAATGCCCAGCACCACAAAAAAGAAACAAAA

TACCTCTATTTTAAGATGATGCTTAAGAATTATCCTATTACAAAGCAGCANAAATATAACTT

TACAATTATAAAAGAGCTAAACCAGGACCCACAATCAGTGTCTAAGTGTGAATCTAATAAAC

ACTGCCTCTCTGCAGCTCTTACCAGCTTTCTGGGTTGGTACACACACTCACACACGCGCACA

CACACACACACGCGCTCCCTCCTACTGAGG

SEQ ID NO: 10

06_STR_B3F10_T7_F01_014.abl.fa

TGGAGCTAATTGCGCGCGGCCGCGGTACGACGAACCTGCCCCTGATGACCCTCACCCCTTTT

GCATAGGTCACTGGATCCCACTGTCCTTCCTCGGTGCTTACACACTTTACAGACCCTTTAGG

CGAGCCCTTGCATAGAGCGTTATCTCAGTGCTCCATTCCAGTCCTGACTCCCTGTGGCCATT

TABLE 8-continued

GAGACTTTGGATTTAAGAACTCACATTGCTAGGGAGAGGGGCTTTGCTGGGAAAGGTGACTC

CTCTGTAACCTAGCCTCTTGTGCTCCTCCATGACAGAAATGCTGGGTGGAGTTTTACATTTG

CCAATGGCCAGCTTGTGAATATCTTCATATACACTTTCTATTCATGTTACTGTAGTTTCTGT

TTTGAAATAAAACTTCTGAATGTAAAAAAAAAAAAAAA

SEQ ID NO: 11

08_STR_36H3_T7.fa

CTTGGTCACAGTGCTTTCCTTACACCCTTATGATGAAAGTCACTGTAAGAAGGGCTGCTGGC

AGTCCAGGCACACCCTGTGTGCAGAGTCGGCCATGCTTTGGGAGGGTGTCAGGAAAGAGTCA

TTTACTTTGACTGCCTGTGGGCTGACTTCAGAACTTCAGGTCTTAAGGTTTGCTGGCTTCTG

AAAACACTTTCTAAAGAGCCCATGAAATATAAATATAACTAACTTAGAAAGCCCTG

SEQ ID NO: 12

09_STR_19B3_T7.abl.fa

TTTTTTTTTTTTTTTTTTTTTTAAAAATTCAAGGATGGGGTTAAAGGGGGAATTCCCGG

GGGGGGG

SEQ ID NO: 13

09_STR_55A6_M13F.fa

GGTACGGCGTACCTGCCTCCCAGTCTTCTCTTTTCTATAGCATGGCTTTAAGCCTGCCTCCT

TGACATGCTGTATATATTCTATTGTATTTGTTTCATTGTCCCACACTTAACTCAGGTGTGCT

AAAAATAAAAGTAAATTTTAACAGTCAAAAAAAAAAAAAAAAA

SEQ ID NO: 14

09_STR_SSA6_M13R.fa

TTTTTTTTTTTTTTTGGACGGTAAAAATTAACTTTAATTTTAAGCACACCTGAGTTAAGGG

GGGAACAATGAAACAAATCCAATAGAATTTTTACAGCATGTAAAGGAGGCAGGTTTAAAAGC

CATGCTATAAAAAAGAGAAAACTGGAAGGCAGGTACGCCGTACCGGGC

SEQ ID NO: 15

33_STR_55A6_1_T7.abl.fa

CTGCCTCCCAGTCTTCTCTTTTCTATAGCATGGCTTTAAAGCCTGCCTCCTTGACATGCTGT

ATATATTCTATTGTATTTGTTTCATTGTCCCACACTTAACTCAGGTGTGCTAAAAATAAAG

TAAATTTTAACAGTCAAAAAAAAAAAAAAAAAAGG

SEQ ID NO: 16

OB_STR_37B5_M13F.fa

CCATACAGTGCGCACTTCGAGTATAACAACGCGAGTGCAATGCTTTACCATGATGCATGAAG

AAAACTGAGGAGACAGATCAGCTACTATCGTAGCCATTACAGCTGAAGAGATTCAAAATTGG

AAGGCACTAACTGATTGCGTTAAGACGCATTCTATCAAGGTTATCATAGATGAAAGATCATA

GAAACTGGAAGGCATAAACTGAG

SEQ ID NO: 17

11_STR_37B5_T7.fa

CCATACAGTGCGCACTGCGAGACTCACAACGCGAGTGCAACGCATTACCATGATGCATGAAG

AAAACTGAGGAGACAGATCAGCTACTATCGAAGCCATTACAGCTGGAGAGATACTTACTGGG

TABLE 8-continued

AAGCCGCTAACTGATTGCGTTACGTCGAAATGTATCAAGGTTATCATAGATGAGAGATCATA

GAAACTGCTAGGCATACACTGAGCATTAAGCTTATCGACACCGTGGAGCTCGAGGTGAGTCC

ACGCACCAGCTGTGGGACCGTGTAGGGACTGNTACCTACGAGCATGGCGAGATCATAGGCAT

AGNNTNGTANTCA

SEQ ID NO: 18

13_STR_55B3_T7_E02_018.abl.fa

CTGCCTCCCAGTCTTCTCTTTTCTATAGCATGGCTTTAAAGCCTGCCTCCTTGACATGCNTG

ATATATTCTATTGTATTTGTTTCATTGTCCCACACTTAACTCAGGTGTGCTAAAAATAAAAG

TAAATTTTAACAGTCAAAAAAAAAAAAAAAAAAGG

SEQ ID NO: 19

14_STR_55E2_T7_F02_026.abl.fa

CGACGAACCTGCCTCCCAGTCTTCTCTTTTCTATAGCATGGCTTTAAAGCCTGCCTCCTTGA

CATGCTGTATATATTCTATTGTATTTGTTTCATTGTCCCACACTTAACTCAGGTGTGCTAAA

AATAAAAGTAAATTTTAACAGTCAAAAAAAAAAAAAA

SEQ ID NO: 20

66_STR_55E2_T7_B09_076.abl.fa

CTTCTCTTTTCTATAGCATGGCTTTAAAGCCTGCCTCCTTGACATGCTGNATATATTCTATT

GTATTTGTTTCATTGTCCCACACTTAACTCAGGTGTGCTAAAAATAAAAGTAAATTTTAACA

GTCAAAAAAAAAAAAAAA

SEQ ID NO: 21

15_STR_55F12_T7_G02_019.abl.fa

CGACGACCCTGCCTCCCAGTCTTCTCTTTTCTATAGCATGGCTTTAAAGCCTGCCTCCTTGA

CATGCNTGATATATTCTATTGGATTTGTTTCATTGTCCCACACTTAACTCAGGTGTGCTAAA

AATAAAAGTAAATTTTAACAGTCAAAAAAAAAAAAAAG

SEQ ID NO: 22

16_STR_55H7_T7_H02_027.abl.fa

CGACGAACCTGCCTCCCAGTCTTCTCTTTTCTATAGCATGCTTTAAAGCCTGCCTCCTTGA

CATGCTGTATATATTCTATTGTATTTGTTTCATTGTCCCACACTTAACTCAGGTGTGCTAAA

AATAAAAGTAAATTTTAACAGTCAAAAAAAAAAAA

SEQ ID NO: 23

17_STR_55H8_T7_A03_020.abl.fa

GGTACGACGAACCTGCCTCCCAGTCTTCTCTTTTCTATAGCATGGCTTTAAAGCCTGCCTCC

TTGACATGCTGTATATATTCTATTGTATTTGTTTCATTGTCCCACACTTAACTCAGGTGTGC

TAAAAATAAAAGTAAATTTTAACAGTCAAAAAAAAAAAA

SEQ ID HO: 24

17_STR_65C12_M13F.fa

GATCTGAGACCCACTTTGCAGACATGTGCACAGATGTGTTCCATTTCCCTATTTTTGCTGTA

GAGAAACAAGTAAATTTTCTTAGAGAATGAAAAAAAAAAAAAAA

SEQ ID NO: 25

38_STR_65C12_1_T7.abl.fa

TABLE 8-continued

CTAATTGCGCGCGGCCGCGGTACGACGACCCTGCGATCTGAGACCCACTTTGCAGACATGTG

CACAGATGTGTTCCATTTCCCTATTTTTGCTGTAGAGAAACAAGTAAATTTTCTTAGAGAAT

GAAAAAAAAAAAAAATAGGGCGCGCCTTTAAAACGGTTCCGATTTTTGGGCC

SEQ ID NO: 26

18_STR_5SH11_T7_B03_028.abl.fa

ACGACGACCCTGCCTCCCAGTCTTCTCTTTTCTATAGCATGGCTTTAAAGCCTGCCTCCTTG

ACATGCTNGATATATTCTATTGGATTTGTTTCATTGTCCCACACTTAACTCAGGTGTGCTAA

AAATAAAAGTAAATTTTAACGGTCAAAAAAAAAAAAAAA

SEQ ID NO: 27

18_STR_65E6_M13F.fa

GATCTGAGACCCACTTTGCAGACATGTGCACAGATGTGTTCCATTTCCCTATTTCTGCTGTA

GAGAAACAAGTAAATTTTCTTAGAGAATGAAAAAAAAAAAAAAAAAA

SEQ ID NO: 28

20_STR_65E6_M13F.fa

GGCGACGTACCTGCGATCTGAGACCCACTTTGCAGACATGTGCACAGATGTGTTCCATTTCC

CTATTTCTGCTGTAGAGAAACAAGTAAATTTTCTTAGAGAATGAAAAAAAAAAAAAAAA

SEQ ID NO.29

20_STR_65E6_M13R.fa

TTTTTTTTTTTTTTTTTAATTCTTTAAAAAAATTTACTGGTTTCTTTACAGCAAAAATAGG

GAAATGGAACACATTTGGGCACATGTTTGCAAAGGGGTCTAAAATCGCAGGTACGTGGTAC

CGG

SEQ ID NO: 30

19_STR_101D5_M13F.fa

GGACGACGTACCTGCATGATTGGTTCCACCTAATAAGCAAGGAAAGAATACTTGACCTTCAA

ACTCATCCAGTGTTGGAGATCTCCATAATACCTTCCATCCTTTGGACCATGCCTTGGATGGA

GACAGACACTACTGGAGAAAGGGGCTGCTTACCCCAGAGAGAATACTACCTAAATGCTGCTA

CATCAGAGACTATCCATGACGAGCATCTCATATAAGGAT

SEQ ID NO: 31

20_STR_S.12_5_T7.fa

ATGATTGGTTCCACCTAATAAGCAAGGAAAGAATACTTGACCTTCAAACTCATCCAGTGTTG

GAGATCTCCATAATACCTTCCATCCTTTGGCCCATGCCTTGGATGGAGACAGACACTACTGG

AGAAAGGGGCTGCTTTCCCCAGAGAGAATACTACCTAAATGCTGGTTCATCAGAGAATATCC

ATGAAGAGCATCTCAGATAAGGATTGAAAAGGGGTGCTGGGTAGAGTATAGTAGAGGAGGA

CTTGTTAAGTTCACTGATGCTGGGAAGAAACTTCCTGTAATGCCTACAGCATTCCATGGGCC

ATAGAGTACCAATATGGTATGCCTCTTTACAGAGTCAATCTCAGCCCCCAGAAAGTGTATTC

TACTGTGCTCAGGCCCAAAGGCAGTGTGGTGGTCAAAGGGCAACTGGCCTCCTGAACCCAGT

AGAGCCTTGCAAAGTGC

SEQ ID NO: 32

49_STR_101DS_1_T7.abl.fa

TABLE 8-continued

```
GGTACGACGACCCTGCATGATTGGTTCCACCTAATAAGCAAGGAAAGAATACTTGACCTTCA

AACTCATCCAGTGTTGGAGATCTCCATAATACCTTCCATCCTTTGGCCCATGCCTTGGATGG

AGACAGACACTACTGGAGAAAGGGGCTGCTTTCCCCAGAGAGAATACTACCTAAATGCTGGT

TCATCAGAGAATATCCATGAAGAGCATCTCAGATAAGGATTGAAAAGGGGGTGCTGGGTAGA

GTATAGTAGAGGAGGACTTGTTAAGTTCACTGATGCTGGGAAGAAACTTCCTGTAATGCCTA

CAGCATTCCATGGGCCATAGAGTACCAATATGGTATGCCTCTTTACAGAGTCAATCTCAGCC

CCCAGAAAGTGTATTCTACTGTGCTCAGGCCCAAAGGCAGTGTGGTGGTCAAAGGGCAACTG

GCCTCCTGAACCCAGAAGAGCCTTGCAAAGTGCTGGCAGTCAGGGAGGTGCCATACATGATT

CTTGTCTTT
```

SEQ ID NO: 33

26_STR_41F5_M13R.fa

```
CTTTAATAGCCATGGCCTTATAGACGGTGGCCACGCGGCCTGCACAGGCTGTGTGCATTAGG

CCCTTTAGCCTTGTTTTACACTTGCAGCACCTACTTCTGCTGGGGTTCAACTCAGTGCACAG

CACTTGCTTAGCCTATGTGAGACCCTGCACTTAATGCCCAGCACCACAAAAAAGAAACAAAA

TACCTCTATTTTAAGATGATGCTTAAGAATTATCCTAATTCAAAGCAGCAAAAATATAACTT

TACAATTATAAAAGAGCTAAACCAGAACCCACAATCAGTGTCTAAGTGTGAATCTAATAAAC

ACTGCCTCTCTGCAGCTCTTACCAGCTTTCTGGGTTGTTACACACACTCACACGCGCACA

CACACACACACGCGCTCCCTCCTACTGAGG
```

SEQ ID NO: 34

26_STR_5D12_T7.abl.fa

```
TTTTTTTTTTTTTTTTTTTTGGGGCTTTCGGCGGTTTTTTTTTGGAAGGAAACCCATG

GGGGGGGGTTTGGGGGGGGGGGCCCCCTAAAAAATAACCTGGGGTTCAAAGGGCCCCCAAAC

CTTACTGGAAAGGCCGGGGGACAAAACCATGGTTTCAACCGGACCACTTGTTACCAAGGTGG

GGGCCCCAAGAGGGCTTCAGGGGGGGGGGGGGCCCTTTAAAGAAAGCGGGAACTGGGGGGG

GCAAACCCTGGGCCCACCTTTGACCCCCTTGAAAAAAAAAAAAAAAA
```

SEQ ID NO: 35

30_STR_55C5_M13F.fa

```
CTCCCAGTCTTCTCTTTTCTATAGCATGGCTTTAAAGCCTGCCTCCTTGACATGCTGTATAT

ATTCTATTGTATTTGTTTCATTGTCCCACACTTAACTCAGGTGTGCTAAAAATAAAAGTAAA

TTTTAACAGTCAAAAAAAAAAAAAAAAAAAAAAAAAAAAAAAAAAAAAGGGAAAAAAA

AAAAAAGGGCCCCCCCTTTAAAAGGGTCCCAAATTTTGGGCCCCCTTTTTGAAAAAACTTT

TTTTTAAAACCCCCGGGGGGATTAAATTTTTTTGGGGG
```

SEQ ID NO: 36

32_STR_38D9_T7.fa

```
CATTAGTGGAGAGGTGTGCAGTGGGACTGTGAGTGCAACTACTTTAGTGCAGATGTGTGCAG

TGGGCCTGTGAGTGCAGAATCATTAGTGCAGATGTGTGTAGTGGGCCTGTGAGTGCAGGCAC

ATTAGTGCAGAGGTGTGAAGTGGGCCTGTCAGTGCAGGCACATTAGTGGAGAGGTGTGAAGT

GGGCCTGTGAGTGCAGG
```

SEQ ID NO: 37

38_STR_42C8_T7.fa

TABLE 8-continued

CAAGCTTTTTTTTTTTTTTTTTTTTTTGGTTTTTGGCGGTTTTATTTTTGGCAGGAAAC

CCTGGGGGGGGGTTTGGTGGGGGGGGCCCCCTTAAAAATACCCCGGAGGTCAAGGGGGTTC

AAAACTTTTTTTAAAAGGCTGGG

SEQ ID NO: 38

41_STR_8B9_T7.abl.fa

CCTTTTTCTCCCCCCATGGAAGCGAAGACTCTGAACACAGAGTGGTCTGTATTGTGGGGTTG

GGGGTTGCCTCCCTATCGCTGGGTAGCCTGAAGCGTGAGTCCAGACTAGACGTGTGAGGGGA

ATGATCTATGCCGTGCTCGAATAGCTGGGAGGTCCCTTTGTCCCTGAGACCAGAACGGGAAA

TGGTTATCCGCACTGGGAAGCTGCCTCTCAAGTAGAAACTGCCAGATAACTTTCTGGGCTGG

GAATTCTGTCAACTTAACTGAAGCCTGGCAGCATCCGCCCCAAAGCAATTTAAATTAGGGAG

AGTCCTGGGCTGTCCCAGGTGCCCTTAGGTAAACTTGACAGACTGCTGAG

SEQ ID NO: 39

56_STR_95H10_T7_H07_063.abl.fa

CTCCCAGTCTTCTCTTTTCTATAGCATGGCTTTAAAGCCTGCCTCCTTGACATGCTGTATAT

ATTCTATTGTATTTGTTTCATTGTCCCACACTTAACTCAGGTGTGCTAAAAATAAAAGTAAA

TTTTAACAGTCAAAAAAAAAAAAAAAA

SEQ ID NO: 40

43_STR_95H10_T7_C06_049.abl.fa

CGACGACCCTGCCTCCCAGTCTTCTCTTTTCTATAGCATGGCTTTAAAGCCTGCCTCCTTGA

CATGCTGTATATATTCTATTGTATTTGTTTCATTGTCCCACACTTAACTCAGGTGTGCTAAA

AATAAAAGTAAATTTTAACAGTCAAAAAAAAAAAAAAAA

SEQ ID NO: 41

44_STR_65E3_T7_D06_057.abl.fa

GATGTGTTCCACTTCCCTATTTCTGCTGTAGAGAAACAAGTAAATTTTCTTAGAGAATGAAA

AAAAAAAAAAAAAGG

SEQ ID NO: 42

45_STR_42F8_T7.fa

CCTCAGTAGGAGGGAGCGCGTGTGTGTGTGTGCGCGTGTGTGAGTGTGTGTAACAACCCA

GAAAGCTGGTAAGAGCTGCAGAGAGGCAGTGTTTATTAGATTCACACTTAGACACTGATTGT

GGGTTCTGGTTTAGCTCTTTTATAAGTGTAAAGCTATATTTTTGCTGCTTTGGAATAGGATA

ATTCTTAAGCATCATCTT

SEQ ID NO: 43

55_STR_47E5_T7_G07_055.abl.fa

CCATTTGAGGGAAGATACAGTGTTAGATGAAGCAGAAACCAATTTTATTGTTAGTGTTTAAT

CTTGGTGCAGATTTATAAGTTTTAGAGTAGCCCAGAGACTAAAAGTGAATACTTAGCAAATG

GATAGCCAGTGTTCTATATAGGAATCATTGCTTTTCAGAGGGCTTAAAGTTTAAGTAGAAAA

TATATACTCAAGAAGGCGATAAAAGCTGATGAGAAAGTGAGTTAGCAGAACCCAAAGCCGTG

CTGGGCCGCGGTGACTCATTAGCAGAGGAGGAGGGGAGGGCAGTATATTCCTGGGATACTCT

CTCCAGACCCAGCCTGGCTTCTGACATCATCCACCTGTGCCCTCAAAACCGTCTTAGTCTGT

TABLE 8-continued

TCTGCAACTCTTAAGTGACATACCTAACTCAGCTCATGGCTAAGGAAAAAAAATTAAAGTTG

TCCTGGTGATTAAACTCTGGACCTCCCACATCTAAGTCCCGAGTTGACAAACTGCATCCCCA

GC

SEQ ID NO: 44

78_STR_50B9_T7_F10_090.abl.fa

CTTTAATAGCCATGGCCTTATAGACGGTGGCCACGCGACCTGCACAGGCTGTGTGCATTAGG

CCCTTTAGCCTTGTTTTACACTTGCAGCACCTACTTCTGCTGGAGCTCAACTCAGTGCACAG

CACTTGCTTAGCCTATGAGAGACCCTGCACTTAATGCCCAGCACCACAAAAAAGAAACAAAA

TACCTCTATTTTAAGATGATGCTTAAGAATTATCCTATTACAAAGCAGCAAAAATATAACTT

TACAATTATAAAAGAGCTAAACCAGAACCCACAATCAGTGTCTAAGTGTGAATCTAATAAAC

ACTGCCTCTCTGCAGCTCTTACCAGCTTTCTGGATTGTTACACACACTCACACACGCGCACA

CACACACACGCGCTCCCTCCTACTGAGG

SEQ ID NO: 45

01_STR_42H7_M13F.fa

CCTCAGTAGGAGGGAGCGCGTGTGTGTGTGTGCGCGTGTGTGAGTGTGTGTAACAACCCA

GAAAGCTGGTAAGAGCTGCAGAGAGGCAGTGTTTATTAGATTCACACTTAGACACTGATTGT

GGGTTCTGGTTTAGCTCTTTTATAATTGTAAAGTTATATTTTTGCTGCTTTGTAATAGGATA

ATTCTTAAGCATCATCTTAAAAT

SEQ ID NO: 46

01_STR_42H7_M13R.fa

CTTTAATAGTCATGGCCTTATAGACGGTGGCCACGCGGCCTGCACAGGCTGTGTGCATTAGG

CCCTTTAGCCTTGTTTTACACTTGCAGCACCTACTTCTGCTGGGGTTCAACTCAGTGCACAG

CACTTGCTTAGCCTATGTGAGACCCTGCACTTAATGCCCAGCACCACAAAAAAGAAACAAAA

TACCTCTATTTTAAGATGATGCTTAAAGAATTATCCTATTACAAAGCAGCAAAAATATAACT

TTACAATTATAAAAGAGCTAAACCAGAACCCACAATCAGTGTCTAAGTGTGAATCTAATAAA

CACTGCCTCTCTGCAGCTCTTACCAGCTNTCTGNGTTGTTACACACACTCACACACGCGCAC

ACACACACACGCGCTCCCTCCTACTGAGG

SEQ ID NO: 47

10_STR_46B6_M13F.fa

CCTCAGTAGGAGGGAGCGCGTGTGTGTGTGTGCGCGTGTGTGAGTGTGTGTAACAACCCA

GAAAGCTGGTAAGAGCTGCAGAGAGGCAGTGTTTATTAGATTCACACTTAGACACTGATTGT

GGGTTCTGGTTTAGCTCTTTTATAATTCTAAAGTTATATTTTTGCTGCTTTGTAATAGGATA

ATTCTTAAGCATCATCTTAAAATAGAGGGTATTTTGTTTCTTTTTTGTGGTGCTGGGCATTA

AGTGCAGGGTCTCACATAGGCTAAGCAAGTGCTGTGCACTGAGTTGAACCCCAGCAGAAGTA

GGTGCTGCAAGTGTAAAACAAGGCTAAAGGGCTAATGCACACTAGCTGTGCAGGCCGCGTGG

TCATCGTCTATAANGCCATGGCTAATAAAGTT

SEQ ID NO: 48

10_STR_48B6_M13R.fa

CTTTAATAGCCATGGCCTTATAGACGGTGGCCACGCGGCCTGCACAGGCTGTGTGCATTAGG

CCCTTTAGCCTTGTTTTACACTTGCAGCACCTACTTCTGCTGGGGTTCAACTCAGTGCACAG

TABLE 8-continued

CACTTGCTTAGCCTATGTGAGACCCTGCACTTAATGCCCAGCACCACAAAAAAGAAACAAAA

TACCTCTATTTTAAGATGATGCTTAAAGATTAATCCTATTACAAAGCAGCAAAAATATAACT

TTACAATTATAAAAGAGCTAAACCAGAACCCACAATCAGTGTCTAAGTGTGAATCTAATAAA

CACTGCCTCTCTGCAGCTCTTACCAGCTTTCTGGGTTGTTACACACACTCACACACGCGCAC

ACACACACACGCGCTCCCTCCTACTGAGG

SEQ ID NO: 49

25_STR_5D2_T7.abl.fa

CTGGCACCTCATTGCCAAGACTGTCCATTCCAATATTTAGTTCGCCAAGCTTTTGAATAGAC

CTATTAAGGAATTGCTCAGTAAGATTCTGCTGCTGATCAGGACCGTCCTCTTGGTTCACACC

TCCTTCAAGTAACATCTGCTGGTATATCTGCCGCTGTTGCTCCTTCTGTTCGAGATGCTGCT

GATAGCGCAATCTTTGCCTATAATATTCTTGAAATTGTTCAGTAGAATCTCGAAGCTCGTTT

TTTTCTTGTTGTTTAGCTGGAACTGGGTTCTGTGCTCCATTTGCAGGCTCTTTCTCTAACCC

CGAACCCTGGCACATGGGTTCAATGCTCACAGGCTGCTGGGTCTCAACAGGGGTATCACTTC

GCTCAGGAGATTCTTCATAGATACTATGACACTCTGTATTCTCAAGCAGAAGACTTCTGCT

SEQ ID NO: 50

13_STR_32D4_1_T7.abl.fa

CGAGGACCAGCACAGCAGTGAGGAGGAGGAAGAAGAGGAAGAGGAGGAGGAGAGTGAAGACG

GGGAGGAGGAGGAGGACATCACCAGTGCCGAGTCAGAGAGCAGTGAGGAGGAGGAAGGCGGC

CCCGGGGACGGCCAGAACACCACCCGGCAGCAGCAGCTAGAATGGGACTACTCCACACTCAG

CTACTAAACACGCGCTCGCCCAGCACCTGCTCTCCAGACTCTCCCAGCCATCTTCCAGCCCC

ACGGGTCCACGATG

SEQ ID NO: 51

90_STR_32D4_M13F_B12_096.abl.fa

CGAGGACCAGCACAGCAGTGAGGAGGAGGAAGAAGAGGAAGAGGAGGAGGAGAGTGAAGACG

GGGAGGAGGAGGAGGACATCACCAGTGCCGAGTCAGAGAGCAGTGAGGAGGAGGAAGGCGGC

CCCGGGGACGGCCAGAACACCACCCGGCAGCAGCAGCTAGAATGGGACTACTCCACACTCAG

CTACTAAACACGCGCTCGCCCAGCACCTGCTCTCCAGACTCTCCCAGCCATCTTCCAGCCCC

ACGGGTCCACGATG

SEQ ID NO: 52

B2_STR_50E5_T7_B11_092.abl.fa

CTTCTTGATGATGCGTAACATGTTCTGGTAGGAGTTCCAAGTGTTGTGAGCCACCAGGAGAT

CATGGCTGCCGGGCAGCAGCTTGATGAGGGCAGAGCACGAACCGGAGCCCACGGAAGGCTTG

GTGTTGGTCTTATTCAGGGCTGGCTCTAGGTCTTCCAGATCTCCAGAGATCTGCAGCAGGAG

GAACCCCAAGGGTTTGATGTTGAACCTCCCAGTTGGGAAGGTTAAACGGCCTTCATAGCTGT

CCTCCAGGCCTTTCAGCTGCAAGAGGGTCAGCCGCACCTGGTGCCAGTATGGCGAGTCCGGG

CTAAGCTCCATTTCCCTCTGCATCCACTCCAGGTTGGCCTCCAGGAAGCTCTTGAGCTTCTC

ACAGTAGCCGACTTCG

SEQ ID NO: 53

74_STR_76C2_1_T7.abl.fa

TABLE 8-continued

CGACGACCCTGCCTCCCAGTCTTCTCTTTTCTATAGCATGGCTTTAAAGCCTGCCTCCTTGA

CATGCTGTATATATTCTATTGTATTTGTTTCATTGTCCCACACTTAACTCAGGTGTGCTAAA

AATAAAAGTAAATTTTAACAGTCAAAAAAAAAAAAAAAAG

SEQ ID NO: 54

14_STR_39E12_M13F.fa

GCGGCCGCCCGGGCAGGTCGCTCCGCGTGTTTGGTGGGGTTACTTTTCCCACTTCGCGACGT

TTGCCCTGGGCAGCTCAGAAGTGTTACGTGTTGCACCCTCCCCAAGGCTGTCAACAGCAGAA

AGCAACCCCTGGCGCTAGCCCGTATT

SEQ ID NO: 55

12_STR_S.60_6_T7.fa

CATGAAAATAACGGAGCCTCGAAAGCTATAACAGACCTTTTGTACATAGAGAAATGGCATAT

TTATTAAATAAGTTGGATTTGTAAAAAAAAAAAAAAA

SEQ ID NO: 56

31_STR_59E12_M13F.fa

GGAGGCGGAGGATGAGTGCCAACACCCTCGACTGCCTGCTCTAGGCGATGAGGTTATAGAAA

GGGAAGAGTTTCAGGATATGGCTGTGTGTAGGGGCATGAAGGCAGGTTATAAACAAATA

TATCCCAGCTGCCTAAGGAGTTGGTTGCTGTCCTCACTCTTAACAATCCAGTGGGATCTAGT

GATCAACATCAGTTTGGAGACTCTAATCTTCATGCTCATGTATTCATCCTGACATTTTAACT

TGCTATTCTGTGTGACCGAATACTTGTTATACCTAGAATACGACCTAAGTGCCTTCTGATTT

CTCATGATTTCTTTTCAAACAGGGTCTAAGTCATCTACTTGCATTTT

SEQ ID NO: 57

34_STR_59E12_1_T7.abl.fa

GGAGGCGGAGGATGAGTGCCAACACCCTCGACTGCCTGCTCTAGGCGATGAGGTTATAGAAA

GGGAAGAGTTTCAGGATATGGCTGTGTGTAGGGGCATGAAGGCAGGTTATAAACAAATA

TATCCCAGCTGCCTAAGGAGTTGGTTGCTGTCCTCACTCTTAACAATCCAGTGGGATCTAGT

GATCAACATCAGTTTGGAGACTCTAATCTTCATGCTCATGTATTCATCCTGACATTTTAACT

TGCTATTCTGTGTGACCGAATACTTGTTATACCTAGAATACGACCTAAGTGCCTTCTGATTT

CTCATGATTTCTTTTCAAACAGGGTCTAAGTCATCTACTTGCATTTTGCCAGAAGCTCTCCG

GAAAACAAAGCATACAAAATCTACTTGCTATTTCTCT

SEQ ID NO: 58

45_STR_8G3_T7.abl.fa

CAAGGCTACAGGCCTAGGCCTAGGGATACAACAGCGAAGGAACCACTCTGGTCTCAGCCCAA

GCAGCACAGCTGGAGCGCAGCTCTCTTCTCGCTTTCATCTTTACGGAGACTTGGGTGGAAGG

GCGGGCCCTTTGACATCTTTGTCGTCGGCCTTGGACTCAGAGATGGCCAGCTTATTCTGCAG

GGAGCACAGCAGCTGGAGGTAGCTCTGGTTCCTCTGCAGCTTCTCCTGCTCCTGTCCTGCTT

GCTGCTTCAAGGTTTCAAGTTCCTGGTGAGAACCATCAAGCTTCTCCAGAGCTCTCTTCCGG

CGTCTCTTGACCTCAGCAGAAATCTTTGTCAGATTCTGCAAACGCTTCTGCTGCAGCACCCA

CTGCTTCTGAGCTAACTGCAGTTTCTCCTCAAGGACTCGCTTCTTAGCCTCAAGTTGCTCAA

AAGCCTTCTGAAGCTCGGCG

SEQ ID NO: 59

TABLE 8-continued

54_STR_1SG9_T7_FOS_046.abl.fa

TTTTTTTTTTTTTTTTTTTTTTCCCTTTGGGAGGTTTTTTTCAAAAACCCCGGAAAAATTG
GCCCTGGTTCCGGGGGGTTTTTGAAAAAATAAAAACGGGAACTAACCGGGGGGGGGGAAA

SEQ ID NO: 60

95_STR_102A2_T7.abl.fa

TTTTTTTTTTTTTTTTTTTTTTTCCTTTGGGAGGTTATTTTCAAAAAGCCCGGAAAAATTG
GCCCTGGTTTCGGGGGTTTTTGAAAAACCAAAAACGGGAACCAACCGGGGGGGGGGAAA

SEQ ID NO: 61

24_STR_S.35_6_T7.fa

GGAGAGAATGGAGGAGGCGGTCATGTCAATTCTGCACAACTTAGAGATGAAGAACACTGAGA
TCCATGAGAACAACCGTAAGGTGAAGAAGGAGATTACCTTCTCTAGAAACCTGCTCAGCCAG
CTCCTGATGGAGAACACATGTAGGAAGAAGTTGCTCCCACTGAAGCAGGAGAGCAAGGAGGG
ACATCTTGAGTGTGCAATGAACCAGAAATATTTGGTTGACTTCAACAAGAAAGATAAAGACC
AGCAACCTCCAGACCCAGCATCATCAGGTCTCAGAAAGTGCAAGAGAGCTGGAATTGGACAC
ACAGCAGTAAGAGAGCTTCCTGAAGAATAAGTTGCTTTCTCACGAGTCCCTGATGACAAACA
TCCTGAACGAAAACATCACTTGAGAGACAACTTGGGGACCGCCTTTCATTATGTGTGCTAG
AGGAGAAACAGCAATACATCTGTGCTTCTAAATGTTCGTTAAGAATATGCTGTTTAGAAATA
TTTTTGTTATGATTNTAAATGAGGTNTCTTTTTGTGGTTCATATTTATATGGTCTTGGTACT
ATNTTTACTTTCANATATTTTTAAATATTTNTATTCATTCATTNTAAATCCTGTTGGTGGAA
AATGATTCAATATGAATAAATATGTGTTTATTCTTGAAAAAAAAANAAAAA

SEQ ID NO: 62

20_STR_77E1_T7_D03_029.abl.fa

GAGGAGGCGGTCATGTCAATTCTGCACAACTTAGAGATGGAGAACACTGAGGTCCATGAGAA
CAACCATAATCTGAAGAAGGAGATACCTTCTCTAGAAACCTGCTCAGCCAGCTCCTGATGGA
GAACACATQTAGGAAGAAGTTGGTCCCACTGAAGCAGGAGAGCAAGGAGGTACATCTTGATT
GTGCACTGAACCAGAAATATTTGGTTGACTTCAACAAGAAAGATAAAGACCATCAACGGCCA
GAACCAGCATTATCAGGTCTCAGAAAGTGCAAGAGAGCTGGAATTGGACACACAGCAGTAAG
AGAGCTTCCTGAAGAATAAGTTGCTTTCTCAGGAGTCCCTGATGACCAACATCCTGAATGAA
AACAGCACTTGAGAGACAACTTGGGGACCGCCTTTCATTATGTGTGCTAGAGGAGAAACAG
CAATACGTCTGTGCTTCTAAATGTTCGTTAAGAATATGCTTTTAGAAATATTTTTGTTATGA
TTTATTTGAAGTTTTCTTTTTGGTGGTTCATATTTATATGTTCTTGTTACTATTTTTACTTT
TCAATATTTTTAATATTTTTATTCATTTAATCCTGTTTTGTTGGAAAAATGTATTTGTTATG
AATAAAAATTGAATTCTAAAAAAAAAAAAAAA

SEQ TD NO: 63

85_STR_77E1_T7_E11_0B6.abl.fa

GGAGAGAATGGAGGAGGCGGTCATGTCAATTCTGCACAACTTAGAGATGGAGAACACTGAGG
TCCATGAGAACAACCATAATCTGAAGAAGGAGATTACCTTCTCTAGAAACCTGCTCAGCCAG
CTCCTGATGGAGAACACATGTAGGAAGAAGTTGGTCCCACTGAAGCAGGAGAGCAAGGAGGT
ACATCTTGATTGTGCACTGAACCAGAAATATTTGGTTGACTTCAACAAGAAAGATAAAGACC

TABLE 8-continued

ATCAACGGCCAGAACCAGCATTATCAGGTCTCAGAAAGTGCAAGAGAGCTGGAATTGGACAC

ACAGCAGTAAGAGAGCTTCCTGAAGAATAAGTTGCTTTCTCAGGAGTCCCTGATGACCAACA

TCCTGAATGAAAACAGCACTTGAGAGACAACTTGGGGGACCGCCTTTCATTATGTGTGCTAG

AGGAGAAACAGCAATACGTCTGTGCTTCTAAATGTTCGTTAAGAATATGCTTTTAGAAATAT

TTTTGTTATGATTTATTTGAAGTTTTCTTTTTGGTGGTTCATATTTATATGTTCTTGGTACT

ATNTTTACTTTCAAATATTTTAAATATTTTATTCATNTAATCCTGNTTTGGTGGANAAATGT

ATTTTGTATGAATAAAATGGATTCTAAAAAAAAAAAAAAAA

SEQ ID NO: 64

92_STR_15C5_T7.abl.fa

TGTTTTTTTTTTTTTTTTTCTTGCTATAGAGACTTGACTCTTTGCTCAACACCATGCCCC

ACGTTTGGGAGAGGAAGATGGCAAAGACTGAAAGCACGATGCCGGGGTATATTGCAACACC

ATCAAAACAGAGCCCATAGCTGCCTGCCCCCCGGTATAGTTAGAGACAGGCCGTGTGTTACC

TCTACAATTAAAACGTACTTGTAGACTTGGNGGTAAGGGACCCTCCACCTATTTCAAATTCT

GCCAGAAGACAGAAGGATGTTCACTCACCAATCAAGAACCCTTGGCTTCCTACTCCTGACTT

TGTCGCTGGANTGCTGGCTACAGTACCAAACCTATGTAGAACTATCATCTTCAGTCGAGCCT

CGGTGTAATTGGCAGAGATTCTGAGTCAACTACCATGCAGAGATCTCCGACCCTGTCTAGAG

ACATTTACTAGAAGCTGTCTTACAGCCCTGTCTTTGAGGCGAGACACATACCAAATGTATGT

TCCCCCAAGAGGAGACACACTCTATCTTCAGATATCTGTGAACCCANNNNNNAAAAAAAAAA

CCAGCCCGCCCCGGGGGCGCACCTTGAATGACACAGGGGACATGGNTGGCTGCCCCGTATA

GAAAGCCCCAGCTTNAACACAGNAAATGTG

SEQ ID NO: 65

68_STR_11D5_T7.abl.fa

CAGAAGCAGTTAGAAGTCATCAATGCTATTGTGGACCCCAGCATGAACCCCGACCTACTGAT

GGGAAACAGGGCTCCTGCAGGGTCCGTTCAGCCAGGACTTGGGAAAGCCCGGCCAGCAGCTC

AGAGCTCAGCTTCTCCTGCCTCGGTGGACACCTTGCTGCCAGCCATGCCTCTCAGGAGCTTC

CCACAACGGGCAAACTGCGGGCCCCCCGGCCTCCCGGAGCCTGCCTTCCTTCCTGATGCTGA

GAGGTTTCTGATCTAAGCTGTGAGGCGGGCAAGGCCAGCCTTCTTGTGCGCGTGTGTCCTGT

GCATCACCCATCCCATGGCCCACCTGCCTGGCTCAGGCAGTTCTGTGAAAACCCCACATGTG

CCATAACCCATGGACGGGTGCCTCCCATTCCCAGGCCTCTCCTCAGCCAGCACCCGAACCAC

TTCATCCAGCTCATGGCTACCCCATCCCCACAGACCTCCTAGCCCAGCCC

SEQ ID NO: 66

10_STR_71H11_M13R.fa

TTTTTTTTTTTTTTTTTTTCCAAAAAAACAGTAAAATTTAATTTCTAAAGAGGGTTAAAAT

TTTCCTTTCCCCCCAAAATTAGGGAGATTCCAGTGTTAAAAATGTCCTCAAAATTTTTAT

GACCCTAA

SEQ ID NO: 67

35_STR_71H11_M13F.fa

GAGACCAAGAAGCCTGGCATGAACTTGCAGAACTTTATATCAATGAGCATGACTATGCCAAA

GCAGCCTTATGCTTAGAGGAGCTGATGATGACAAATCCACATAACCACTTGTACTGTCAACA

GGACGCAGAGGTCAAATACACCCAAGGTGGACTTGAAAACCTGGTGCT

TABLE 8-continued

SEQ ID NO: 68

33_STR_60H2_T7_A05_036.abl.fa

AGGTTGATTCCTAGCAGCCACATGGAGCCAAATTGTCTGTAACTCTAGTTCCAGGGTCTCCA
ACATCTACCCTTGACCATGGCTGGCACTGTGTGTATGTGGTGCACAAACACACGAAGGCAGA
ACACCTAAAAGGGGTATATGTGCTATCATTTAAGTGTCTCTTAAATGAAAAGCCTTCAACCA
GGATTTCATCATTAGAAATAGAATTGATGTCCACCCTGTGTCATGGGAACTGAGAGGAAGGG
CAGTATAAATCTGAGAGGTTCCTTTGTGTGGTGGACCCCGAAGAAGAAAGCCCCATGGCTGA
ACAGCTGTTGTCTCCTCCTACCCCACAGCTTTCCCTAATAAAGGGATTGTTATTTTGAAAAA
AAAAAAAAAA

SEQ ID NO: 69

16_STR_8H4_M13F.fa

CTTCTCTAACATGTCGGTGGGCGTCACATCAGTGTTGACCTACTCTTCCGTCT

SEQ ID NO: 70

29_STR_8H4_M13R.fa

CAGGAGGCCCCAAGAGCTGCAGGCTAGTGGGTCCAGGCTAAGGACTTGGGAAGTGGGGTTCA
GCTCAGGCTTGGCTGCAGATGTTAGATGCAGAGACTTCTGACCTGTCTAACAATTAGACCTG
TTACTGCCAGTGTAGGGACAGATGGTTTCTTTGACTTCAAGAAGCCCATTAGTGGAAAGACA
TCTGACTTGGTATGTTACTAAGACAGCAATAACCCTGTAG

SEQ ID NO: 71

06_STR_54A11_T7_F01_014.abl.fa

TGGAGCTAATTGCGCGCGGCCGCGGTACGACGAACCTGCGCCTATTAGAATGAGTGGAATGC
CTCCATCCCTCAATCGTCTGAAGTGATCTGTTAGCTAAGAGCATGGCTCCCAGGGGCCCGTC
CTCAGCCACTTGTACTCCTGGGCTAGCCTTGTCATAAGATGCCACCTdGACACTGATGGAGT
ATTGGAGCAGCAGGCCTGGCTCCTGACCTAAACTGACAGCTCAGACTCTGCAGGAGTCTGCT
GGAAATCCAACATCTTACTCAACAACTGCCGGCCAGATGGGCGTGGGCGAGGGTGGGCCAAG
ACAGGGTGCCTTATACTTTGTTCTAGCACATTCCAAGGTATTTCAGGGCGTCAGCACCTGGA
ATCCCATATGTCAAAGCCAGTATTAAAGCAAGTTTATGCATTCCTCGAAAAAAAAAAAAAAA

SEQ ID NO: 72

55_STR_102F3_1_T7.abl.fa

AGCTAATTGCGCGCGGCCGCGGTACGACGAACCTGCACCTCTGTCTTCTGCCCCCCTCCCTT
GGACACATTCACACCTACCTCTAGGAGAGATTGGGGATACCTTTAGCTCTCTGACCGAGGAC
CAAGCCTCTGACTCAGACCTGTATATGGCACCAAGTTACAACCCTTTCCAAAAGGCTCTTCC
CAGGGGAOCACTTGGCATTTTCTGGCAGACCCCATTATCCCTTTCCCAATGCCCTCTCTCTG
ACTTTGAGCATCAGGCCAGACTGCCTGAGATCTGGTGCCTGCCACAGTGCCTGGCCAGGGGT
GAGGCTTTGGTTACCTTCTGTTGTATTTGTGTGGATAGATGGGCAGCTAACAATTGTAACAG
GTCCTAGGGTCAGATGTGGATGGTCTCATACAGTGGCTTCTAATGGAGAATGTATCTGAACC
CATATCAAATCACCTCACTGTATTTTTCTCTTCCCTAACCTGTTAACTAGCCATTGTTGTAG
GGGGCTTTTGCACAGTGCCTCACTGTCTCACATGCTAAGTAAAGGAACTCCTGCTTTCAAAA
AAAAAAAAAA

TABLE 8-continued

SEQ ID NO: 73

21_STR_S.54_5_T7.fa

ACCTCTGTCTTCTGCCCCCCTCCCTTGGACACATTCACACCTACCTCTAGGAGAGATTGGGG
ATACCTTTAGCTCTCTGACCGAGGACCAAGCCTCTGACTCAGACCTGTATATGGCACCAAGT
TACAACCCTTTCCAAAAGGCTCTTCCCAGGGGAGCACTTGGCATTTTCTGGCAGACCCCATT
ATCCCTTTCCCAATGCCCTCTCTCTGACTTTGAGCATCAGGCCAGACTGCCTGAGATCTGGT
GCCTGCCACAGTGCCTGGCCAGGGGTGAGGCTTTGGTTACCTTCTGTTGTATTTGTGTGGAT
AGATGGGCAGCTAACAATTGTAACAGGTCCTAGGGTCAGATGTGGATGGTCTCATACAGTGG
CTTCTAATGGAGAATGTATCTGAACCCATATCAAATCACCTCACTGTATTTTTCTCTTCCCT
AACCTGTTAACTAGCCATTGTTGTAGGGGCTTTTGCACAGTGCCTCACTGTCTCACATGCT
AAGTAAAGGAACTCCTGCTTTCAAAAAAAAAAAAAAAAAGGGCCCCCCTTTAAACGG

SEQ ID NO: 74

19_STR_21A8_T7.abl.fa

TTTTTTTTTTTTTTTTTTTTTTTTTCATGGGAAAAAAAAAAGGGTTTAAAAAATGGCTTG
AAACCCGGGGGGGGGGGCCAAAACCCTCCTTTTTTAATAAACCTTTACCGAAGAAGGGTTT
TCAAAAGGGGGGGGGGGGGGGGCCCCCCTCCCGCCCTTTTAGGTTTGGGGGGGGGGGGA
AA

SEQ ID NO: 75

22_STR_21H9_T7.abl.fa

TTTTTTTTTTTTTTTTTTTTTTCGAAAAAAAAAAAAAAGGGGTAAAAAGGGGTTGAAACC
CAGGGGGGGGGGGCCAAAACCCTCCTTTTTTAATAAACCTTTACCGAAGAAGGGTCCTCCAA
AGGGGGGGGGGGGGGGGGCCCCCCACCCGCCCTTTCAGGGTTGGGGGGGGGGGGGAA

SEQ ID NO: 76

24_STR_31G6_T7

CGAATACAGACCGTGAAAGCGGGGCCTCACGATCCTTCTGACCTTTTGGGTTTTAAGCAGGA
GGTGTCAGAAAAGTTACCACAGGGATAACTGGCTTGTGGCGGCCAAGCGTTCATAGCGACGT
CGCTTTTTGATCCTTCGATGTCGGCTCTTCCTATCATTGTGAAGCAGAATTCACCAAGCGTT
GGATTGTTCACCCACTAATAGGGAACGTGAGCTGGGATTAGACCGTCGTGAGACAGGTTAGT
TTTACCCTACTGATGATGTGTTGTTGCCATGGTAATCCTAGTCAG

SEQ ID NO: 77

65_STR_31G6_T7.abl.fa

CGAATACAGACCGTGAAAGCGGGGCCTCACGATCCTTCTGACCTTTTGGGTTTTAAGGCCAG
GAGGTGTCAGAAAAGTTACCACAGGGATAACTGGCTTGTGGCGGCCAAGCGTTCATAGCGAC
GTCGCTTTTTGATCCTTCGATGTCGGCTCTTCCTATCATTGTGAAGCAGAATTCACCAAGCG
TTGGATTGTTCACCCACTAATAGGGAACGTGAGCTGGGATTAGACCGTCGTGAGACAGGTTA
GTTTTACCCTACTGATGATGTGTTGTTGCCATGGTAATCCTGCTCAG

SEQ ID NO: 78

69_STR_11E11_T7.abl.fa

CTGCAGATATCGGGACTACCGGGACCCGCCGCATTCTTTGGCTCCCTATGGCTACACACTGC
AGTTCTGGCATGTCCTCGCAGCTCGGCTGGCTTTCATCATTGTGTTTGAGCACCTCGTGTTT

TABLE 8-continued

TGTATAAAGCACCTCATTTCCTATCTGATACCAGACCTCCCGAAAGATCTAAGGGACCGGAT
GAGGAGAGAGAAG

SEQ TD NO: 79

09_STR_40E1_T7.fa

CTTTAATAGCCATGGCCTTATAGACGGTGGCCACGCGGCCTGCACAGGCTGTGTGCATTAGG
CCCTTTAGCCTTGTTTTACACTTGCAGCACCTACTTCTGCTGGGGTTCAACTCAGTGCACAG
CACTTGCTTAGCCTATGTGAGACCCTGCACTTAATGCCCAGCACCACATAAAAGAAACAAAA
TACCTCTATTTTAAGATGATGCTTAAGAATTATCCTATTACAAAGCAGCAGCAGATATAACT
TTACAATTATAAAAGAGCTAAACCAGAACCCACAATCAGTGTCTAAGTGCGAATCTAATAAA
CACTGCCTCTCTGCAGCTCTTACCAGCTTTCTGNNGTGGTACACACACTCACACACGCGCAC
ACACACACACGCGCTCCCTCCTACTGTGNG

SEQ ID NO: 80

16_STR_41A8_T7.fa

CTTTAATAGCCATGGCCTTATAGACGGTGGCCACGCGGCCTGCACAGGCTGTGTGCATTAGG
CCCTTTAGCCTTGTTTTACACTTGCAGCACCTACTTCTGCTGGGGTTCAACTCAGTGCACAG
CACTTGCTTAGCCTATGTGAGACCCTGCACTTAATGCCCAGCACCACAAAAAAGAAACAAAA
TACCTCTATTTTAAGATGATGCTTAAGAATTATCCTATTACAAAGCAGCAAAAATATAACTT
TACAATTATAAAAGAGCTAAACCAGAACCCACAATCAGTGTCTAAGTGTGAATCTAATAAAC
ACTGCCTCTCTGCAGCTCTTACCAGCTTTCTGGGTTGGTACACACACTCACACACGCGCACA
CACACACACGCGCTCCCTTCTACTGAGG

SEQ ID NO: 81

24_STR_41D5_T7.fa

CTTTAATAGCCATGGCCTTATAGACGGTGGCCACGCGGCCTGCACAGGCTGTGTGCATTAGG
CCCTTTAGCCTTGTTTTACACTTGCAGCACCTACTTCTGCTGGGGTTCAACTCAGTGCACAG
CACTTGCTTAGCCTATGTGAGACCCTGCACTTAATGCCCAGCACCACAAAAAAGAAACAAAA
TACCTCTATTTTAAGATGATGCTTAAGAATTATCCTATTACAAAGCAGCAAAAATAATAACT
TTACAATTATAAAAGAGCTAAACCAGAACCCACAATCAGTGTCTAAGTGTGAATCTAATAAA
CACTGCCTCTCTGCAGCTCTTACCAGCTTTCTGGGTTGGTACACACACTCACACACGCGCAC
ACACACACACGCGCTCCCTCCTACTGAGG

SEQ ID NO: 82

72_STR_75D9_T7_1409_079.abl.fa

ATGCAGGATCATGTGTGTGTACAACGAATGCCTTTTCCTTCATGCAGCACTTGGACGGGGGT
TTGGTTGGCGTTTTGCATTATCACACAATTGGAGCTCCTTACTGTGTGAGCCAGCCTTCTCG
ACGCCCGGTGATTTTTTTTAAAAGATGTCATGTCTGACTCAATACAATAATGTCATCTTAA
ATTTTGGCCCCTTATTTGAATACTATAGCTACAATCAAAATAATTTGTTAAATTGCTTATAT
TAAGAGTAAACATGGATATGACATTGGTTGTCCACCTGCAAACTTTAGAACAATTTACTGTA
GCTTGATGCTTAGCCAATTTTAAGTGAGGAATTCAACAT

SEQ ID NO: 83

64_STR_31G3_T7.abl.fa

TABLE 8-continued

TTCCTCCTCCTCACTGCTCTCTGACTCGGCACTGAGGATGTCCTCCTCCTCCTCCCCGGCTT

CACTCTCCTCCTACTCTTCCTCTTCTTCCTCCTCCTCACTGCTGTGCTGACCCTCG

SEQ ID NO: 84

52_STR_98F5_T7_D07_061.abl.fa

TTGGAGCTAATTGCGCGCGGCCGCGGTACGACGACCCTGGCACAGAGCCCATGGCGCCAGGA

CAGCAGGCTAGCCTTGGGACCTTTTTGTGGAGTAGTTTGCAGTGAGGTAACGGTGCAATAAA

GTACAGCAAGCGTGAAAAAAAAAAAAAAAGG

SEQ ID NO: 85

07_STR_84C12_T7_G01_007.abl.fa

GAGCTAATTGCGCGCGGCCGCGGTACCACGAACCTGCAGCTCTGTCTTCTACATTACATTTA

TGGCTCCTTAAACTGATTGCCTAACCAACCAAGGGCAATTCCCATCCATCCATCACATGGGT

TGTGGGAAGGATGCAGCCATGGTGTGCAGCTTCCTTCATGAAGGATTATCTGGCCATGGTAC

CTGACTGCTTCACAACTTGCTGTCACTCTGGGTGAGATAATGTGTCTTTAAAAACAGTCCCT

GTGGCAGGTCACTGGGATATAATGTACAACATTCTTAGCCATCATTTCTTTTCTTTTTTTT

CTTTTTTTTGGTTTGCCCTGAGAGACTCCCAGTGGTTTCTACTGAGGGCTAAAGGGACGAGC

TGTTCCCTCATTGAGCAAGACCGTTCGCTGTTCATGATGTGTTTTATGATGGCTTCTTTGGG

AGTTGCTTCTTCAACAGTCTCAACTGTGCTGNGGGATCTCCTGATGCTGACTTTTGACCTTC

GTTTTATTAAAACTAATTAGTGAAAAAAAAAAAAAAA

SEQ ID NO: 86

43_STR_65B9_T7_C06_049.abl.fa

GGTACGACGACCCTGCGATCTGAGACCCACTTTGCAGACATGTGCACAGATGTGTTCCATTT

CCCTATTTCTGCTGTAGAGAAACAAGTAAATTTTCTTAGAGAATGAAAAAAAAAAAAAAAA

SEQ ID NO: 87

46_STR_12B5_T7_F04_042.abl.fa

AATCTTTGGACGAGAGCGTGCCATCATGCTGTTGGAAGGCCAGAAAGTGGTCCCCCGGAGGA

CACTGGCCACGGGCTACCAGTATTCCTTCCCAGAGTTAGGAGCTGCCTTAAAGGATGTTGTA

ACCTAAGTAGAGAAGGGAGCCCCAAGGCAGGAGGTGGGGCCTGTTCCTGCATTCTGAGAAGT

GAGTCAGGTGATTGCTGTGCTTGACTGAGATCAGAAGCCATCTGGCTCTTAGACTCTCTCTC

TCTCCCCTTTCTTCCCATGTTCTGTTGATCCACCTCTCTCCAAGAAACTCCAGTCTCAAGGA

TCTAATCTCATTCTAACCTTAACCTCCTCAACTTCTT

SEQ ID NO: 88

73_STR_12B5_T7.ab1.fa

AATCTTTGGACGAGAGCGTGCCATCATGCTGTTGGAAGGCCAGAAAGTGGTCCCCCGGAGGA

CACTGGCCACGGGCTACCAGTATTCCTTCCCAGAGTTAGGAGCTGCCTTAAAGGATGTTGTA

ACCTAAGTAGAGAAGGGAGCCCCAAGGCAGGAGGTGGGGCCTGTTCCTGCATTCTGAGAAGT

GAGTCAGGTGATTGCTGTGCTTGACTGAGATCAGAAGCCATCTGGCTCTTAGACTCTCTCTC

TCTCCCCTTTCTTCCCATGTTCTGTTGATCCACCTCTCTCCAAGAAACTCCAGTCTCAAGGA

TCTAATCTCATTCTAACCTTAACCTCCTCAACTTCTTGTGGCTTCTGTGTCACATTGTTGCC

CTGGTTCTCCTACATGCTATGTAGACAAAGTTCTACAGTTGTGGCAATAAAGGTAGACTGTG

TCTG

TABLE 8-continued

SEQ ID NO: 89

08_STR_86B5_T7_H01_015.abl.fa

TGGAGCTAATTGCGCGCGGCCGCGGTACGACGAACCTGCGACGTGAGACCGTTTTAATAAAA

GTGCCACCTTACAAAAAAAAAAAAAAAA

SEQ ID NO: 90

43_STR_80G8_1_M13F.fa

CTCGTAGAGGCACAGCGAATATGCGAAATTGCACTCTCGCAAACAAGACTCCGTCAACATAC

CTAAGACATAGAGACGCCCGGGGGAGCTAGGTCAAAAGGCATGGAACCAGCGGTCGCCG

SEQ ID NO: 91

31_STR_77A12_T7.fa

GGTCGACGGTAGCCGCGGCAGCCGAACACGCACAGAGCTGCGCTTTCCCCAAAGCGAAGGGT

AGGAAATGGAAAGGGCCTTGCGGCCGGGAATGGCTGAGCTAGGCTCCTGCAGCTACCAACTC

CAGGCAGTTTAAAGCACCTTTCTTGCACGCCCCGACCTCGTGAGTGGAGTCTAGCTGGAGAA

ACAAAGGCTCTTCTTTGTAGAAAGAACTCTCCCACAAAGAGAGAAAAATTCTCTCAAGAGAA

GCTGTGACTTGCCCTTGGGTCACACGTGGCAAACTCTCCCGTGAACCCGAGACCCAGAGCCA

AGGCCTTTATCTCCGTAACAGTTATCCCTGTAAAGAATTCTCTTGTGAGTCCTTTACAGTTA

CTCTGGCATCTCATATGTATGCGTATATGCATCAGATGAACTGGTTTCCATCCCTTTGATGT

TCTATAAATAGACTCTATCACGGANNAAAAAAAAA

SEQ ID NO: 92

81_STR_77A12_T7_A11_084.abl.fa

AGGGTAGGAAATGGAAAGGGCCTTGCGGCCGGGAATGGCTGAGCTAGGCTCCTGCAGCTCCC

AACTCCAGGCAGTTTAAAGCACCTTTCTTGCACGCCCCGACCTCGTGAGTGGAGTCTAGCTG

AAGAAACAAAGGCTCTTCTTTGTAGAAAGAACTCTCCCACAAAGAGAGAAAAATTCTCTCAA

GAGAAGCTGTGACTTGCCCTTGGGTCACACGTGGCAAACTCTCCCGTGAACCCGAGACCCAG

AGCCAAGGCCTTTATTCCCGGATAACAGTTATCCCTGTAAAGAATTCTCTTGTGAGTCCTTT

ACAGTTACTCTGGCATCTCATATGTATGCGTATATGCATCAGATGAACTGTTTTCCATCCCT

TTGATGTTCTATAAATAGACTCTATCACGGAAAAAAAAAAAAAAA

SEQ ID NO: 93

23_STR_91B4_T7_G03_023.abl.fa

GGAGCTAATTGCGCGCGGCCGCGGTACGACGAACCTGCGCATGGATACGAAGTGGGGTGGGA

GAAGCTCACCCACTGTGACTTTTAAGAACTCCTGTGTGATGGGAGGAAGGTACAGGTTCCTC

ACCATCCCCAGCCCTTCCTCTGGATGAGGATGTGAAGGACAGAGGCATCTCCAAAATGGGCT

ACTTTTGGTATAGACCTTAGGAGTGTGGGCTGGTGTAAGCTCTTGGTTCCTTTAAAAGGAG

AATTTTATTTTGTTTTGTTCAGTTTAGACATTCCTGGATGCAGTTTGATTGGTTAAATTAAA

AGTTGATTTTTTTTCCAGTAAAAAAAAAAAAAAAAAA

SEQ ID NO: 94

FUNDII1.36

TTAAAACTGCTTACCAGTGGCTGTCTGCGCTGCGGAAGGTGAGCATCAACAACACGGGACTG

TTGGGCTCCTACCACCCTGGCGTCTTCCGTGGGGACAAGTGGAGCTGCTGCCACCAAAAAGA

TABLE 8-continued

GAAGACAGGTCAGGGCTGCGATAAGACCCGGNCACGGGTGACCCTGCAGGAGTGGAATGACC

CTNTTGACCGTGACCTTGAGGCCCANCTCATCTACCGGCACCTGCTGGGCGNGGAGGCCATG

CTGTG

SEQ ID NO: 95

FUNH1III.12

CNCCCCAGGCTAAAGAGCAGGTGGGTGGGCTTGGACTGGGCGTGCTCCATGGCAGAGATCCT

GCGGTCACTCAACAGTGCCCCACTGTGGCGTGATGTCATTGCCACCTTCACAGACCACTGCA

TCAAGCAGCTGCCATTCCCTTATCGTCGTCGTCCT

SEQ ID NO: 96

FUNGIII1.13

GATAAGAGAATCCTTCATCTTTGACCTGGCTTTTTTTCGCCCTTTGGGAGATAAAGGTCCCT

CTCCACCCTCTACTAACACTCTGCACCCAAGGCCTTATCCTTTGGGGTCACCAGCTCCTTGG

CCATTTCTATGTGATTTCCCCCACCCATCTGAGTTCCAGTTTCCTCTGGGCTCCAATCTCCA

GTCCCTGCGGATCTGGTCAGTCCCACCCCTAGG

SEQ ID NO: 97

FUNDIII2.22

GATAAGCACACGGACCTTGAGCTGCTCCACGTGCCCCAGCACCTGAGCCCGCTCTTCTTCCA

GGGCTAGCACCTCTCCCTGGAGCTTGGTGCTAGGTGCATCTTCGTGCTCCTGCTGGGTGCTC

TCAGTGCCGCTGCACTCCTCCTTGAGATTTTCCTCATCTGAGCGCTCCATACTCTCCCATAG

GCGTTGGGTGGCAACTAGTTAGTTAG

SEQ ID NO: 97

FUNH5III.15

CATTGTCCTTGTAATCGATGGACGAATAGCGGAAAGTCGTGCACGAACACCAAGTGTCTCAT

AGTTGGGCTTATCGTCGTCGTCCTTGTAATCCATGGTG

SEQ ID NO: 99

FUNDIII3.59

GATAAGTGAGTGACCAGTTGTGTGGCATTTCTGCCTGCCAGACGGATGACATATACAACCGA

AACTGCCTTATTGAATTGGTCAACTGTCAGATGGTTCTTCGTGGAGCAGAGACAGAAGGCTG

TGTCATTGTGTCAGCTGCCAAAGCCCAACTGCTGCAGTGCCAGCACCATCCAGCCTGGTATG

GTGATACATTGAAGCAAAAGACATCCTGGACTTGCCTCTTGGTAGTTAGTTAG

SEQ ID NO: 100

FUNGII1.44

CTGCCTGCATCCTGGCCCCAGGTCTTCTTGGGGGCTTTGTCTGGA

SEQ ID NO: 101

FUNH2III.20

CNAAACACAAACAAATGAAGTGACTTGGGAGTTACCCCAATATCTTGCCACACAGGTACAGG

GATTACAGCATTACCAACCCAGTTCTGTGCCAGGTGCTGAAACTAGTTTTGTGGTAAATACA

GACATATATTCTAAGGAGAAAACGATTTCTGCTTATCGTCGTCGTCCT

SEQ ID NO: 102

FUNHII1 75

TABLE 8-continued

CCCGGTGGCCAGGGAACCCACTTCCAAGCGCAGGGACGCCGGCCTCCAGCTGGTTTGTGCTA

AGGCTCCGTCCTGACTGCCCTGTGCCCTGGAAAAGCAGCAATAGCATCCGCCCCTTAGAGCC

CTCTTATCGTCGTCGTCCTTGTAATCCATGGT

SEQ ID NO: 103

FUNGIII1.1

AAGCTTGGAGAGATGCGCCTGAAGGAGGCGGGCACGGTGGGGAGAGGAGGTGGGCAGGAGGA

ACGGCCCTTTGTGGCCCGGTTTGGATTTGACGTGGTGACGTGCTGTGGATACCTCC

SEQ ID NO: 104

FUNDII1.21

TTCCTTAGCAGCTAAGCATTTGAATCAGACTTCTCATAGCANTGTTATGGGCTGTCTGATAT

ATTCAGGATTTGTTGAGCAGATAAGCTGTGTGTGATCTTACTCATTCTCAGCCATGCCGCAG

ACATACCCATTTCCCTTTAGTAATTTTTTAATACAGAGAATGCTATTAAC

SEQ ID NO: 105

FUNDII1.37

AAGCACAAGCGTGGTAGTAGATCAGGTACTGTATCAAAGAGGCAGAGGGCTGTAAGTATGAG

TGGGCTGGGCTGCAAGACTTCTATACCATCCTAGATCACTAGACCGCACCCAGCATANAGAT

GGAGGAAGGAGGCCC

SEQ ID NO: 106

FUNHII1.85

CCCTTAGACCTTCCCTCAACAGAGGACACTGAGCCCAACGGAGTTCTGGGATGGGAGGGGTG

GGAGCATGGGAAGGGAGGCATCCCACCCCCAAGAAGAACTGAATAAAGATTGCTGAGCTTAT

CGTCGTCGTCCTTGTAATCCATGGT

SEQ ID NO: 107

FUNGII1.46

CCTGTGGATTTGACCTCAGAGATAAGTGGGACAGAGCTTGGTAGAAGCACCAGTGTGGGCAA

AGGTCCTGAGTCTGAACAGAACATGGCATGTGAGGAATGAAGCAGCCTGGCCCTAGGNGAAG

CTGANAAAACCCTGCAGGTCCTTGNAATCCATGGT

SEQ ID NO: 108

FUNGII1.23

TCCCCACGGGGTCCCGCANGGTACCACCCCACTCCGCTCCTCAAACGGGGCCGACATAATCC

AGTCCCTCCCGGCCGCGGCCGCACCACCCCACTCCGCTTATCGTCGTCGTCCTTGTAATCCA

TGGT

SEQ ID NO: 109

FUNDII1.33

TCCCTCTTTCAGAACCCTGNCAGACACCACCTCCTTTGTAACCTTAAAGCAGGTTCACAGAC

TATCTCCTGGTTCTTAGGGATTTCTTCTGTCGAAAAGAGTTCTNAAAAATAACAGNAACCTG

AGATACCATCTGTTAAATNCTTAAGCAATTTCGCATGCCTTATGAGACCNTGCTGATTAAAA

ACATCTAGTCTTGTTTTCTTTTTTTGAGACGAANTCTCGCTCTGTCA

SEQ ID NO: 110

TABLE 8-continued

FUNH4III.9

TTCCTGAGGAGCGACATGTGGTTGAACGCCTGGACGGGACACAAGCGGACCAAGGAAAGAGT

GGCATGGTCCACCCTCTCAAGGGCCTAGCTATCATGATACGAGGCGAATGGG

SEQ ID NO: 111

FUNGII1.15

TTAATCCGTTTGAAACTCATCAGGATTTGNCAGGGGAGTCGGATGAGCTTGGCATTTCCCAG

GATGAGCAGCTATCCAAGTTTAGTTTAAGGGAAACCACAGGCTCCGAGAGTGATGGGGGTGA

CTCAAGCAGCACCAAGTCTGAAGGTGCCAACGGGACAGTGGCAACTGCAGNAATCCAGCCCA

AGAAAGTTAAGCTTATCGTCGTCGTCCTTGTAATCCATGGT

SEQ ID NO: 112

FUNDII1.54

TGTAATACCGTTGGTTACAGGACACGCGGGGCANGGGAGCGTGAGGCTTAGGAGCAATTAGG

AGACAAAGGTTCTGCTTTCCACCAAACCTTCTTCGGTCTGGGCCCTCCCTTAGCAACCCTGG

GGCTTTAGACTCTCTCTCCACCAATCCCTGATGACCCCGGTGGTGCCTCACAATGGGCATTC

CAAGTAGCGCCCG

SEQ ID NO: 113

FUNGIII1.24

GATAAGTTTCATTTTTGGAAGGGCTGCATTAACAAATATTTGATTTCTTAGTTCACAGTCAA

GGACCTGTTGAGAAATCTGAGCTCGACTTGTAGGCTTAATTAGTTAGTTAGGATCCTAACTA

ACTAGGGACCTGGACAGCATCTTCCGCCGTATCAGGACGCTGAAAGGGAAACTGGCCAGGCA

GCACCCAGAGGCCTTCAGCCATATCCCAGAGGCATCCTTCCTGGAGGAAGAGGATGCTTATC

GTCC

SEQ ID NO: 114

FUNDIII3.55

GATAAGCCAGGGGCAGAAGGTAGAGCCCATGGGGCTGCTCTGGCTGTAGGTTTAGGCCCAG

CACCCCTCCCGAGGCAGCATAAGCAGGAGAGAAGAAGGCTAGTCCTTGGCACCACAAGGCCC

CGAGGGCAGCCACAGCCTCGGCCTGGTAGTTAGTTAG

SEQ ID NO: 115

FUNDII1.29

CTTTTTTTCCTTAACACNCCGGCCGNGGCTGTGGCTGCCCTCGGGGCCTTGTGGTGCCAAGG

ACTAGCCTTCTTCTCTCCTGCTTATGCTGCCTCGGGAGGGGTGCTGGGCCTAAACCTACAGC

CAGAGCAGCCCCATGGGCTCTACCTTNTGCCCCCTGG

SEQ ID N0: 116

FUNDII1.49

TTTATACCTTAAGNCTTCCCTGTCCCCTCTACCCAGATCATTTGGGAAATATAAATGTGCAG

TCCTAAGCGCTGCCCGCAGGGTCGCGATGTCTGCCAGGTACTGCTGGCTGGCTCTAGACACC

AGCAGCAGTGATAAGAAACAAAGCAGAGGAGACGTTGAGGCAGCAGAGACAGCAGATCCG

SEQ ID NO: 117

FUNDIII2.39

GATAAGCTTTTCAGTAACATTTTATACATCTACTTGTCAATGTATTTGAGACATTCACAGCC

TABLE 8-continued

AAAAGCCTGGGACTCTTTGTGAAGGTCCTCCTCACCTCTATCTTTCTTTCTCTCTCTCAA

ACTTTCCTTAAAGTTCTCATTGCCTTTGCACTGCTTCTGTGAACAGTCTTTGTCTCCTCCCC

ACCTTTGGTGGGAAGTGCGGNGCAGTCCTGGTCAAGACACTCATGCCCTGGCAATGTGGCTG

CCTAGTTAGTTAG

SEQ ID NO: 118

FUNHII1.76

TGAGATGCACACAAAGGAAAGGTGTGAGAGTGCTTGGAAGCATCCAGCTGAGCCCACTGGAT

GAAAATCAGACGATAGGGCCTCCTGTTGTAATCTTATCGTCGTCGTCCTTGTAATCCATGGT

SEQ ID NO: 119

FUNDII1.75

CCTTTGGACAGAACGACTCGATGCTATGGGGCGCCGCGGCCCAGCTGACTCGGATCTTCTCG

TCCCGGTCGGCAGTGAGGATGAAGCGGTCATCAGGACTCACAGCCACATCTAACAGCATAGA

CAGGTGCCCCAGCTCTAGACGGCCACACCCGTGTGGCTCCAGCACCGAAAAGGAGTAGACGT

CTCCAGACTTGTCGGCCACCAAGACCTTCTCCTCCGAGGCTATGAAAGTCAG

SEQ ID NO: 120

FUNH2III.7

CNAGATACACAGATAGGANCACATGTNCCTGGNCCGTTACACAACACCAAATCTGGCTTCAC

CCTGNGAATTAGGGGAAAGGAGAGCCACATGGAGTGCAAGGTGGTGAAAACGGTGGAGGGCC

AGGACTGCTGAAC

SEQ ID NO: 121

FUNGIII2.32

ATAAGCGTGGGTTCATACATGCATTGGGTGCTAGGCCCCAGCCTGCCGGGTGGCACCCTTTA

CAGTTCCTTTGAACAGGGTAGTTAGTTAG

SEQ ID NO: 122

FUNDII1.18

CCCGAAAGCGNGTAAGGCCTCCAGACCACCAACACTCAGCTCAAGTCAAACGTCCCTCTGTG

TCCAAAGAGGGGAGGAAAACATCCATCAAATCTCATNNGTCTGGGTCTCCAGGCCCTGGTGG

NAGCAACACATTTTTNATCCACACCAGTCATTGGGGCAGTGATAAG

SEQ ID NO: 123

FUNHII1.71

GCCGATGCAACAACCACATTGACTCCAAGGACAATCTAAAATTGAACTCAAGGCAGCACCTA

ACAAGTCTCTCGTGCTTGCACCCTCCTTCTAGGCCCATCTAAAAGCCTCTCTGCCTCAGGCG

TTCTCCCAGAAGATCTGCCCACTCTCTTCCCCACACCAGCC

SEQ ID NO: 124

FUNHII1.64

CTCTACATTGTGGCCCTCAATAATAGAATAAATTTGTGAAAAAGCTGCATGTTTTAATTTAG

GAAATGAGTAGAAGTTCACAAGCAACCCAGAATAGGTGCCAGCAGTTTGCTCCAGTGGGCCA

CACCACAGCAGCAGCTCAGGCTCTGCAGAATCACTGTGTCCAGTGCTTCC

SEQ ID NO: 125

TABLE 8-continued

FUNHII1.59

ACCTGCTTCTGAAGCTCCAACCTCCTCCCTCACCATATTGTAGCCATAGTAGCCTTTCTCAT

CCAAATTATGCCAACTTTCTATCTCCTCATGAGATATTTGCACCTGCCGTTCCCAGTAACCT

CAGGGCTCAGTGCATGAGTTGAAGCTGCCTTTCT

SEQ ID NO: 126

FUNGII1.5

CCATCTAAGGGCCCGTCACAGCTTTGTCTGTTGCCCCAGAATTTCGACGCCTTGGTTTGGCT

GCTAAACTTATGGAGTTNCTAGAGGAGATTTCAGAAAGAAAGGGTGGATTTTTTGTGGATCT

SEQ ID NO: 127

FUNGIII1.23

GATAAGAGTTGCAGTCAGGCTTCATACGCTATTGTCCTGCCCGTAAGTTCCCGTTTTGTGTG

TGGTTAGAGCAGCCAGCGGGTACAGAATGGATTTTGGAAGAGGGAGTCACCACTGGACCTCC

AAGGAAGCCACGTGCAGACATCTACACAGGATGAATGCGGGTGTTGGTAGTTAGTT

SEQ ID NO: 128

FUNDII1.5

TGTGAAGAACCTGTATCCNCTTAGAAAGTGTCTTTTGTCCTGGGGTGAGAGGGTGACTGCAT

GTGCCCTCTNGCAGTCTGCTGCTGTGTCCAGAGTCCGACTCCAGCTGGGCTGTAACTGGGCT

TGGCCCCCGCCTTAGGCCCCGCCAGCAGGCGAAGCAGGGAGATGTCAGACTGCTACACGGAG

CTGGAGAAGGCAGTCNTTGTCCT

SEQ ID NO: 129

FUNH2III.3

TTTATACCATTTNCCCCTNGGTGAACAGTCCTACAAGCAGCCTGNAGATTCTTCTCCCTACA

TCTCCTGTAAGGACGAAGGAGTGGTGTAACCTGAGCTCCGGCCCTGTGGAGACCCTCATGAG

GCCTGAGGCTAAG

SEQ ID NO: 130

FUNGII1.37

CCCCTCTTCCTCAACGGCAACAAAAACTCCCCAAGTCAGCACTCTNNTTATTTTATACGCCA

CAACCCTCTTGTAATCCATGGT

SEQ ID NO: 131

FUNH5III.8

AGTTGAATATTTATCCAACTCAGAAGACCCTAAAAAAGCACTTGTTCGATTCTTTGAGGCTG

TTGGTGTAACTTACGGGAACGTCCAGACACTTTCTGATAAATCTGCCATGGTCACAAA

---

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

REFERENCES

Abe et al, "Specific inhibition of influenza virus RNA polymerase and nucleoprotein gene expression by liposomally encapsulated antisense phosphorothioate oligonucleotides in MDCK cells", *Antivir Chem Chemother* 9:253–262 (1998)

Adams et al, "Complementary DNA sequencing: expressed sequence tags and human genome project", *Science* 252 (5013):1651–1656 (1991)

Ausubel et al (Eds), *Current Protocols in Molecular Biology*, John Wiley & Sons, Inc. (New York, 1994–2000)

Bai et al, "Gene transfer to vein graft wall by HVJ-liposome method: time course and localization of gene expression", *Ann Thorac Surg* 66:814–819 (1998)

Belecky-Adams et al, "Intragenic sequences are required for cell type-specific and injury-induced expression of the rat peripherin gene", *J Neurosicence* 13:5056–5065 (1993)

Bochot et al, "Liposomes dispersed within a thermosensitive gel: a new dosage form for ocular delivery of oligonucleotides", *Pharm Res* 15:1364–1369 (1998)

Boutin et al, "Identification of a cDNA encoding a long form of prolactin receptor in human hepatoma and breast cancer cells," *Molec Endocrinol* 3(9):1455–1461 (1989)

Braun et al, "A novel human muscle factor related to but distinct from MyoD1 induces myogenic conversion in 10T1/2 fibroblasts", *EMBO J* 8(3):701–709 (1989)

Cantor et al, "Ribozyme cleaves rex/tax mRNA and inhibits bovine leukemia virus expression", *Proc Natl Acad Sci*, 90(23):10932 (1993)

Cao et al, "Lymphotactin gene-modified bone marrow dendritic cells act as more potent adjuvants for peptide delivery to induce specific antitumor immunity",*J Immunol* 161:6238–6244 (1998)

Capaccioli et al, "Cationic lipids improve antisense oligonucleotide uptake and prevent degradation in cultured cells and in human serum", *Biochem Biophys Res Comm* 197:B18–825 (1993)

Chan et al, "Molecular cloning and localization to chromosome 6 of mouse INT1L1 gene", *Somatic Cell Molec Genet* 15(6):555–562 (1989)

Chen et al, "Inhibition of HIV-1 replication by novel multitarget ribozymes", *Ann NY Acad Sci* 660:271–273 (1992)

Croyle et al, "Development of a highly efficient purification process for recombinant adenoviral vectors for oral gene delivery", *Pharm Dev Technol* 3(3)365–372 (1998)

Daniel et al, "Retroviral transfer of antisense sequences results in reduction of C-Abl and induction of apoptosis in hemopoietic cells", *J Biomed Sci* 5:383–394 (1998)

Davis et al (eds.), *Basic Methods in Molecular Biology*, Elsevier Press, NY (1986)

Edinger et al, "Use of GPR1, GPR15, and STRL33 as coreceptors by diverse human immunodeficiency virus type 1 and simian immunodeficiency virus envelope proteins", *Virology* 249:367–378 (1998)

Fang et al, "A packaging system for SV40 vectors without viral coding sequences", *Anal Biochem* 254:139–143 (1997)

Flanagan, W M, "Antisense comes of age", *Cancer Metastasis Rev*, 17(2):169–176 (1998)

Galizzi et al, Molecular cloning of a cDNA encoding the human interleukin 4 receptor", *Int Immunol* 2(7):669–675 (1990)

Gennaro, A R (ed.), *Remington's Pharmaceutical Sciences*, Mack Publishing Company, Easton, Pa., 1990, pp 1521–1712

Gerster et al, "Quantitative analysis of modified antisense oligonucleotides in biological fluids using cationic nanoparticles for solid-phase extraction", *Anal Biochem* 262:177–184 (1998)

Gould et al, "Use of the DNA polymerase chain reaction for homology probing: isolation of partial cDNA or genomic clones encoding the iron-sulfur protein of succinate dehydrogenase from several species", *Proc Nat Acad Sci USA* 86(6):1934–1938 (1989)

Griscelli et al, "Heart-specific targeting of beta-galactosidase by the ventricle-specific cardiac myosin light chain 2 promoter using adenovirus vectors", *Hum Gene Ther*, 9:1919–1928 (1998)

Guang-Lin et al, "Adenovirus-mediated gene transfer of CTLA4IG gene results in prolonged survival of heart allograft", *Transplant Proc*, 30:2923–2924 (1998)

Guinot et al, "Antisense oligonucleotides: a new therapeutic approach", *Pathol Biol*, 46:347–354 (1998)

Gutkowska et al, "Circulating forms and radioimmunoassay of atrial natriuretic factor", *Endocrinol Metab Clin North Am* 16(1):183–198 (1987)

He et al, "Molecular cloning of androgen receptors from divergent species with a polymerase chain reaction technique: complete cDNA sequence of the mouse androgen receptor and isolation of androgen receptor cDNA probes from dog, guinea pig and clawed frog, *Biochem Biophys Res Comm* 171(2):697–704 (1990)

Hemmi et al, "The presence of human coxsackievirus and adenovirus receptor is associated with efficient adenovirus-mediated transgene expression in human melanoma cell cultures", *Hum Gene Ther* 9:2363–2373 (1998)

Higuti et al, "Molecular cloning of cDNA for the import precursor of human subunit B of H(+)-ATP synthase in mitochondria", *Biochem Biophys Res Comm* 178(3): 1014–1020 (1991)

Hofmann et al, "Rapid retroviral delivery of tetracycline-inducible genes in a single autoregulatory cassette", *Proc Natl Acad Sci* 93(11):5185–5190 (1996)

Hsieh et al, "Chromosome localization and cDNA sequence of murine and human genes for ras p21 GTPase activating protein (GAP)," *Somat Cell Mol Genet* 15(6):579–590 (1989)

Imamura et al, "Molecular cloning and primary structure of rat thyroxine-binding globulin", *Biochemistry* 30(22): 5406–5411 (1991)

Iwata et al, "Structure of the mouse tyrosine hydroxylase gene", *Biochem Biophys Res Comm* 182(1):348–354 (1992)

Jakubiczka et al, "A bovine homologue of the human TSPY gene", *Genomics* 17(3):732–735 (1993)

James-Pederson et al, "Flanking and intragenic sequences regulating the expression of the rabbit alpha-globin gene", *J Bio. Chem* 270:3965–3973 (1995)

Jeung et al, "Molecular cloning of the full-length cDNA encoding the human calbindin-D9k", *FEBS Lett* 307(2): 224–228 (1992)

Joseph et al, "Optimization of an anti-HIV hairpin ribozyme by in vitro selection", *J Biol Chem* 268:24515 (1993)

Kähari et al, "Deletion analyses of 5'-flanking region of the human elastin gene. Delineation of functional promoter and regulatory cis-elements", *J Biol Chem* 265(16): 9485–9490 (1990)

Kanamaru et al, "Biological effects and cellular uptake of c-myc antisense oligonucleotides and their cationic liposome complexes", *J Drug Target* 5:235–246 (1998)

Kim et al, "A new non-viral DNA delivery vector: the terplex system", *J Controlled Release* 53(1–3):175–82 (1998)

Kita et al, "Growth inhibition of human pancreatic cancer cell lines by anti-sense oligonucleotides specific to mutated K-ras genes", *Int J Cancer* 80:553–558 (1999)

Kondo et al, "Modulation of apoptosis by endogenous Bcl-xL expression in MKN-45 human gastric cancer cells", *Oncogene* 17:2585–2591 (1998)

Kumar et al, "Antisense RNA: function and fate of duplex RNA in cells of higher eukaryotes", *Microbiol Mol Biol Rev*, 62:1415–1434 (1998)

Langner et al, "Viral particles with heterologous binding motifs. An approach to specifically alter the tropism of the B-lymphotropic papovavirus", *Adv Exp Med Biol* 451:415–422 (1998)

Libert et al, "Cloning and functional characterization of a human A1 adenosine receptor", Biochem Biophys Res Comm 187(2):919–926 (1992)

Lockyer et al., "CAPRI regu.ates $Ca^{2+}$-dependent inactivation of the Ras-MAPK pathway," *Current Biology* 11:981–986, (2001)

Meinkoth et al, "Hybridization of nucleic acids immobilized on solid supports", *Anal Biochem* 138:267–284 (1984)

Meiri et al, "Memory and long-term potentiation (LTP) dissociated: normal spatial memory despite CA1 LTP elimination with Kv1.4 antisense", *Proc Natl Acad Sci*, 95:15037–15042 (1998)

Meyer et al, "Cationic liposomes coated with polyethylene glycol as carriers for oligonucleotides," *J Biol Chem* 273(25):15621–15627 (1998)

Minagawa et al., "Distinct phosphoinositide binding specificity of the GAP1 Family proteins: characterization of the Pleckstrin homology domains of MSARAL and KIAA0538," Biochem. Biophys. Res. Comm. 288:87–90 (2001)

Mizuguchi et al, "Efficient gene transfer into mammalian cells using fusogenic liposome", *Biochem Biophys Res Commun* 218:402–407 (1996)

Muranishi et al, "Lipophilic peptides: synthesis of lauroyl thyrotropin-releasing hormone and its biological activity", *Pharm Research* 8:649–652 (1991)

Nahmias et al, "Molecular characterization of the mouse beta 3-adrenergic receptor: relationship with the atypical receptor of adipocytes", *EMBO J* 10(12):3721–3727 (1991)

Nakamura et al, "A comparison of in vivo gene delivery methods for antisense therapy in ligament healing", *Gene Ther* 5:1455–1461 (1998)

Narumi et al, "Adenovirus vector-mediated perform expression driven by a glucocorticoid-inducible promoter inhibits tumor growth in vivo", *Am J Respir Cell Mol Biol* 19:936–941 (1998)

Nishida et al, "Adenovirus-mediated gene transfer to nucleus pulposus cells. Implications for the treatment of intervertebral disc degeneration", *Spine* 23:2437–2442, 1998

Noguchi et al, "Membrane fusion plays an important role in gene transfection mediated by cationic liposomes", *FEBS Lett* 433:169–173 (1998)

Oro et al, "The Drosophila gene knirps-related is a member of the steroid-receptor gene superfamily", *Nature* 336 (6198):493–496 (1988)

Paglia et al, "Gene transfer in dendritic cells, induced by oral DNA vaccination with Salmonella typhimurium, results in protective immunity against a murine fibrosarcoma", *Blood* 92(9):3172–3176 (1998)

Pederson et al, "Combined cytosine deaminase expression, 5-fluorocytosine exposure, and radiotherapy increases cytotoxicity to cholangiocarcinoma cells", *J Gastrointest Surg* 2:283–291 (1998)

Peng Ho et al, "Modification of phosphorothioate oligonucleotides yields potent analogs with minimal toxicity for antisense experiments in the CNS", *Brain Res Mol Brain Res* 62(1):1–11 (1998)

Potier et al, "The human glutamate receptor cDNA GluR1: cloning, sequencing, expression and localization to chromosome 5", *DNA Seq* 2(4):211–218 (1992)

Quattrone et al, "Enhancing antisense oligonucleotide intracellular levels by means of cationic lipids as vectors", *Biochemica* 1:25–29 (1995)

Reecy et al, "Multiple regions of the porcine alpha-skeletal actin gene modulate muscle-specific expression in cell culture and directly injected skeletal muscle", *Anim Biotechnol* 9:101–120 (1998)

Sambrook et al (Eds), *Molecular Cloning: A Laboratory Manual*, second edition, Cold Spring Harbor Laboratory Press, Cold Spring Harbor, (N.Y., 1989)

Schwarzenberger et al, "IL-17 stimulates granulopoiesis in mice: use of an alternate, novel gene therapy-derived method for in vivo evaluation of cytokines", *J Immunol* 161:6383–6389 (1998)

Shimayama et al, "Cleavage of the highly conserved hairpin-loop region of HIV-1 by synthetic ribozymes", *Nucleic Acids Symp Ser* 29:177–178 (1993)

Shoji et al, "Enhancement of anti-herpetic activity of antisense phosphorothioate oligonucleotides 5' end modified with geraniol", *J Drug Target* 5:261–273 (1998)

Shore et al, "Ribozyme-mediated cleavage of the BCRABL oncogene transcript: in vitro cleavage of RNA and in vivo loss of P210 protein-kinase activity", *Oncogene* 8:3183–3188 (1993)

Soni et al, "Biodistribution, stability, and antiviral efficacy of liposome-entrapped phosphorothioate antisense oligodeoxynucleotides in ducks for the treatment of chronic duck hepatitis B virus infection", *Hepatology* 28:1402–1410 (1998)

Soukchareun et al, "Use of Nalpha-Fmoc-cysteine(S-thiobutyl) derivatized oligodeoxynucleotides for the preparation of oligodeoxynucleotide-peptide hybrid molecules", *Bioconjug. Chem* 9(4):466–475 (1998)

Stix, G, "Shutting down a gene. Antisense drug wins approval", *Sci Am* 279(5):46, 50 (1998)

Sugawa et al, "An antisense EGFR oligodeoxynucleotide enveloped in Lipofectin induces growth inhibition in human malignant gliomas in vitro", *J Neurooncol* 39:237–244 (1998)

Sumimoto et al, "Complementary DNA for the mouse homolog of the small subunit of human cytochrome b558", *Biochem Biophys Res Comm* 165(2):902–906 (1989)

Tech et al, "Adenovirus vector-based purging of multiple myeloma cells", *Blood*, 92:4591–4601 (1998)

Waelti et al., "Delivery to cancer cells of antisense L-myc oligonucleotides incorporated in fusogenic, cationic-lipid-reconstituted influenza-virus envelopes (cationic virosomes)", *Int J Cancer* 77:728–733 (1998)

Wang, "Cyclic peptides incorporating 4-carboxyphenylalanine and phosphotyrosine are potent inhibitors of pp6 (c-) (src)", *J Controlled Release* 53:39–48 (1998)

Wang et al, "3-Hydroxy-3-methylglutaryl coenzyme A lyase (HL): cloning and characterization of a mouse liver HL cDNA and subchromosomal mapping of the human and mouse HL gene", *Mamm Genome* 4(7):382–387 (1993)

Weissig et al, "DQAsomes: a novel potential drug and gene delivery system made from Dequalinium", *Pharm Res* 15:334–337 (1998)

Yeh et al, "Inhibition of BMP receptor synthesis by antisense oligonucleotides attenuates OP-1 action in primary cultures of fetal rat calvaria cells", *J Bone Miner Res* 13:1870–1879 (1998)

Yotsuyanagi et al, "Cationic liposomes in gene delivery", *Nippon Rinsho* 56:705–712 (1998)

Zacharia et al, "New reduced peptide bond substance P agonists and antagonists: effects on smooth muscle contraction", *Eur J Pharmacol* 203:353–357 (1991)

Zhao et al, "Generating loss-of-function phenotypes of the Fushi tarazu gene with a targeted ribozyme in Drosophilala", *Nature* 365:448–451 (1993)

---

What is claimed is:

1. A method of identifying a neuroprotective compound comprising testing the ability of the compound to inhibit the activity of a $Ca^{+2}$ promoted Ras inactivator encoded by a member of the KIAA0538 gene family, said inactivator being encoded by a nucleic acid sequence comprising SEQ ID NO:94, whereby if the compound inhibits the activity of said inactivator, it is identified as being a neuroprotective compound.

2. A process for identifying a neuroprotective compound which specifically inhibits the activity of the polypeptide product of the KIAA0538 gene, said polypeptide product being encoded by a nucleic add sequence comprising SEQ ID NO:94, comprising:

(a) contacting cells expressing DNA encoding the KIAA0538 gene under conditions permitting expression of the DNA; and (b) determining if the compound inhibits the activity of the polypeptide product as compared to a control, thereby identifying a compound as neuroprotective.

3. The process of claim 2 wherein the cells are transfected with a nucleic acid comprising the sequence of SEQ ID NO:94.

4. The method or process of claim 1 or 2 wherein the cells endogenously express the KIAA0538 gene.

5. The method or process of claim 1 or 2 wherein the cells are neuronal cells.

* * * * *